US010322112B2

(12) United States Patent
Blackwell et al.

(10) Patent No.: US 10,322,112 B2
(45) Date of Patent: Jun. 18, 2019

(54) COMPOUND COMBINATIONS FOR ATTENUATION OF BACTERIAL VIRULENCE

(71) Applicant: WISCONSIN ALUMNI RESEARCH FOUNDATION, Madison, WI (US)

(72) Inventors: Helen Blackwell, Middleton, WI (US); Michael Welsh, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/431,295

(22) Filed: Feb. 13, 2017

(65) Prior Publication Data

US 2017/0231962 A1 Aug. 17, 2017

Related U.S. Application Data

(60) Provisional application No. 62/294,921, filed on Feb. 12, 2016.

(51) Int. Cl.
| | | |
|---|---|---|
| *A61K 31/165* | (2006.01) | |
| *A61K 31/365* | (2006.01) | |
| *A61K 31/381* | (2006.01) | |
| *A61K 31/4015* | (2006.01) | |
| *A61K 31/4184* | (2006.01) | |
| *A01N 43/52* | (2006.01) | |
| *A61K 45/06* | (2006.01) | |

(52) U.S. Cl.
CPC .......... *A61K 31/4184* (2013.01); *A01N 43/52* (2013.01); *A61K 31/165* (2013.01); *A61K 31/365* (2013.01); *A61K 31/381* (2013.01); *A61K 31/4015* (2013.01); *A61K 45/06* (2013.01)

(58) Field of Classification Search
CPC .. A61K 31/165; A61K 31/365; A61K 31/381; A61K 31/4015; A61K 31/4184
See application file for complete search history.

(56) References Cited

U.S. PATENT DOCUMENTS

| | | | |
|---|---|---|---|
| 7,883,720 B2 | 2/2011 | Lynn et al. | |
| 7,910,622 B2 | 3/2011 | Blackwell et al. | |
| 8,071,210 B2 | 12/2011 | Lynn et al. | |
| 8,815,943 B2 | 8/2014 | Blackwell et al. | |
| 8,877,940 B2 * | 11/2014 | Rahme ................. | C07D 235/28 548/307.1 |
| 9,796,694 B2 * | 10/2017 | Blackwell ............. | A61K 31/365 |
| 2008/0286345 A1 | 11/2008 | Lynn et al. | |
| 2009/0105375 A1 | 4/2009 | Lynn et al. | |
| 2009/0123512 A1 * | 5/2009 | Muh ..................... | A61K 31/165 424/423 |

OTHER PUBLICATIONS

Allen R. C. et al. (Apr. 2014) Targeting virulence: can we make evolution-proof drugs? Nat. Rev. Microbiol.12: 300-308.
Amara N. et al. (2011) Macromolecular inhibition of quorum sensing: enzymes, antibodies, and beyond. Chem. Rev. 111:195-208.
Amara N. et al. (2009) Covalent Inhibition of Bacterial Quorum Sensing. J. Am. Chem. Soc. 131:10610-10619.
Balasubramanian D. et al. (2013) A dynamic and intricate regulatory network determines *Pseudomonas aeruginosa* virulence. Nucleic Acids Res. 41(1):1-20.
Broderick A. H. et al. (Apr. 2011) Fabrication and Selective Functionalization of Amine-Reactive Polymer Multilayers on Topographically Patterned Microwell Cell Culture Arrays. Biomacromolecules 12:1998-2007.
Buck M. E. et al. (Apr. 2010) Functionalization of Fibers Using Azlactone-Containing Polymers: Layer-by-Layer Fabrication of Reactive Thin Films on the Surfaces of Hair and Cellulose-Based Materials. ACS Applied Materials & Interfaces 2(5):1421-1429.
Buck M. E. et al. (Mar. 2010) Reactive Layer-by-Layer Assembly of Suspended Thin Films and Semipermeable Membranes at Interfaces Created Between Aqueous and Organic Phases. Adv Mater. 22(9): 994-998.
Buck M.E. et al. (Sep. 2010) Free-Standing and Reactive Thin Films Fabricated by Covalent Layer-by-Layer Assembly and Subsequent Lift-Off of Azlactone-Containing Polymer Multilayers. Langmuir 26(20):16134-16140.
Buck M.E. et al. (May 2009) Chemical Modification of Reactive Multilayered Films Fabricated from Poly(2-alkenyl azlactone)s: Design of Surfaces that Prevent or Promote Mammalian Cell Adhesion and Bacterial Biofilm Growth. Biomacromolecules 10(6):1564-1574.
Buck M.E. et al. (Nov. 2010) Superhydrophobic Thin Films Fabricated by Reactive Layer-by-Layer Assembly of Azlactone-Functionalized Polymers. Chem. Mater. 22(23): 6319-6327.
Bundgaard H. (1991) Design and Application of Prodrugs, Chapter 5, In: *A Textbook of Drug Design and Development*, edited by Krosgaard-Larsen and H. Bundgaard, Harwood Academic Publishers, Philadelphia, pp. 113-191.
Bundgaard H. (1992) Means to Enhance Penetration. (1) Prodrugs as a means to improve the delivery of peptide drugs. Advanced Drug Delivery Reviews 8:1-38.

(Continued)

*Primary Examiner* — Zohreh A Fay
(74) *Attorney, Agent, or Firm* — Leydig, Voit & Mayer, Ltd.

(57) ABSTRACT

Methods for modulating quorum sensing in certain Gram-negative bacteria having multiple QS systems including Las, Rhl, and Pqs with associated receptors (LasR, RhlR and PqsR) which are modulated by small molecule modulators, particularly non-native modulators. Certain combinations of modulators of Las, Rhl and Pqs exhibit improved inhibition of virulence in comparison to the respective individual modulators. In particular, certain combinations of modulators exhibit improved inhibition in nutritionally depleted environments. More specifically, certain combinations of modulators exhibit improved inhibition in environments depleted in phosphate and/or environments depleted in iron. Nutrient depleted environments can mimic environments associated with bacterial infection in humans and non-human animals. The methods are useful in particular for modulating QS in *Pseudomonas* and *Burkholderia*.

10 Claims, 27 Drawing Sheets

Specification includes a Sequence Listing.

(56) References Cited

OTHER PUBLICATIONS

Cabeen M.T. (Feb. 2014) Stationary phase-specific virulence factor overproduction by a lasR mutant of Pseudomonas aeruginosa. PLOS ONE 9(2), e88743, pp. 1-9.
Camilli A. et al. (Feb. 2006) Bacterial small-molecule signaling pathways. Science 311:1113-1116.
Cao H. et al. (Dec. 2001) A quorum sensing-associated virulence gene of Pseudomonas aeruginosa encodes a LysR-like transcription regulator with a unique self-regulatory mechanism. Proc. Natl. Acad. Sci. 98(25):14613-14618.
Cegelski L. et al. (Jan. 2008) The biology and future prospects of antivirulence therapies. Nat. Rev. Microbiol. 6:17-27.
Chen G. et al. (Apr. 2011) A strategy for antagonizing quorum sensing. Mol. Cell 42:199-209.
Costas C. et al. (Apr. 2015) Using surface enhanced Raman scattering to analyze the interactions of protein receptors with bacterial quorum sensing modulators. ACS Nano 9(5):5567-5576.
Cugini C. et al. (Jul. 2007) Farnesol, a common sesquiterpene, inhibits PQS production in Pseudomonas aeruginosa. Mol. Microbiol. 65(4):896-906.
D'Argenio D. A. et al. (2007) Growth phenotypes of Pseudomonas aeruginosa lasR mutants adapted to the airways of cystic fibrosis patients. Mol. Microbiol. 64(2):512-533.
Davenport P. et al. (Jun. 2015) Quorum sensing is accompanied by global metabolic changes in the opportunistic human pathogen, Pseudomonas aeruginosa. J. Bacteriol. 197(12):2072-2082.
Dekimpe V. et al. (2009) Revisiting the quorum-sensing hierarchy in Pseudomonas aeruginosa: the transcriptional regulator RhlR regulates LasR-specific factors. Microbiology 155:712-723.
Déziel E. et al. (2005) The contribution of MvfR to Pseudomonas aeruginosa pathogenesis and quorum sensing circuitry regulation: multiple quorum sensing-regulated genes are modulated without affecting lasRI, rhlRI or the production of N-acyl-L-homoserine lactones. Mol. Microbiol. 55(4):998-1014.
Diggle S. P. et al. (2003) The Pseudomonas aeruginosa quinolone signal molecule overcomes the cell density-dependency of the quorum sensing hierarchy, regulates rhl-dependent genes at the onset of stationary phase and can be produced in the absence of LasR. Mol. Microbiol. 50(1):29-43.
Duan K. et al. (Jul. 2007) Environmental regulation of Pseudomonas aeruginosa PAO1 Las and Rhl quorum-sensing systems. J. Bacteriol. 189(13):4827-4836.
Eibergen, N. R., Moore, J. D., Mattmann, M. E. & Blackwell, H. E. (2015). Potent and selective modulation of the RhlR quorum sensing receptor by using non-native ligands: an emerging target for virulence control in Pseudomonas aeruginosa. ChemBioChem, 16, 2348-2356.
Farha, M. A. & Brown, E. D. (2010). Chemical probes of Escherichia coli uncovered through chemical-chemical interaction profiling with compounds of known biological activity. Chem. Biol., 17, 852-862.
Folkesson, A., Jelsbak, L., Yang, L., Johansen, H. K., Ciofu, O., Høiby, N. & Molin, S. (2012). Adaptation of Pseudomonas aeruginosa to the cystic fibrosis airway: an evolutionary perspective. Nat. Rev. Microbiol., 10, 841-851.
Fuqua, C. & Greenberg, E. P. (2002). Listening in on bacteria: acyl-homoserine lactone signalling. Nat. Rev. Mol. Cell Biol., 3, 685-695.
Galloway, W. R. J. D., Hodgkinson, J. T., Bowden, S. D., Welch, M. & Spring, D. R.(2011).Quorum sensing in Gram-negative bacteria: small-molecule modulation of AHL and AI-2 quorum sensing pathways. Chem. Rev., 111, 28-67.
Gerdt, J. P. & Blackwell, H. E. (2014). Competition studies confirm two major barriers that can preclude the spread of resistance to quorum-sensing inhibitors in bacteria. ACS Chem. Biol., 9,469 2291-2299.
Geske, G. D., Mattmann, M. E. & Blackwell, H. E. (2008). Evaluation of a focused library of N-aryl L-homoserine lactones reveals a new set of potent quorum sensing modulators. Bioorg. Med. Chem. Lett., 18, 5978-5981(a).
Geske, G. D., O'Neill, J.C., Miller D.M., Wezeman, R.J., Mattmann, M.E., Lin, Q., Blackwell, H.E., (2008). Comparative analyses of N-acylated homoserine lactones reveal unique structural features that dictate their ability to activate or inhibit quorum sensing. ChemBioChem 9, 389-400 (b).
Geske, G. D., O'Neill, J. C., Miller, D. M., Mattmann, M. E. & Blackwell, H. E. (2007). Modulation of bacterial quorum sensing with synthetic ligands: systematic evaluation of N-acylated homoserine lactones in multiple species and new insights into their mechanisms of action. J. Am. Chem. Soc., 129, 13613-13625.
Geske, G. D.; Wezeman, R. J.; Siegel, A. P.; Blackwell, H. E. (2005) Small molecule inhibitors of bacterial quorum sensing and biofilm formation. J. Am. Chem. Soc. 127, 12762-12763.
Gilbert, K. B., Kim, T. H., Gupta, R., Greenberg, E. P. & Schuster, M. (2009). Global position analysis of the Pseudomonas aeruginosa quorum-sensing transcription factor LasR. Mol. Microbiol., 73, 1072-1085.
Goo, E., An, J. H., Kang, Y. & Hwang, I. (2015). Control of bacterial metabolism by quorum sensing. Trends Microbiol., 23, 567-576.
Hense, B. A. & Schuster, M. (2015). Core principles of bacterial autoinducer systems. Microbiol. 483 Mol. Biol. Rev., 79, 153-169.
Hentzer, M.; Wu, H.; Andersen, J. B.; Riedel, K.; Rasmussen, T. B.; Bagge, N.; Kumar, N.; Schembri, M. A.; Song, Z.; Kristoffersen, P.; Manefield, M.; Costerton, J. W.; Molin, S.; Eberl, L.; Steinberg, P.; Kjelleberg, S.; Hoiby, N.; Givskov, M. (2003) Attenuation of Pseudomonas aeruginosa virulence by quorum sensing inhibitors. EMBO J. 22, 3803-3815.
Hoang, T. T., Karkhoff-Schweizer, R. R., Kutchma, A. J. & Schweizer, H. P. (1998). A broad-host-range Flp-FRT recombination system for site-specific excision of chromosomally-located DNA sequences: application for isolation of unmarked Pseudomonas aeruginosa mutants. Gene, 212, 77-86.
Hodgkinson, J. T. et al. (2012). Design, synthesis and biological evaluation of non-natural modulators of quorum sensing in Pseudomonas aeruginosa . Org. Biomol. Chem., 10, 6032-6044.
Holloway, B. W. (1955). Genetic recombination in Pseudomonas aeruginosa. J. Gen. Microbiol., 13, 572-581.
Ishida, T.; Ikeda, T.; Takiguchi, N.; Kuroda, A.; Ohtake, H.; Kato, J. (2007) Inhibition of Quorum Sensing in Pseudomonas aeruginosa by N-Acyl Cyclopentylamides. Appl. Environ. Microbiol. 73, 3183-3188.
Jensen, V., Lons, D., Zaoui, C., Bredenbruch, F., Meissner, A., Dieterich, G., Munch, R. & Haussler, S. (2006). RhlR expression in Pseudomonas aeruginosa is modulated by the Pseudomonas quinolone signal via PhoB-dependent and-independent pathways. J. Bacteriol.,188, 8601-8606.
Koch, A. K., Käppeli, O., Fiechter, A. & Reiser, J. (1991). Hydrocarbon assimilation and biosurfactant production in Pseudomonas aeruginosa mutants. J. Bacteriol., 173, 4212-4219.
Lee, J., Wu, J., Deng, Y., Wang, J., Wang, C., Wang, J., Chang, C., Dong, Y., Williams, P. & Zhang, L.-H. (2013). A cell-cell communication signal integrates quorum sensing and stress response. Nat. Chem. Biol., 9, 339-343.
Lee, J. & Zhang, L. (2015). The hierarchy quorum sensing network in Pseudomonas aeruginosa. Protein Cell, 6, 26-41.
Long, J., Zaborina, O., Holbrook, C., Zaborin, A. & Alverdy, J. (2008). Depletion of intestinal phosphate after operative injury activates the virulence of P. aeruginosa causing lethal gut derived sepsis. Surgery, 144, 189-197.
Lu, C., Kirsch, B., Zimmer, C., De Jong, Johannes C., Henn, C., Maurer, Christine K., Müsken, M., Häussler, S., Steinbach, A. & Hartmann, Rolf W. (2012). Discovery of antagonists of PqsR, a key player in 2-alkyl-4-quinolone-dependent quorum sensing in Pseudomonas aeruginosa. Chem. Biol., 19, 381-390.
Lyczak, J. B., Cannon, C. L. & Pier, G. B. (2000). Establishment of Pseudomonas aeruginosa infection: lessons from a versatile opportunist. Microbes Infect., 2, 1051-1060.
Markou, P. & Apidianakis, Y. (2014). Pathogenesis of intestinal Pseudomonas aeruginosa infection in patients with cancer. Front. Cell. Infect. Microbiol., 3, 115.
Mattmann, M. E., Shipway, P. M., Heth, N. J. & Blackwell, H. E. (2011). Potent and selective synthetic modulators of a quorum

(56) References Cited

OTHER PUBLICATIONS sensing repressor in Pseudomonas aeruginosa identified from second-generation libraries of N-acylated L-homoserine lactones. ChemBioChem, 12, 942-949.

Mattmann, M.E., G. D. Geske, G. A. Worzalla, J. R. Chandler, K. J. Sappington, E. P. Greenberg, H. E. Blackwell (2008). Synthetic ligands that activate and inhibit a quorum-sensing regulator in Pseudomonas aeruginosa. Bioorg. Med. Chem. Lett. 18, 3072-075.

McInnis, C. E.; Blackwell, H. E. (2011). Thiolactone modulators of quorum sensing revealed through library design and screening. Biorganic & Medicinal Chemistry 194820-4828.

McInnis, C. E.; Blackwell, H. E. (2011) Design, synthesis, and biological evaluation of abiotic, non-lactone modulators of LuxR-type quorum sensing. Biorgan. Med. Chem. 19, 4812-4819.

Mellbye, B. & Schuster, M. (2014). Physiological framework for the regulation of quorum sensing-dependent public goods in Pseudomonas aeruginosa. J. Bacteriol., 196, 1155-1164.

Moore, J. D., Rossi, F. M., Welsh, M. A., Nyffeler, K. E. & Blackwell, H. E. (2015). A comparative analysis of synthetic quorum sensing modulators in Pseudomonas aeruginosa: New insights into mechanism, active efflux susceptibility, phenotypic response, and next-generation ligand design. J. Am. Chem. Soc., 137(46), 14626-14639.

Moore, J.D., Gerdt, J.P., Eibergen, N. R., Blackwell, H.E. (2014) Active efflux influences the potency of quorum sensing inhibitors in Pseudomonas aeruginosa. ChemBioChem 15, 435-442.

Morkunas, B et al. (2012). Inhibition of the production of the Pseudomonas aeruginosa virulence factor pyocyanin in wild-type cells by quorum sensing autoinducer-mimics. Org. Biomol., 42, 8452-8464.

Müh, U., Schuster, M., Heim, R., Singh, A., Olson, E. R. & Greenberg, E. P. (2006). Novel Pseudomonas aeruginosa quorum-sensing inhibitors identified in an ultra-high-throughput screen. Antimicrob. Agents Chemother., 50, 3674-3679(a).

Müh, U.; Hare, B. J.; Duerkop, B. A.; Schuster, M.; Hanzelka, B. L.; Heim, R.; Olson, E. R.; Greenberg, E. P. (2006) A structurally unrelated mimic of a Pseudomonas aeruginosa acyl-homoserine lactone quorum-sensing signal. Proc. Natl. Acad. Sci. U. S. A. 103, 16948-16952 (b).

Murray, E. J., et al. (2014). Targeting *Staphylococcus aureus* quorum sensing with nonpeptidic small molecule inhibitors. J. Med. Chem., 57, 2813-2819.

O'Brien, K.T.;Noto, J.G.; Nichols-O'Neill, L.; Perez, L.J. (2015). Potent Irreversible Inhibitors of LasR Quorum Sensing in Pseudomonas aeruginosa. ACS Medicinal Chemistry Letters, 6, 162-167.

O'Loughlin, C. T., Miller, L. C., Siryaporn, A., Drescher, K., Semmelhack, M. F. & Bassler, B. L. (2013). A quorum-sensing inhibitor blocks Pseudomonas aeruginosa virulence and biofilm formation. Proc. Natl. Acad. Sci. U. S. A., 110, 17981-17986.

O'Reilly, M. C. and Blackwell, H. E. (2015). Structure-Based Design and Biological Evaluation of Triphenyl Scaffold-Based Hybrid Compounds as Hydrolytically Stable Modulators of a LuxR-Type Quorum Sensing Receptor. ACS Infect. Dis, 2, 32-38.

Oglesby, A. G., Farrow, J. M., Lee, J.-H., Tomaras, A. P., Greenberg, E. P., Pesci, E. C. & Vasil, M. L. (2008). The influence of iron on Pseudomonas aeruginosa physiology: a regulatory link between iron and quorum sensing. J. Biol. Chem., 283, 15558-15567.

Persson, T.; Hansen, T. H.; Rasmussen, T. B.; Skinderso, M. E.; Givskov, M.; Nielsen, J. (2005) Rational design and synthesis of new quorum-sensing inhibitors derived from acylated homoserine lactones and natural products from garlic. Org. Biomol. Chem. 3, 253-262.

Praneenararat, T.; Palmer, A. G. & Blackwell, H. E. (2012). Chemical methods to interrogate bacterial quorum sensing pathways. Org. Biomol. Chem., 10, 8189-8199.

Rampioni, G., Pustelny, C., Fletcher, M. P., Wright, V. J., Bruce, M., Rumbaugh, K. P., Heeb, S., Cámara, M. & Williams, P. (2010). Transcriptomic analysis reveals a global alkyl-quinolone independent regulatory role for PqsE in facilitating the environmental adaptation of Pseudomonas aeruginosa to plant and animal hosts. Environ. Microbiol., 12, 1659-1673.

Recinos, D. A., Sekedat, M. D., Hernandez, A., Cohen, T. S., Sakhtah, H., Prince, A. S., Price-Whelan, A. & Dietrich, L. E. P. (2012). Redundant phenazine operons in Pseudomonas aeruginosa exhibit environment-dependent expression and differential roles in pathogenicity. Proc. Natl. Acad. Sci. U. S. A., 109, 19420-19425.

Reis, R. S., Pereira, A. G., Neves, B. C. & Freire, D. M. G. (2011). Gene regulation of rhamnolipid production in Pseudomonas aeruginosa—a review. Biores. Tech., 102, 6377-6384.

Reverchon, S.; Chantegrel, B.; Deshayes, C.; Doutheau, A.; Cotte-Pattat, N. (2002) New synthetic analogues of N-acyl homoserine lactones as agonists or antagonists of transcriptional regulators involved in bacterial quorum sensing. Bioorg. Med. Chem. Lett. 12, 1153-1157.

Rojo, F. (2010). Carbon catabolite repression in Pseudomonas: optimizing metabolic versatility and interactions with the environment. FEMS Microbiol. Rev., 34, 658-684.

Rutherford, S. T. & Bassler, B. L. (2012). Bacterial quorum sensing: its role in virulence and possibilities for its control. Cold Spring Harb. Perspect. Med., 2, a012427.

Schafhauser, J., Lepine, F., Mckay, G., Ahlgren, H. G., Khakimova, M. & Nguyen, D. (2014). The stringent response modulates 4-hydroxy-2-alkylquinoline (HAQ) biosynthesis and quorum sensing hierarchy in Pseudomonas aeruginosa. J. Bacteriol., 196, 1641-1650.

Schuster, M. & Greenberg, E. P. (2008). LuxR-type proteins in Pseuodomonas aeruginosa quorum sensing: Distinct mechanisms with global implications. In Chemical Communication Among Bacteria, Winans, S. C. & Bassler, B. L. eds. (Washington, DC: ASM Press), pp. 133-144.

Shrout, J. D., Chopp, D. L., Just, C. L., Hentzer, M., Givskov, M. & Parsek, M. R. (2006). The impact of quorum sensing and swarming motility on Pseudomonas aeruginosa biofilm formation is nutritionally conditional. Mol. Microbiol., 62, 1264-1277.

Simon, R., Priefer, U. & Puhler, A. (1983). A broad host range mobilization system for in vivo genetic engineering: Transposon mutagenesis in Gram negative bacteria. Nat. Biotechnol., 1, 784-791.

Smith, K. M.; Bu, Y.; Suga, H. (2003) Library screening for synthetic agonists and antagonists of a Pseudomonas aeruginosa autoinducer. Chem. Biol. 10, 563-571 (a).

Smith, K. M.; Bu, Y.; Suga, H. (2003) Induction and inhibition of Pseudomonas aeruginosa quorum sensing by synthetic autoinducer analogs. Chem. Biol. 10, 81-89 (b).

Starkey, M., et al. (2014) Identification of anti-virulence compounds that disrupt quorum sensing regulated acute and persistent pathogenicity. PLoS Pathog., 10, e1004321.

Swem, L. R.; Swem, D. L.; O'Loughlin, C. T.; Gatmaitan, R.; Zhao, B.; Ulrich, S. M.;Bassler, B. L. (2009) A Quorum-Sensing Antagonist Targets Both Membrane-Bound and Cytoplasmic Receptors and Controls Bacterial Pathogenicity. Mol. Cell 35, 143-153.

Turner, K. H., Wessel, A. K., Palmer, G. C., Murray, J. L. & Whiteley, 550 M. (2015) Essential genome of Pseudomonas aeruginosa in cystic fibrosis sputum. Proc. Natl. Acad. Sci. U. S. A., 112, 4110-4115.

Venturi, V. (2006). Regulation of quorum sensing in Pseudomonas. FEMS Microbiol. Rev., 30, 554 274-291.

Wagner, V. E., Bushnell, D., Passador, L., Brooks, A. I. & Iglewski, B. H. (2003). Microarray analysis of Pseudomonas aeruginosa quorum-sensing regulons: effects of growth phase and environment. J. Bacteriol., 185, 2080-2095.

Welsh, M. A., Eibergen, N. R., Moore, J. D. & Blackwell, H. E. (2015) Small molecule disruption of quorum sensing cross-regulation in Pseudomonas aeruginosa causes major and unexpected alterations to virulence phenotypes. J. Am. Chem. Soc., 137, 1510-1519.

White, C. E. & Winans, S. C. (2007) Cell-cell communication in the plant pathogen Agrobacterium tumefaciens. Phil. Trans. R. Soc. B, 362, 1135-1148.

Williams, P. & Cámara, M. (2009) Quorum sensing and environmental adaptation in Pseudomonas aeruginosa: a tale of regulatory networks and multifunctional signal molecules. Curr. Opin. Microbiol., 12, 182-191.

(56) References Cited

OTHER PUBLICATIONS

Wu, H.; Song, Z.; Hentzer, M.; Andersen, J. B.; Molin, S.; Givskov, M.; Høiby, N. J. (2004) Synthetic furanones inhibit quorum-sensing and enhance bacterial clearance in Pseudomonas aeruginosa lung infection in mice. Antimicrob. Chemother. 53, 1054-1061.

Yang, N., et al. (2015) The Crc protein participates in down-regulation of the Lon gene to promote rhamnolipid production and rhl quorum sensing in Pseudomonas aeruginosa. Mol. Microbiol., 96, 526-547.

Zakhari, J. S.; Kinoyama, I.; Struss, A. K.; Pullanikat, P.; Lowery, C. A.; Lardy, M.;Janda, K. D. (2011) Synthesis and Molecular Modeling Provide Insight into a Pseudomonas aeruginosa Quorum Sensing Conundrum. J. Am. Chem. Soc., 133, 3840-3842.

Zhu et al. (1998) Analogs of the Autoinducer 3-Oxooctanoyl-Homoserine Lactone Strongly Inhibit Activity of the TraR Protein ofAgrobacterium tumefaciens. J. Bacteriol. 180, 5398-5405.

\* cited by examiner

Exemplary RhIR Modulators-1

AR14

AR15

AR16

AR17

AR18

AR19

AR20

AR21

SEQUENCE LISTING

<160> NUMBER OF SEQ ID NOS: 8

<210> SEQ ID NO 1
<211> LENGTH: 28
<212> TYPE: DNA
<213> ORGANISM: Artificial sequence
<220> FEATURE:
<223> OTHER INFORMATION: synthetic primer

<400> SEQUENCE: 1
acttctagaa gcgttctcca gcagacgc                                      28

<210> SEQ ID NO 2
<211> LENGTH: 28

<212> TYPE: DNA
<213> ORGANISM: Artificial sequence
<220> FEATURE:
<223> OTHER INFORMATION: synthetic primer

<400> SEQUENCE: 2
tataagcttg gtgcgcgaca tgctcaag                                      28

<210> SEQ ID NO 3
<211> LENGTH: 33
<212> TYPE: DNA
<213> ORGANISM: Artificial sequence
<220> FEATURE:
<223> OTHER INFORMATION: synthetic primer

<400> SEQUENCE: 3
gtatctagac ccttattcct tttattgggt ggc                                33

<210> SEQ ID NO 4
<211> LENGTH: 27
<212> TYPE: DNA
<213> ORGANISM: Artificial sequence
<220> FEATURE:
<223> OTHER INFORMATION: synthetic primer

<400> SEQUENCE: 4
atagatgaat tcttgaggat cttcgcc                                       27

<210> SEQ ID NO 5
<211> LENGTH: 30
<212> TYPE: DNA
<213> ORGANISM: Artificial sequence
<220> FEATURE:
<223> OTHER INFORMATION: synthetic primer

<400> SEQUENCE: 5
gaatatggat cctctctccg cagatacctg                                    30

<210> SEQ ID NO 6
<211> LENGTH: 31
<212> TYPE: DNA
<213> ORGANISM: Artificial sequence
<220> FEATURE:
<223> OTHER INFORMATION: synthetic primer

<400> SEQUENCE: 6
gctattgaat tctgaagatg aatagcgcca c                                  31

<210> SEQ ID NO 7
<211> LENGTH: 28
<212> TYPE: DNA
<213> ORGANISM: Artificial sequence
<220> FEATURE:
<223> OTHER INFORMATION: synthetic primer

<400> SEQUENCE: 7
cagattgtcg actctctccg cagatacc                                      28

<210> SEQ ID NO 8
<211> LENGTH: 28
<212> TYPE: DNA
<213> ORGANISM: Artificial sequence
<220> FEATURE:
<223> OTHER INFORMATION: synthetic primer

<400> SEQUENCE: 8
cagctaggat ccgaagatga atagcgcc                                          28

COMPOUND COMBINATIONS FOR ATTENUATION OF BACTERIAL VIRULENCE

CROSS-REFERENCE TO RELATED APPLICATION

This application claims the benefit of U.S. Provisional application No. 62/294,921, filed Feb. 12, 2016, which application is incorporated by reference in its entirety herein.

STATEMENT REGARDING GOVERNMENT FUNDING

This invention was made with government support under GM109403 awarded by the National Institutes of Health. The government has certain rights in the invention.

BACKGROUND OF THE INVENTION

Many common bacterial pathogens can delay virulence factor production until there are a sufficient number of cells such that, working together, the group can overwhelm a host's defenses. To coordinate such an attack, some species use a method of cell-cell communication called quorum sensing (QS) (Camilli and Bassler, 2006; Rutherford and Bassler, 2012). In Gram-negative bacteria, QS involves the production of a membrane diffusible small molecule signal, often an N-acyl L-homoserine lactone (AHL), that accumulates in the surroundings at a concentration proportional to cell density (Fuqua and Greenberg, 2002). At a threshold concentration, this signal is bound by, and activates, an intracellular LuxR-type receptor that acts as a transcriptional regulator to induce the expression of group-beneficial genes.

QS systems are often induced in response to environmental signals (Hense and Schuster, 2015, Lee and Zhang, 2015). Such mechanisms allow the bacterium to delay the energetically costly production of QS signals and virulence factors until it is in an environment permissive to infection. Because of their association with virulence, QS systems are considered to be potential antivirulence targets (Cegelski et al., 2008, Allen et al., 2014, Gerdt and Blackwell, 2014).

A number of research groups are actively developing small molecule and macromolecular agents capable of inhibiting QS receptor activity (Galloway et al., 2011, Murray et al., 2014, Amara et al., 2011, Praneenararat et al., 2012).

The opportunistic pathogen *Pseudomonas aeruginosa* is highly adaptable to life in a variety of environments ranging from soil to water to skin. *P. aeruginosa* possesses a sophisticated QS system that incorporates a large degree of environmental regulation (Wagner et al., 2003, Duan and Surette, 2007, Williams and Cámara, 2009). *P. aeruginosa* has three QS systems—Las, Rhl, and Pqs (FIGS. 2A and 2B)—whose associated LuxR-type receptors (LasR and RhlR) and LysR type receptor PqsR; (also known as MvfR) regulate distinct subsets of virulence-associated genes upon activation by their cognate small molecule signal (Venturi, 2006, Schuster and Greenberg, 2008). Using these systems, *P. aeruginosa* is able to colonize a variety of mammalian tissues including, notoriously, the airways of patients suffering from cystic fibrosis (CF) (Lyczak et al., 2000, Folkesson et al., 2012). In the canonical model of *P. aeruginosa* QS, it has been understood that a regulatory hierarchy exists between the three QS systems, whereby Las induces the expression and activation of both Rhl and Pqs, while an inverse regulatory relationship exists between the latter systems (Balasubramanian et al., 2013).

Increasing evidence has revealed that nutritional cues found in infection environments can alter this hierarchy (Dekimpe and Déziel, 2009; Cabeen, 2014; Lee and Zhang, 2015). For example, cellular factors that sense low levels of iron and phosphate can directly stimulate the Rhl and Pqs systems, bypassing Las (FIG. 2B) (Jensen et al., 2006; Oglesby et al., 2008; Lee et al., 2013). In addition, the chemical nature and availability of carbon sources can suppress or induce specific QS systems via the downstream effects of carbon catabolite repression and the stringent response (FIG. 1A) (Shrout et al., 2006; Schafhauser et al., 2014; Yang et al., 2015). A plausible explanation for the existence of the complex QS network in *P. aeruginosa* is that it serves to tune the virulence profile of the organism in response to diverse environmental stimuli (Mellbye and Schuster, 2014).

Despite considerable recent research, a full understanding of the mechanisms by which Las, Rhl, and Pqs work together to accomplish this regulation remains elusive. Mellbye and Schuster have shown that Las-responsive genes are primarily induced in a cell density-dependent manner, while Rhl-associated genes are up-regulated in response to environmental cues (Mellbye and Schuster, 2014). Although Pqs is an important regulator of global virulence, how it fits into this model is unknown (Déziel et al., 2005; Rampioni et al., 2010). The inverse regulation between Rhl and Pqs suggests a close relationship; yet, the relative contribution of Rhl and Pqs to virulence factor production is poorly defined. Further, whether Las remains important for virulence factor production in wild-type (WT) *P. aeruginosa* under conditions that directly stimulate Rhl and Pqs is unclear. Thus, there is a need in the art for a more complete understanding of how these systems work together to coordinate virulence, particularly in defined, infection-relevant environments.

SUMMARY OF THE INVENTION

The invention relates to inhibition of virulence of Gram-negative bacteria. In particular, the invention relates to inhibition of virulence of species of *Pseudomonas*. More specifically, the invention relates to inhibition of virulence of *Pseudomonas aeruginosa*.

*P. aeruginosa* has three interacting QS systems Las, Rhl, and Pqs with associated receptors (LasR, RhlR and PqsR) which are modulated by small molecule modulators (FIGS. 1A and 1B). The native activators of QS have been identified, see FIG. 1B. In addition a number of non-native modulators including antagonists, and agonists (as well as in some cases partial agonists and/or partial antagonists) have been identified for each of these QS systems. The present invention relates to certain combinations of modulators of Las, Rhl and Pqs which exhibit improved inhibition of virulence in comparison to the respective individual modulators. In specific embodiments, certain combinations of modulators exhibit such improved inhibition in nutritionally depleted (with respect to the bacterium) environments. In specific embodiments, certain combinations of modulators exhibit such improved inhibition in environments depleted in phosphate. In specific embodiments, certain combinations of modulators exhibit such improved inhibition in environments depleted in iron. In specific embodiments, nutrient depleted environments, mimic environments associated with bacterial infection in humans and non-human animals.

Combination of modulators includes chemically different modulators wherein the modulators affect the Las, Rhl or Pqs QS systems. In some cases, a given modulator in a combination may affect more than one QS system. In the case where a given modulator affects more than one QS system, the modulator will be designated based on the QS system for which it exhibits the highest level of effect. The effect of a given modulator on a given QS system may depend upon the level of nutrients, the carbon source or other components or conditions (e.g., pH) of the environment of the bacterium, where such environment can, for example, be an in vivo environment infected by the bacterium. Preferably, the combination contains chemically different modulators of two of Las, Rhl or Pqs. In specific embodiments, the combination of modulators is a combination of one or more antagonist of LasR with one or more antagonist of RhlR. In specific embodiments, the combination of modulators is a combination of one or more antagonist of LasR with one or more antagonist of PqsR. In specific embodiments, the combination of modulators is a combination of one or more antagonist of RhlR with one or more antagonist of PqsR. In specific embodiments, the relative molar amounts of the antagonist or the more than one antagonist of LasR and the antagonist or the more than one antagonist of RhlR in the combination ranges from 0.1 to 10. In specific embodiments, the relative molar amounts of the antagonist or the more than one antagonist of LasR and of the antagonist or the more than one antagonist of RhlR in the combination ranges from 0.5 to 5. In specific embodiments, the relative molar amounts of the antagonist or the more than one antagonist of LasR and the antagonist or the more than one antagonist of PqsR in the combination ranges from 0.1 to 10. In specific embodiments, the relative molar amounts of the antagonist or the more than one antagonist of LasR and the antagonist or the more than one antagonist of PqsR in the combination ranges from 0.5 to 5.

The invention also relates to a method for inhibiting quorum sensing in vivo or in vitro of a Gram-negative bacterium which has a plurality of QS systems employing contacting the bacterium or an environment containing the bacterium with a combination of small molecule modulators of two or more of the QS systems. In specific embodiments, the small molecule modulators of the QS systems exclude the native activators of the QS systems. In a specific embodiment, inhibiting quorum sensing inhibits virulence and the plurality of QS systems together control virulence of the bacterium. In a specific embodiment, inhibiting quorum sensing inhibits biofilm formation and the plurality of QS systems modulate biofilm formation in the bacterium. In a specific embodiment, the QS systems of the Gram-negative bacterium include at least one QS system which is mediated in nature by an N-acylhomoserine lactone signal molecule (i.e., the native activator of the QS system is an N-acylhomoserine lactone). In a specific embodiment, activity of the modulators of one or more of the multiple QS systems of the bacterium exhibits a dependence upon the environment of the bacterium. In specific embodiments, the activity of the modulators of one or more of the multiple QS systems of the bacterium exhibits a dependence upon the levels of nutrients in the environment of the bacterium. In specific embodiments, the activity of the modulators of one or more of the multiple QS systems of the bacterium exhibits a dependence upon the levels of phosphate in the environment of the bacterium. In specific embodiments, the activity of the modulators of one or more of the multiple QS systems of the bacterium exhibits a dependence upon the levels of iron in the environment of the bacterium.

In specific embodiments, the Gram-negative bacterium has three or more QS systems each of the systems having a different receptor and more specifically has three or more such QS systems exhibiting interaction among at least two of the systems. In an embodiment, the combination of small molecule modulators is a combination of two or more antagonists of different QS receptors of the QS system. In specific embodiments, the QS system of the bacterium has at least one QS system having a LuxR-type receptor and at least a second QS system having a receptor other than a LuxR-type receptor. In specific embodiments, the QS system of the bacterium has at least two QS systems each having a LuxR-type receptor and at least a third QS system having a receptor other than a LuxR-type receptor. In specific embodiments, the Gram-negative bacterium is of the family Pseudomonadacae. In specific embodiments, the Gram-negative bacterium is a species of the genus *Pseudomonas*. In specific embodiments, the Gram-negative bacterium is *Pseudomonas aeruginosa*. In specific embodiments, the *Pseudomonas* species is *P. putida*, or *P. syringae*. In specific embodiments, the Gram-negative bacterium is a species of the genus *Burkholderia*. In specific embodiments, the species of *Burkholderia* is *B. cepacia*, *B. pseudomallei*, or *B. mallei*.

The invention provides a method for treatment of an infection of a Gram-negative bacterium by inhibiting virulence in the bacterium employing a combination of two or more modulators each of which modulates a different QS system of the bacterium. In a specific embodiment, the method comprises the step of administering, to an individual in need of treatment for such infection, a combination of two or more small molecule antagonists of a QS system controlling virulence in the bacterium. More specifically, the two or more antagonists include one or more antagonists of one QS system of the bacterium and one or more antagonists of a second QS system of the bacterium. In a specific embodiment, activity of the modulators of one or more of the multiple QS systems of the bacterium exhibits a dependence upon the environment of the bacterium. In specific embodiments, the activity of the modulators of one or more of the multiple QS systems of the bacterium exhibits a dependence upon the levels of nutrients in the environment of the bacterium. In specific embodiments, the activity of the modulators of one or more of the multiple QS systems of the bacterium exhibits a dependence upon the levels of phosphate in the environment of the bacterium. In specific embodiments, the activity of the modulators of one or more of the multiple QS systems of the bacterium exhibits a dependence upon the levels of iron in the environment of the bacterium. In specific embodiments, the Gram-negative bacterium has three or more QS systems each of the systems having a different receptor and more specifically has three or more such QS systems exhibiting interaction among at least two of the systems. In an embodiment, the combination of small molecule modulators is a combination of two or more antagonists of different QS receptors of the QS system. In specific embodiments, the QS system of the bacterium has at least one QS system having a LuxR-type receptor and at least a second QS system having a receptor other than a LuxR-type receptor. In specific embodiments, the QS system of the bacterium has at least two QS systems each having a LuxR-type receptor and at least a third QS system having a receptor other than a LuxR-type receptor. In specific embodiments, the Gram-negative bacterium is of the species *Pseudomonas*. In specific embodiments, the Gram-negative bacterium is *Pseudomonas aeruginosa*.

In specific embodiments, the invention provides a method for treatment of an infection in an animal including a mammal and including a human of a Gram-negative bacterium by inhibiting virulence in the bacterium employing a combination of two or more modulators, each of which modulates a different QS system of the bacterium. In another specific embodiment, the infection is an infection of a combination of bacteria at least one of which has multiple QS systems. In another specific embodiment, the infection is an infection of a combination of species of bacteria of the genus *Pseudomonas* and *Burkholderia*. In a specific embodiment, the infection is an infection of the bacterium *P. aeruginosa*. In another specific embodiment, the infection is an infection of a combination of bacteria, including *P. aeruginosa*. In another specific embodiment, the infection is an infection of a combination of *P. aeruginosa* and *Burkholderia cepacia*. In specific embodiments, the infection is an infection of the lungs. In an embodiment, the infection is an infection of a burn wound. In an embodiment, the infection is an infection in an immune-compromised individual. In an embodiment, the infection is an infection in an individual with cystic fibrosis. In an embodiment, the infection is an infection in an individual with HIV.

The invention in addition provides a virulence inhibiting composition comprising two or more small molecule QS modulators, each of which modulates a different QS system of a selected Gram-negative bacterium. In a specific embodiment, the virulence inhibiting composition is a pharmaceutically acceptable composition. In a specific embodiment, the virulence inhibiting composition comprises the two or more small molecule QS modulators as active ingredients in combination with a pharmaceutically acceptable carrier.

Further aspects and embodiments of the invention will be apparent to one of ordinary skill in the art on consideration of the detailed description and examples.

BRIEF DESCRIPTION OF THE DRAWINGS

(FIG. 2A) Growth curves in complete MOPS/Glutamate. (FIG. 2B) Growth curves in complete MOPS/Glucose. (FIG. 2C) Growth curves in complete MOPS/Glutamate illustrating the growth delay caused by compound 3 and BHL. (FIG. 2D) Growth curves in SCFM2. *P. aeruginosa* (PAO1) was grown in a manner identical to the pyocyanin assay (see Experimental Procedures). At each time point, growth was measured by either reading $OD_{600}$ (for MOPS media) or by serially diluting culture aliquots, plating on LB agar, and counting CFUs after overnight incubation at 37° C. (for SCFM2). Compound concentrations are 100 microM for compounds 1, 2, and 3 and 25 microM for compound 4 in all experiments unless noted otherwise. Error bars represent the standard error of at least two biological replicates (n≥2). BHL=N-butyryl L-homoserine lactone (Cayman Chemicals).

(FIG. 6A) Single compound screens in MOPS minimal media. FIGS. 7A and 7B and FIGS. 1A-1D).

FIGS. 7A-7C illustrate *P. aeruginosa* growth curves in the presence of the RhlR agonist (compound 3). *P. aeruginosa* (PAO1) and an isogenic rhlR mutant were grown in (FIG. 7A) complete MOPS Glutamate medium (FIG. 7B) complete MOPS Glucose medium, or (FIG. 7C) LB broth treated with 100 µM compound 3. The $OD_{600}$ of the culture was measured at the indicated time points. Error bars indicate the standard error of at least two biological replicates (n≥2).

DETAILED DESCRIPTION OF THE INVENTION

Figure 1:
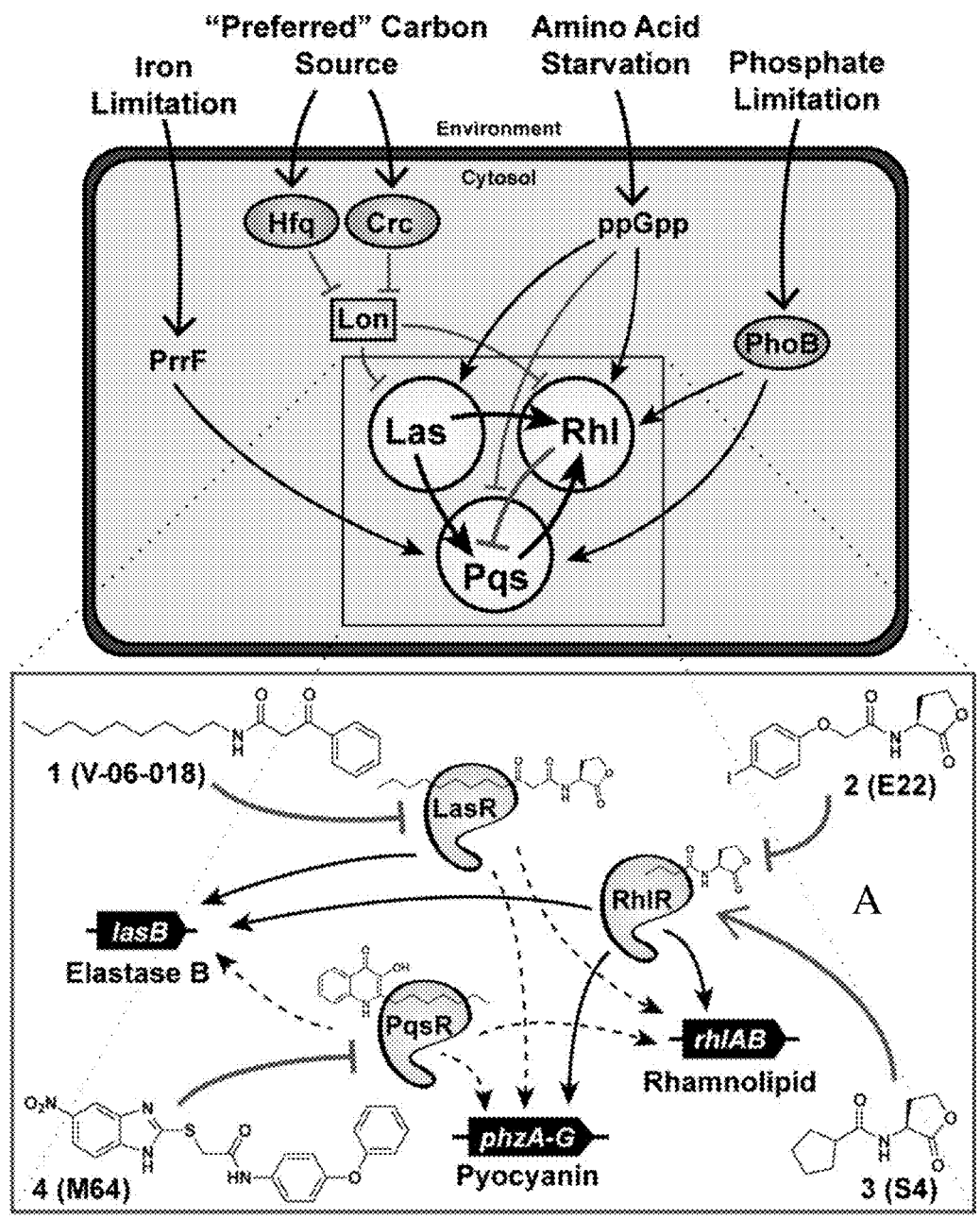
FIG. 1 illustrates the environmental cues that influence QS circuit activity and the regulation of select virulence factors in *P. aeruginosa*. Iron concentrations can activate the Pqs system indirectly through the regulatory RNA PrrF (Oglesby et al., 2008). Phosphate levels are known to activate Rhl and Pqs through the PhoR-PhoB two component system (Jensen et al., 2006). Carbon catabolite repression can influence QS activity through repression of Lon protease (Yang et al., 2015), a post-translational regulator of Las and Rhl. The stringent response differentially activates certain QS systems though ppGpp-binding transcription factors (Schafhauser et al., 2014). An enlarged view of the interaction of Las, Rhl and PqsR systemsis provide in panel A, showing in more detail the regulation of pyocyanin, rhamnolipid, and elastase B production by LasR, RhlR, and PqsR. Arrows with solid lines indicate direct, positive regulation, while arrows with dashed lines indicate positive regulation by indirect or unknown mechanisms. Small molecule QS probes used in this study include the LasR antagonist compound 1 (also called V-06-018) (Müh et al., 2006, Moore et al., 2015), the RhlR antagonist compound 2 (also called E22) (Welsh et al., 2015, Eibergen et al., 2015), the RhlR agonist compound 3 (also called S4) (Welsh et al., 2015), and the PqsR antagonist compound 4 (also called M64) (Starkey et al., 2014).
Figure 2A:
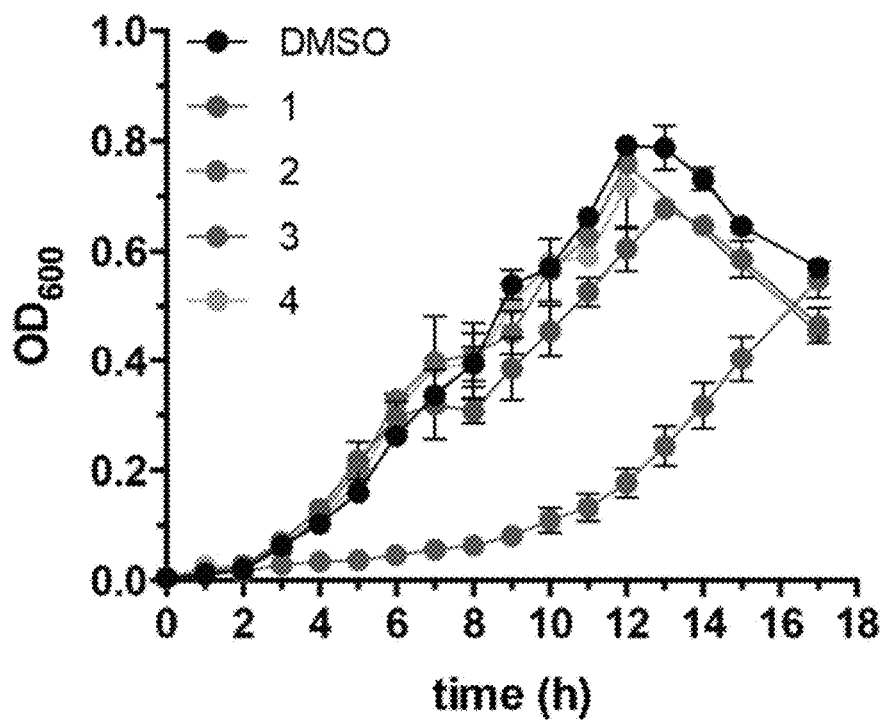
FIGS. 2A-2D are wild-type *P. aeruginosa* growth curves in the presence of test compounds in various media. Related to FIGS. 3, 6A and 6B, 7A and 7B, and 12.
Figure 2B:
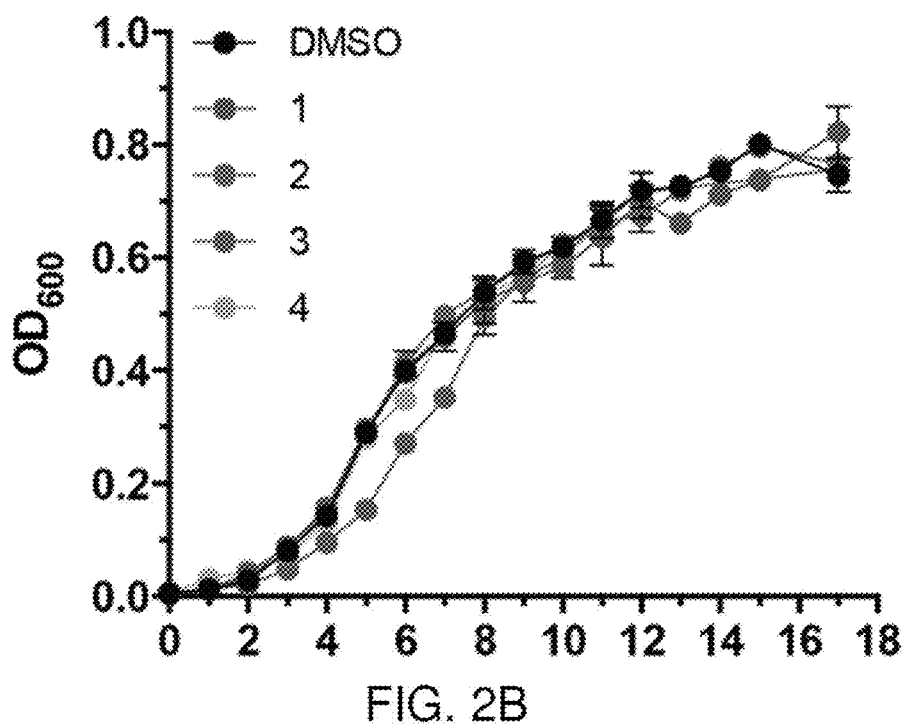
Figure 2C:
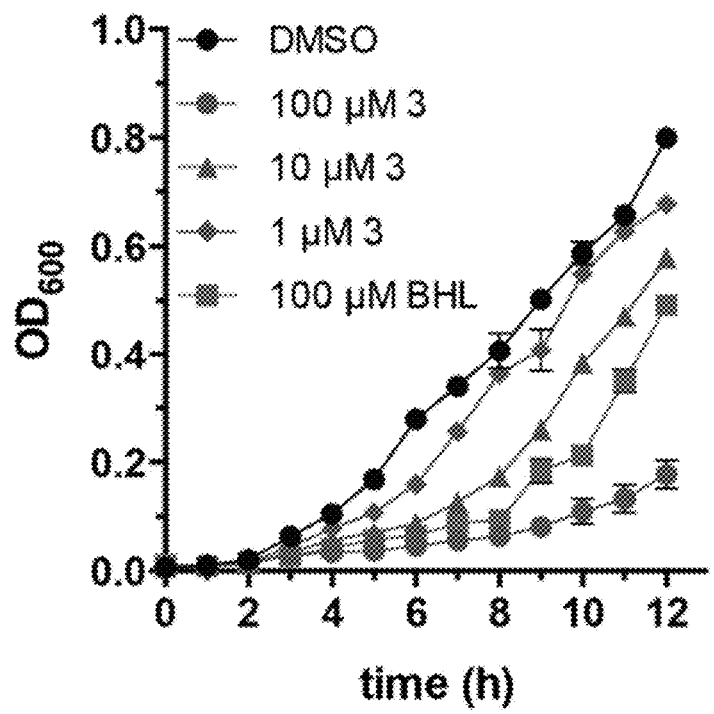
Figure 2D:
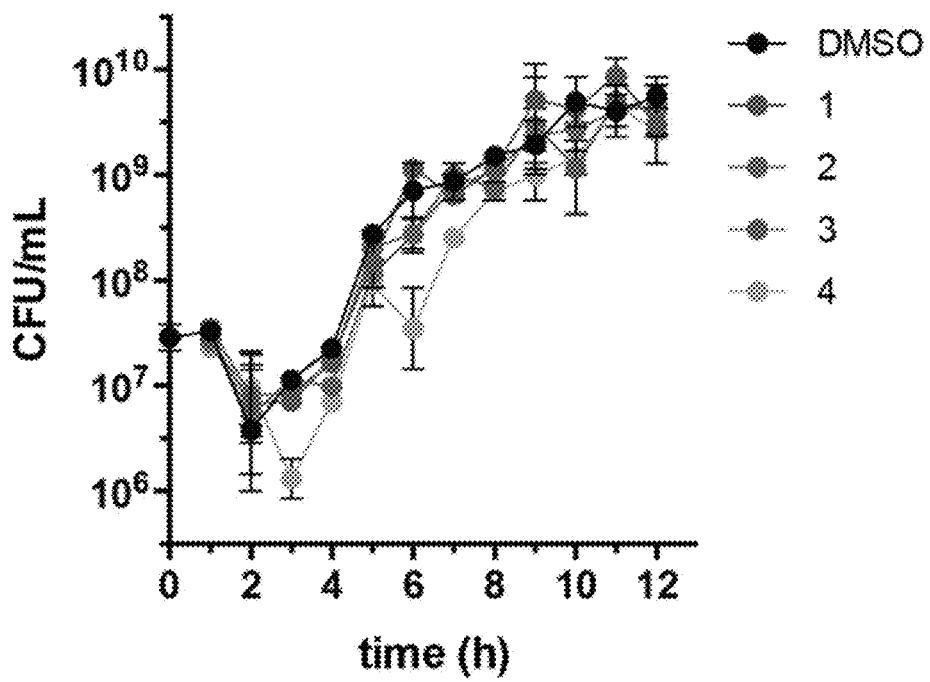

The invention relates to combinations of small molecule modulators of quorum sensing for inhibition of quorum sensing in bacteria. More specifically, the invention relates to combinations of small molecule inhibitors (antagonists) of the quorum sensing in bacteria having multiple quorum sensing systems wherein at least one of the quorum sensing systems is activated in nature by an acyl homoserine lactone, wherein the native activator or the quorum sensing system is an acyl homoserine lactone (AHL). Yet more specifically, the invention relates to combinations of quorum sensing modulators for inhibition of quorum sensing in *P. aeruginosa*.

Bacteria can have multiple quorum sensing systems which are distinct. Distinct quorum sensing systems are defined by having distinct proteins involved in regulation of quorum sensing and distinct molecules which activate a given quorum sensing system. A compound which is a modulator of a selected quorum sensing system in a given bacterium (e.g., LasR, RhlR or PqsR in *Pseudomonas*) may exhibit some level of activity as a modulator of a different quorum sensing system in that bacterium. For example, a given modulator, particularly a synthetic non-native small molecule may acts as an inhibitor of RhlR and an agonist of LasR. More specifically, a compound which is an inhibitor of one quorum sensing system may also inhibit other quorum sensing systems in the same bacterium. The relative amount of inhibition (or activation) that a given compound exhibits for each quorum sensing system in a bacterium can be assessed, for example, as demonstrated in Welsh et al., 2015; Moore et al., 2015 and Eibergen et al., 2015 by determining the relative levels of antagonism or agonism exhibited by a given compound with respect to different quorum sensing systems present in a bacterium. The text and supplemental information for each of these references is incorporated by reference herein in its entirety at least for assay methods for determining relative levels of antagonism and agonism of a given compound for a given quorum sensing system, as well as to provide additional strucutres of QS modulators.

The terms "inhibitor" and "anatagonist" are used interchangeably herein. The terms "activator" and "agonist" are used interchangeably herein.

In the combinations of quorum sensing modulators of the present invention, a given compound is defined as an antagonist or agonist of a given quorum sensing system based on the quorum sensing system for which it exhibits the highest level of antagonism or agonism in a given bacterium. For use in the methods of this invention, modulators which exhibit selective inhibition or selective agonism of a given quorum sensing system in a given bacterium are preferred. A selective inhibitor (antagonist) of a quorum sensing system, exhibits 60% or higher antagonism of the quorum sensing system for which it is selective and exhibits 40% or less antagonism of other quorum sensing systems in the bacterium. A selective agonist of a quorum sensing system, exhibits 60% or higher agonism of the quorum sensing system for which it is selective and exhibits 40% or less agonism of other quorum sensing systems in the bacterium.

Percent agonism of a given non-native inducer in a given bacterium and QS system receptor is measured with resepct to the maximum level of agonism (activation) by the native ligand of that receptor in the given bacterium. Percent antagonism is measured in competitive assays. The QS system of interest is activated to 100% with added or endogenous native ligand and the % antagonism of the non-native inducer is assessed with respect to 100% activation by the native inducer. The native ligand which induces LasR is OdDHL, which induces RhlR is BHL and which induces PqsR is PQS. As described herein and in cited references, assays for assessment of % agonism or % atangonism may be performed in $E.$ $coli$ systems (heterologous) or in the bacterium of interest, e.g., $Pseudomonas$. Dependent upon the assay system employed native ligand may be endogenously present or it may be exogenously supplied to the assay system. For antagonism assays in $E.$ $coli$ (heterologous strains that do not produce the native ligand or receptor), native ligand is added from about 10-100× the $EC_{50}$ of the native ligand for the given QS receptor to maximally activate the system. In antagonism assays using the native strains with functional QS systems, e.g., those of $P.$ $aeruginosa$, endogenous native ligand is made in the system, so no native ligand is added. In native strains having one or more non-functional QS systems (mutant strains), e.g., $P.$ $aeruginosa$ mutants with non-functional QS systems, native ligand is added at about 10-100× the $EC_{50}$ of the native ligand. In the agonism assay, native ligand is added as a control. Details of the assays are provided herein in Example 9 and in references cited in Example 9.

Agonism and antagonism assays can be performed in at least three types of systems, a heterologous system, such as in $E.$ $coli$ which does not have the endogenous QS systems, a native QS bacterium having multiple QS systems which interact, such as native $P.$ $aeruginosa$, or in mutants of the native strain in which one or more of the QS systems are inactive, as in mutant $P.$ $aeruginosa$ strains. In the $E.$ $coli$ system or a mutant system, compound activity can be assessed in one or more QS system at a time. In the native background, compound activity can be assessed with the systems working together determining how the compound impacts the interacting QS network. In an embodiment, percent agonism and antagonism is accessed in a heterologous or appropriate mutant system to determine QS activity with respect to a given QS receptor in the absence of other QS receptors.

A selective antagonist of a given quorum sensing system may exhibit agonism above control levels with respect to another quorum sensing system in the bacterium, but preferably does not. A selective agonist of a given quorum sensing system may exhibit antagonism above control levels with respect to another quorum sensing system in the bacterium; but preferably does not.

A more preferred selective inhibitor of a given quorum sensing system exhibits less than 30% antagonism of a quorum sensing system other than the quorum sensing system for which it is selective in the bacterium. A yet more preferred selective inhibitor of a given quorum sensing system exhibits less than 20% antagonism of a quorum sensing system other than the quorum sensing system for which it is selective in the bacterium. A yet more preferred selective inhibitor of a given quorum sensing system exhibits less than 10% antagonism of a quorum sensing system other than the quorum sensing system for which it is selective in the bacterium. A yet more preferred selective inhibitor of a given quorum sensing system exhibits equal to or less than 5% antagonism of another quorum sensing system in the bacterium. A more preferred selective inhibitor of a given quorum sensing system exhibits less than 30% agonism of a quorum sensing system other than the quorum sensing system for which it is selective in the bacterium. A yet more preferred selective inhibitor of a given quorum sensing system exhibits less than 20% agonism of a quorum sensing system other than the quorum sensing system for which it is selective in the bacterium. A yet more preferred selective inhibitor of a given quorum sensing system exhibits less than 10% agonism of a quorum sensing system other than the quorum sensing system for which it is selective in the bacterium. A yet more preferred selective inhibitor of a given quorum sensing system exhibits equal to or less than 5% agonism of another quorum sensing system in the bacterium.

A more preferred selective agonist of a given quorum sensing system exhibits less than 30% agonism of another quorum sensing system in the bacterium. A yet more preferred selective agonist of a given quorum sensing system exhibits less than 20% agonism of another quorum sensing system in the bacterium. A more preferred selective agonist of a given quorum sensing system exhibits less than 10% agonism of another quorum sensing system in the bacterium. A more preferred selective agonist of a given quorum sensing system exhibits equal to or less than 5% agonism of another quorum sensing system in the bacterium. A more preferred selective agonist of a given quorum sensing system exhibits less than 30% antagonism of another quorum sensing system in the bacterium. A yet more preferred selective agonist of a given quorum sensing system exhibits less than 20% antagonism of another quorum sensing system in the bacterium. A more preferred selective agonist of a given quorum sensing system exhibits less than 10% antagonism of another quorum sensing system in the bacterium. A more preferred selective agonist of a given quorum sensing system exhibits equal to or less than 5% antagonism of another quorum sensing system in the bacterium.

In specific embodiments, a more preferred selective inhibitor exhibits 60% or higher antagonism of the quorum sensing system for which it is selective, exhibits 30% or less antagonism of other quorum sensing systems in the bacterium and exhibits less than 30% agonism of other quorum sensing systems in the bacterium. In specific embodiments, a more preferred selective inhibitor exhibits 60% or higher antagonism of the quorum sensing system for which it is selective, exhibits 20% or less antagonism of other quorum sensing systems in the bacterium and exhibits less than 20% agonism of another quorum sensing system in the bacterium. In specific embodiments, a more preferred selective inhibitor exhibits 60% or higher antagonism of the quorum sensing system for which it is selective, exhibits 20% or less antagonism of other quorum sensing systems in the bacterium and exhibits less than 20% agonism of another quorum sensing system in the bacterium. In specific embodiments, a more preferred selective inhibitor exhibits 60% or higher antagonism of the quorum sensing system for which it is selective, exhibits 20% or less antagonism of other quorum sensing systems in the bacterium and exhibits less than 20% agonism of another quorum sensing system in the bacterium. In specific embodiments, a more preferred selective inhibitor exhibits 60% or higher antagonism of the quorum sensing system for which it is selective, exhibits 10% or less antagonism of other quorum sensing systems in the bacterium and exhibits less than 10% agonism of another quorum sensing system in the bacterium.

In specific embodiments, a more preferred selective inhibitor exhibits 70% or higher antagonism of the quorum sensing system for which it is selective, exhibits 40% or less antagonism of other quorum sensing systems in the bacterium and exhibits less than 30% agonism of other quorum sensing systems in the bacterium. In specific embodiments, a more preferred selective inhibitor exhibits 70% or higher antagonism of the quorum sensing system for which it is selective, exhibits 30% or less antagonism of other quorum sensing systems in the bacterium and exhibits less than 30% agonism of another quorum sensing system in the bacterium. In specific embodiments, a more preferred selective inhibitor exhibits 70% or higher antagonism of the quorum sensing system for which it is selective, exhibits 20% or less antagonism of other quorum sensing systems in the bacterium and exhibits less than 20% agonism of another quorum sensing system in the bacterium. In specific embodiments, a more preferred selective inhibitor exhibits 60% or higher antagonism of the quorum sensing system for which it is selective, exhibits 10% or less antagonism of other quorum sensing systems in the bacterium and exhibits less than 10% agonism of another quorum sensing system in the bacterium.

In specific embodiments, a more preferred selective inhibitor exhibits 80% or higher antagonism of the quorum sensing system for which it is selective, exhibits 40% or less antagonism of other quorum sensing systems in the bacterium and exhibits less than 30% agonism of another quorum sensing system in the bacterium. In specific embodiments, a more preferred selective inhibitor exhibits 80% or higher antagonism of the quorum sensing system for which it is selective, exhibits 30% or less antagonism of other quorum sensing systems in the bacterium and exhibits less than 30% agonism of another quorum sensing system in the bacterium. In specific embodiments, a more preferred selective inhibitor exhibits 80% or higher antagonism of the quorum sensing system for which it is selective, exhibits 20% or less antagonism of other quorum sensing systems in the bacterium and exhibits less than 20% agonism of another quorum sensing system in the bacterium. In specific embodiments, a more preferred selective inhibitor exhibits 80% or higher antagonism of the quorum sensing system for which it is selective, exhibits 10% or less antagonism of other quorum sensing systems in the bacterium and exhibits less than 10% agonism of another quorum sensing system in the bacterium.

Percent antagonism and percent agonism is assessed in assay systems described in Example 9 and in Eibergen et al. 2015.

In a specific embodiment, preferred selective RhlR-agonist are at least 2.5-fold more active in RhlR agonism assays than they are in LasR and QscR agonism assays. In a specific embodiment, preferred selective RhlR antagonists are at least 2.5-fold more active in RhlR agonism assays than they are in LasR and QscR agonism assays In specific embodiments of the above, the selective inhibitor is a LasR inhibitor which is selective with respect to inhibition of RhlR and PqsR and is selective with respect to activation (agonism) of RhlR and PqsR. In specific embodiments of the above, the selective inhibitor is an RhlR inhibitor which is selective with respect to inhibition of LasR and PqsR and is selective with respect to activation (agonism) of LasR and PqsR. In specific embodiments of the above, the selective inhibitor is a PqsR inhibitor which is selective with respect to inhibition of LasR and RhlR and is selective with respect to activation (agonism) of LasR and RhlR.

In specific embodiments, inhibitors of LasR, RhlR and PqsR are employed in the combination of the invention. In specific embodiments, selective inhibitors of LasR, RhlR and PqsR are employed in the combination of the invention.

LasR antagonists of the invention include those of formula I:

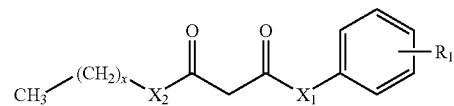

where:
x is an integer ranging from 3 to 15 inclusive;
$R_1$ represents 5 hydrogens on the indicated ring or 1-5 non-hydrogen substituents on the ring, where non-hydrogen substituents are selected from halogen, alkyl having 1-3 carbon atoms, alkoxy having 1-3 carbon atoms, haloalkyl having 1-3 carbon atoms, haloalkoxy having 1-3 carbon atoms, and nitro; and
$X_1$ and $X_2$, independently, are a single bond, —NH— or —S—,
wherein at least one of $X_1$ and $X_2$ is —NH— or —S—.

In specific embodiments, $X_1$ is —NH— and $X_2$ is —S—.

In specific embodiments, $R_1$ represents substitution on the ring of a non-hydrogen substituent in the meta position on the indicated ring.

LasR antagonists of the invention include those of formula IA:

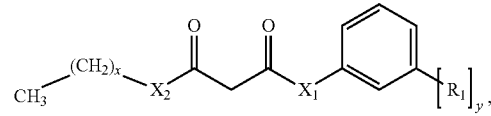

where:
x is an integer ranging from 3 to 15 inclusive;
y is 0 or 1, to show the absence or presence of the —$R_1$ group;
$R_1$ is an unsubstituted alkoxy group having 1-3 carbon atoms or is a halogen; and
$X_1$ and $X_2$, independently, are a single bond, —S— or —NH—;
wherein at least one of $X_1$ and $X_2$ is —S— or —NH—.

LasR antagonists of the invention include those of formula IB or IC:

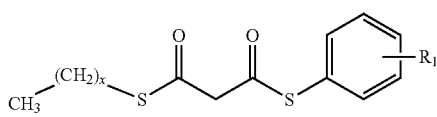

1B

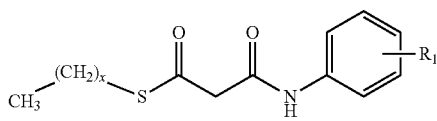

1C where $R_1$ and x are as defined for formula I.

In specific embodiments of formulas I and IA-IC, x is 7-10 and in further specific embodiments, x is 7, or 8, or 9, or 10. In specific embodiments, one of $X_1$ or $X_2$ is NH. In specific embodiments of formulas I and IA-IC, both of $X_1$ and $X_2$ are NH. In specific embodiments of formulas I, IB and IC, $R_1$ represents substitution on the indicated ring with at least one non-hydrogen substituent in the meta-position. In specific embodiments of formulas IA-IC, $R_1$ represents hydrogen(s).

In specific embodiments of formula IA, y is 1. In specific embodiments of formula IA, y is 1 and $R_1$ is an alkoxy group. In specific embodiments of formula IA, y is 1 and $R_1$ is —O—$CH_3$. In specific embodiments of formula IA, y is 1 and $R_1$ is I.

More specifically, LasR antagonists of the invention include those of formula ID:

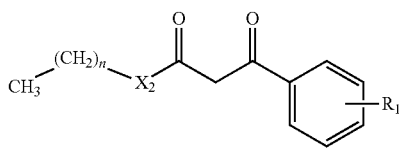

formula IE:

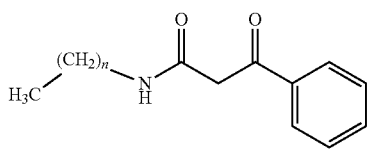

where:
n is an integer ranging from 3 to 15 inclusive;
$X_2$ in formula ID is —$R_1$ represents 5 hydrogens on the indicated ring or 1-5 non-hydrogen substituents on the ring, where non-hydrogen substituents are selected from halogen, alkyl having 1-3 carbon atoms, alkoxy having 1-3 carbon atoms, haloalkyl having 1-3 carbon atoms, haloalkoxy having 1-3 carbon atoms, and nitro.

In specific embodiments of formulas ID and IE, n is 7-10 and in further specific embodiments, n is 7, or 8, or 9, or 10. In a preferred embodiment, the LasR antagonist is the compound of formulas ID or IE where n is 8.

With respect to compounds of formula IA-ID, US 2009/0123512 (Müh et al.) and Müh et al. (2006) are each incorporated by reference herein in its entirety for methods of synthesis of such compounds and for additional examples of such compounds. These references further provide additional information on activity of compounds therein as inhibitors of quorum sensing. Certain of the compounds of the formulas I and IA-IE can be prepared in view of the above references and in view of well-known synthetic methods.

LasR antagonists of the invention include those of formula IF:

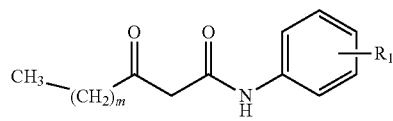

where:
m is an integer from 3 to 13 inclusive and
$R_1$ represents 5 hydrogens on the indicated ring or 1-5 non-hydrogen substituents on the ring, where non-hydrogen substituents are selected from halogen, alkyl having 1-3 carbon atoms, alkoxy having 1-3 carbon atoms, haloalkyl having 1-3 carbon atoms, haloalkoxy having 1-3 carbon atoms, and nitro.

In specific embodiments of formula IF, m is 7-10 and in further specific embodiments, m is 7, or 8, or 9, or 10. In a preferred embodiment, the LasR antagonist is the compound of formula IF where m is 8 and R1 represents 5 hydrogens. In specific embodiments, $R_1$ represents substitution on the indicated ring of one or more, preferably 1 or 2 halogens. In specific embodiments, $R_1$ represents substitution on the indicated ring of one or more, preferably 1 or 2 alkoxy groups. In specific embodiments, $R_1$ represents substitution on the indicated ring of an ortho or para alkoxy group. A preferred alkoxy group is methoxy.

With respect to compounds of formula IF, McInnis and Blackwell, 2011 and Morkunas et al., 2012 are each incorporated by reference herein in its entirety for sources of compounds, methods of synthesis of such compounds and for additional examples of such compounds. These references further provide additional information on activity of compounds therein as inhibitors of quorum sensing. Certain of the compounds of the formula IF can be prepared in view of the above references and in view of well-known synthetic methods.

LasR antagonists of the invention include those of formula IG:

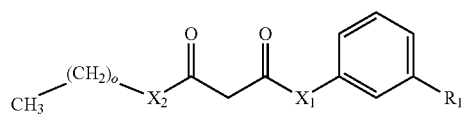

where o is an integer ranging from 3-15, inclusive;

$X_1$ and $X_2$, independently, are a single bond or NH;

wherein at least one of $X_1$ and $X_2$ is NH; and $R_1$ is a halogen or an unsubstituted alkyl group having one to 3 carbon atoms.

In specific embodiments, $R_1$ is an unsubstituted alkoxy group having 1-3 carbon atoms. In specific embodiments, $R_1$ is a methoxy group. In specific embodiments, $R_1$ is a halogen. In specific embodiments, $R_1$ is an iodine. In specific embodiments, $X_1$ is NH and $X_2$ is a single bond. In specific embodiments, $X_2$ is NH and $X_1$ is a single bond.

With respect to compounds of formula IG, Hodgkinson et al., 2012 is incorporated by reference herein in its entirety for methods of synthesis of such compounds and for additional examples of such compounds. These references further provide additional information on activity of compounds therein as inhibitors of quorum sensing.

LasR antagonists of the invention include those of formula II:

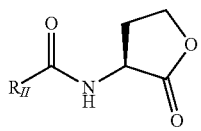

where $R_{II}$ is selected from unsubstituted alkyl having 5 to 8 carbon atoms; or $R_{II}$ is selected from:

$R_{AR}$—(CH$_2$)$_p$—, where p is an integer ranging from 1 to 3, inclusive, and $R_{AR}$ is an unsubstituted phenyl group;

$R_{AR}$—(CH$_2$)$_q$—CO—, where q is an integer ranging from 1 to 3 and $R_{AR}$ is an unsubstituted phenyl group, a phenyl group substituted with one or two halogens, one or two trihalomethyl groups or substituted with a combination thereof;

$R_{AR}$—O—(CH$_2$)$_r$—, where r is an integer ranging from 1 to 3 and $R_{AR}$ is an unsubstituted phenyl group; or $R_{AR}$—O—(CH$_2$)$_s$—CO—, where s is an integer ranging from 1 to 3, inclusive and $R_{AR}$ is an unsubstituted phenyl group, a phenyl group substituted with one or two halogens, one or two trihalomethyl groups or a phenyl ring substituted with a combination thereof; or In specific embodiments, LasR antagonists are compounds of formula II in which $R_{II}$ is selected an unsubstituted alkyl having 5 to 8 carbon atoms. More specifically, LasR antagonists include the compound of formula II where $R_{II}$ is an unsubstituted alkyl group having 6 carbon atoms (e.g., where $R_{II}$ is —C$_6$H$_{13}$). More specifically, LasR antagonists include the compounds of formula II, where $R_{II}$ is a straight chain unsubstituted alkyl group having 5-8 carbon atoms. In a specific embodiment, $R_{II}$ is n-hexyl.

In specific embodiments, LasR antagonists are compounds of formula II, where $R_{II}$ is $R_{AR}$—(CH$_2$)$_p$—, where p is an integer ranging from 1 to 3, inclusive, and $R_{AR}$ is an unsubstituted phenyl group. In specific embodiments, LasR antagonists are compounds of formula II, where p is 1. In specific embodiments, LasR antagonists are compounds of formula II where p is 2. In specific embodiments, LasR antagonists are compounds of formula II, where p is 3. In specific embodiments, LasR antagonists are compounds of formula II, where $R_{AR}$ is an unsubstituted phenyl group.

In specific embodiments, LasR antagonists are compounds of formula II, where $R_{II}$ is $R_{AR}$—(CH$_2$)$_q$—CO—, where q is an integer ranging from 1 to 3, inclusive, and $R_{AR}$ is an unsubstituted phenyl group, a phenyl group substituted with one or two halogens, one or two trihalomethyl groups or a phenyl group substituted with a combination of two or more halogens or trihalomethyl groups. In specific embodiments, LasR antagonists are compounds of formula II, where q is 1. In specific embodiments, LasR antagonists are compounds of formula II, where q is 2. In specific embodiments, LasR antagonists are compounds of formula II, where q is 3. In specific embodiments, LasR antagonists are compounds of formula II, where $R_{AR}$ is an unsubstituted phenyl group. In specific embodiments, LasR antagonists are compounds of formula II, where $R_{AR}$ is a p-Br substituted phenyl group. In specific embodiments, LasR antagonists are compounds of formula II, where $R_{AR}$ is a p-Cl substituted phenyl group. In specific embodiments, LasR antagonists are compounds of formula II, where $R_{AR}$ is a p-CF$_3$ substituted phenyl group.

In specific embodiments, LasR antagonists are compounds of formula II, where $R_{II}$ is $R_{AR}$—O—(CH$_2$)$_r$—, where r is an integer ranging from 1 to 3, inclusive, and $R_{AR}$ is an unsubstituted phenyl group. In specific embodiments, LasR antagonists are compounds of formula II, where r is 1. In specific embodiments, LasR antagonists are compounds of formula II, where r is 2. In specific embodiments, LasR antagonists are compounds of formula II, where r is 3. In specific embodiments, LasR antagonists are compounds of formula II, where $R_{AR}$ is an unsubstituted phenyl group.

In specific embodiments, LasR antagonists are compounds of formula II, where $R_{II}$ is $R_{AR}$—O—(CH$_2$)$_s$—CO—, where s is an integer ranging from 1 to 3, inclusive, and $R_{AR}$ is an unsubstituted phenyl group, a phenyl group substituted with one or two halogens, one or two trihalomethyl groups, or a phenyl group substituted with a combination of two or more halogens or trihalomethyl groups. In specific embodiments, LasR antagonists are compounds of formula II, where s is 1. In specific embodiments, LasR antagonists are compounds of formula II, where s is 2. In specific embodiments, LasR antagonists are compounds of formula II, where s is 3. In specific embodiments, LasR antagonists are compounds of formula II, where $R_{AR}$ is an unsubstituted phenyl group. In specific embodiments, LasR antagonists are compounds of formula II, where $R_{AR}$ is a p-Br substituted phenyl group. In specific embodiments, LasR antagonists are compounds of formula II, where $R_{AR}$ is a p-Cl substituted phenyl group. In specific embodiments, LasR antagonists are compounds of formula II, where $R_{AR}$ is a p-CF$_3$ substituted phenyl group.

With respect to compounds of formula II, Geske et al. (2007) and Zhu et al. (1998) are each incorporated by reference herein in its entirety for methods of synthesis of such compounds and for additional examples of such compounds. These references further provide additional information on activity of compounds therein as inhibitors of quorum sensing.

LasR antagonists include those of formula III:

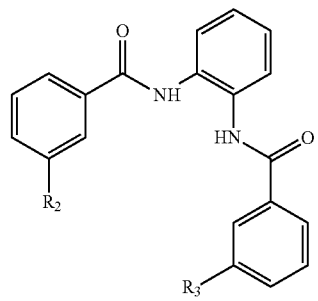

where:

$R_2$ and $R_3$ are independently halogens.

In specific embodiments, one of $R_2$ and $R_3$ is a chlorine. In specific embodiments, $R_2$ and $R_3$ are both chlorine. In specific embodiments, $R_2$ and $R_3$ are both fluorine. In specific embodiments, $R_2$ and $R_3$ are both bromine. In specific embodiments, $R_2$ and $R_3$ are both iodine.

With respect to compounds of formula III, Müh et al., 2006 is incorporated by reference herein in its entirety for sources of compounds, methods of synthesis of such compounds and for additional examples of such compounds. These references further provide additional information on activity of compounds therein as inhibitors of quorum sensing.

LasR antagonists include those of formula IIIA:

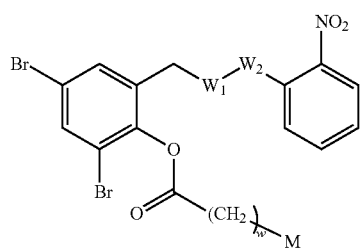

where one of $W_1$ or $W_2$ is —CO— and the other of $W_1$ or $W_2$ is —NH—;
w is 1, 2 or 3 and
M is —NH—CO—$R_{20}$ or

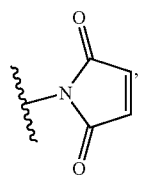

where $R_{20}$ is —CO—$(CH_2)_v$Cl, where v is 1 or 2, preferably 1.

In a specific embodiment, W1-W2 is —NH—CO—.
In a specific embodiment the compound of formula IIIA is:

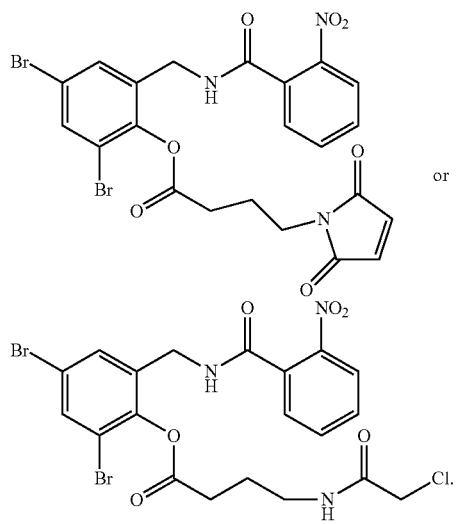

With respect to the above compounds of formula IIIA, O'Brien, et al. 2015 and the corresponding supporting information for the reference, which is available to the public on line at the American Chemical Society Publications web site are each incorporated by reference herein for methods of synthesis of such compounds and for additional examples of such compounds. These references further provide additional information on activity of compounds therein as inhibitors of quorum sensing.

Additional LasR inhibitors have formula IIIB:

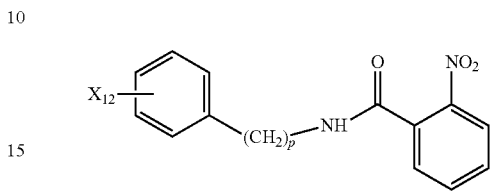

where:
p is 1 or 2 and
$X_{12}$ represents substitution of the indicated ring with one or two halogens at the ortho, meta or para-positions of the ring or one nitro group at the ortho-position of the rings. Compounds of formula IIIB are among compounds described in O'Reilly and Blackwell, 2015 and supporting information thereof, which is available to the public on-line from the American Chemical Society publications website. This reference and supporting material is incorporated by reference herein in its entirety for QS compounds therein and the descriptions therein of compound synthesis and activity.

In specific embodiments, $X_{12}$ represents substitution with one Cl, Br or I at the para-position on the indicated ring. In specific embodiments, $X_{12}$ represents substitution with one Cl, Br or I at the meta-position on the indicated ring. In specific embodiments, $X_{12}$ represents substitution with two fluorines or two chlorines on the ring. In specific embodiments, $X_{12}$ represents substitution with one Br at the para-position on the indicated ring. In specific embodiments, $X_{12}$ represents substitution with one Br at the meta-position on the indicated ring. In specific embodiments, $X_{12}$ represents substitution with one Cl at the para-position on the indicated ring. In specific embodiments, $X_{12}$ represents substitution with one Cl at the meta-position on the indicated ring.

O'Reilly and Blackwell, 2015 provides description of the synthesis and QS activity of compounds of formula IIIB. Compounds of formula IIIB can be prepared by one of ordinary skill in the art in view of the descriptions herein and what is generally known in the art.

In specific embodiments of the forgoing embodiments of formula IIIB, p is 2. In specific embodiments of the forgoing embodiments of formula IIIB, p is 1.

In specific embodiments, the LasR inhibitor is (compound 1, V-06-018)

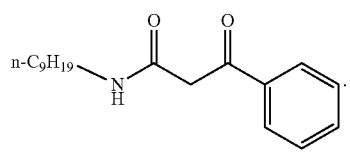

In specific embodiments, the LasR inhibitor is:

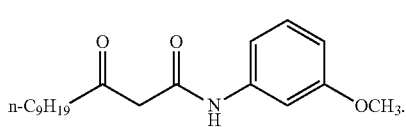

In specific embodiments, the LasR inhibitor is:

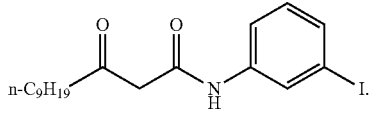

In specific embodiments, the LasR inhibitor is

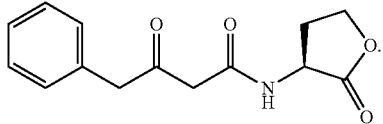 [SMILES: O=C(CC(=O)N[C@H]1CCOC1=O)Cc1ccccc1]

In specific embodiments, the LasR inhibitor is

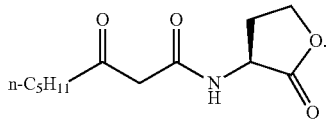

In specific embodiments, the LasR inhibitor is

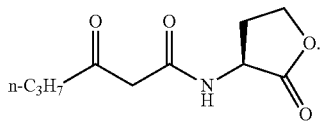

In specific embodiments, the LasR inhibitor is

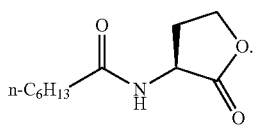

In specific embodiments, the LasR inhibitor is

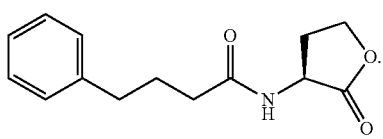 [SMILES: O=C(CCCc1ccccc1)N[C@H]1CCOC1=O]

In specific embodiments, the LasR inhibitor is

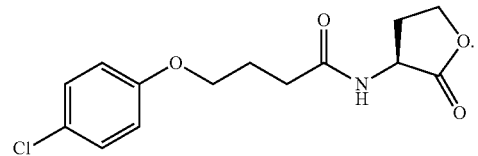 [SMILES: O=C(CCCOc1ccc(Cl)cc1)N[C@H]1CCOC1=O]

In specific embodiments, the LasR inhibitor is

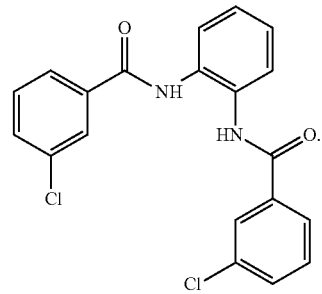 [SMILES: O=C(Nc1ccccc1NC(=O)c1cccc(Cl)c1)c1cccc(Cl)c1]

In specific embodiments, the LasR inhibitor is

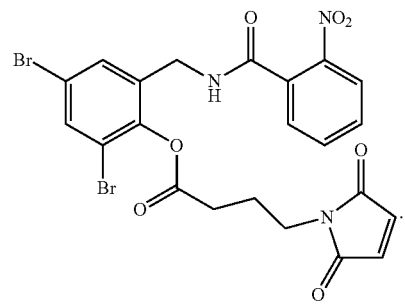 [SMILES: O=C(CCCN1C(=O)C=CC1=O)Oc1c(Br)cc(Br)cc1CNC(=O)c1ccccc1[N+](=O)[O-]]

In specific embodiments, the LasR inhibitor is

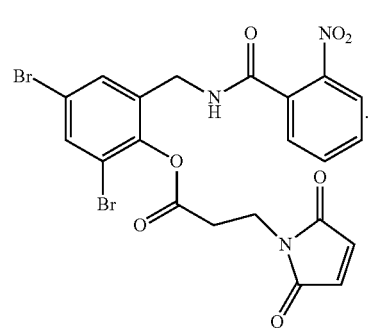 [SMILES: O=C(CCN1C(=O)C=CC1=O)Oc1c(Br)cc(Br)cc1CNC(=O)c1ccccc1[N+](=O)[O-]]

In specific embodiments, the LasR inhibitor is

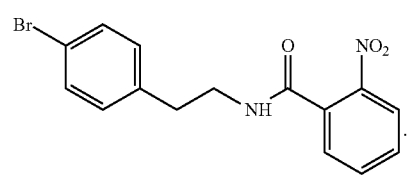 [SMILES: O=C(NCCc1ccc(Br)cc1)c1ccccc1[N+](=O)[O-]]

In specific embodiments, the LasR inhibitor is

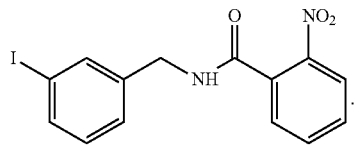

In specific embodiments, the LasR inhibitor is

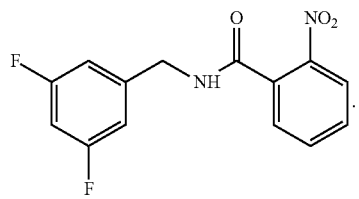 [SMILES: O=C(NCc1cc(F)cc(F)c1)c1ccccc1[N+](=O)[O-]]

In specific embodiments, the LasR inhibitor is:

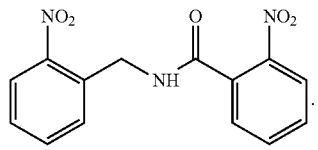 [SMILES: O=C(NCc1ccccc1[N+](=O)[O-])c1ccccc1[N+](=O)[O-]]

Moore et al., 2015, and the corresponding supporting information, which is available to the public on-line from the American Chemical Society publications website, are incorporated by reference herein for descriptions of LasR antagonists and various phenotypic responses induced by such antagonists. Moore et al. 2015, Table S2 of the supporting information, cites the following references for descriptions of quorum sensing modulators listed in the table: Amara et al., 2009; Chen et al., 2011; Costas et al. 2015; Geske et al., 2005; Geske et al. 2007; Geske et al., 2008a; Hentzer et al., 2003; Hodgkinson et al., 2012; Ishida, et al., 2007; McInnes et al., 2011; Morkunas et al., 2012; Muh et al., 2006 (a); Muh, et al., 2006 (b); O'Loughlin et al., 2013; Persson et al., 2005; Reverchon et al., 2002; Smith et al., 2003(a); Smith et al., 2003(b); Swem et al. 2009; Wu, et al., 2004; Zakhari et al., 2011; and Zhu et al. 1998. Each of these references is incorporated by reference herein for descriptions of methods of synthesis, methods of assessment of quorum sensing modulation and comparative modulation data for a number of compounds that are useful in the present invention.

RhlR antagonists of the invention include those of formula IV:

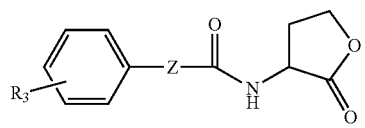

Formula IVA:

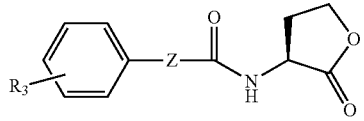

Figure 14:
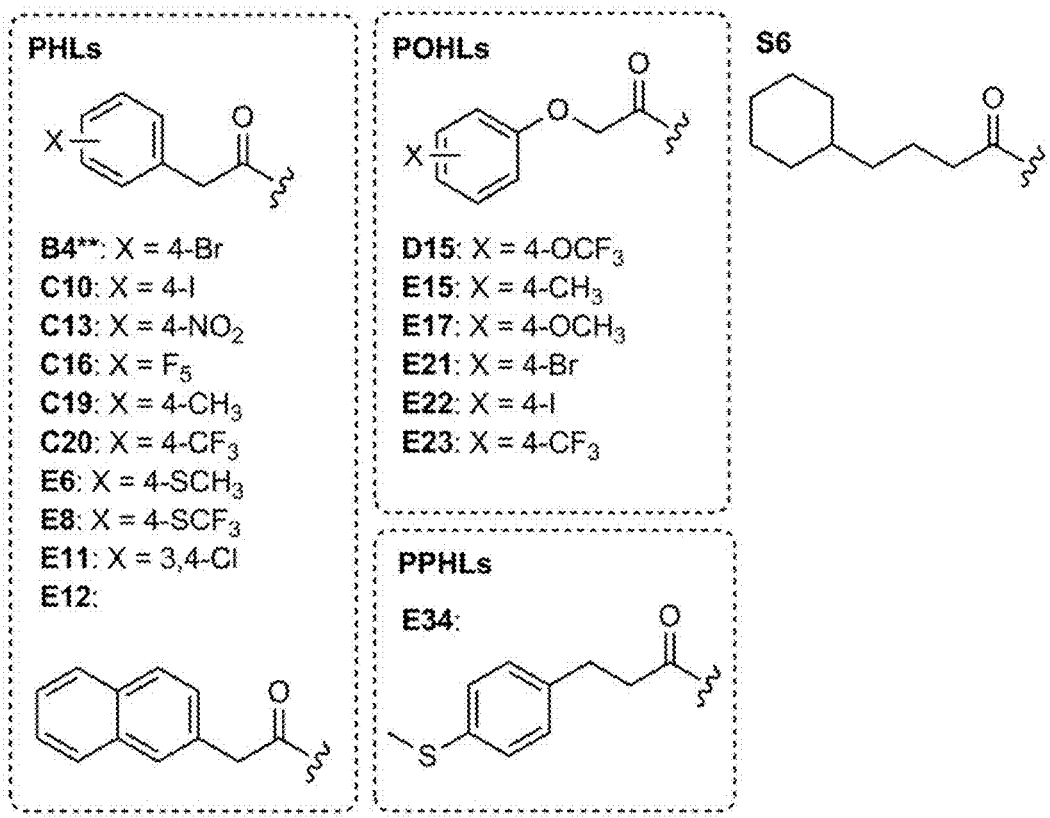
FIG. 14 provides a list and structures of exemplary RhlR antagonists.

Formula IVB:

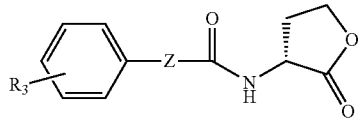

where:
Z is —CH$_2$—, —CH$_2$—CH$_2$—, —CH$_2$—CH$_2$—CH$_2$— or —O—CH$_2$—;
R$_3$ is one to five halogens, a 4-halogen, a 4-nitro, a 4-alkyl having one to three carbon atoms, a 4-alkoxy having one to three carbon atoms, a 4-fluoroalkyl having one to three carbon atoms; a 4-S-alkyl having one to three carbon atoms, a 4-S-fluoroalkyl having one to three carbon atoms, a 3, 4-dihalogen, or R$_3$ represents a fused five carbon ring which with the phenyl ring forms a naphthyl group. See RhlR antagonists of the PHL group and the PPHL group in FIG. 14.

With respect to compounds of formula IV, Eibergen et al., 2015 is incorporated by reference herein in its entirety for sources of compounds, methods of synthesis and additional information with respect to the activity of RhlR antagonists and RhlR selective antagonists. U.S. Pat. Nos. 7,910,622 and 8,815,943 are incorporated by reference herein for descriptions of structures of QS modulators and synthetic methods useful in the synthesis of compounds of this invention.

RhlR antagonists include those of formulas IVC, IVD and IVE:

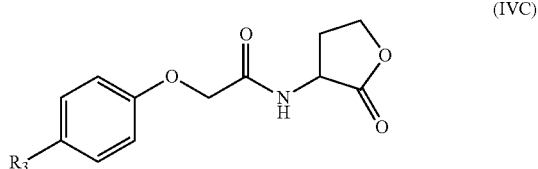
(IVC)

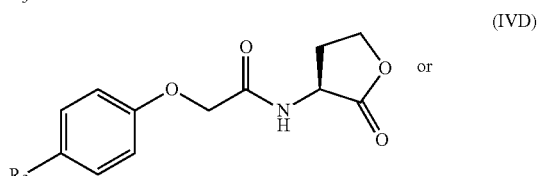
(IVD)

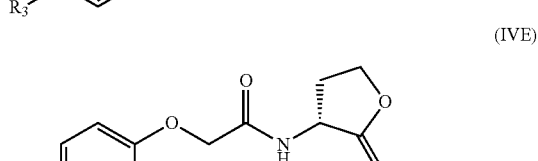
(IVE)

where:
R$_3$ is Br—, I—, CF$_3$—, or CF$_3$—S—. See exemplary RhlR antagonists of the POHL group in FIG. 14.

RhlR antagonists include those of formula V:

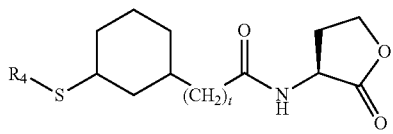

where:
t is an integer ranging from 1 to 3, inclusive; and
$R_4$ is an unsubstituted alkyl group having 1-3 carbon atoms.

RhlR antagonists include those of formula VI:

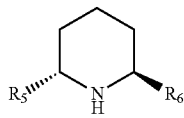

where
$R_5$ is an unsubstituted alkyl group having 6-16 carbon atoms; and
$R_6$ is an unsubstituted alkyl group having 1-3 carbon atoms.

In specific embodiments, $R_5$ is an unsubstituted alkyl group having 8-14 carbon atoms. In specific embodiments, $R_5$ is an unsubstituted alkyl group having 9-13 carbon atoms. In specific embodiments, $R_5$ is an unsubstituted alkyl group having 10-12 carbon atoms. In specific embodiments $R_5$ is an unsubstituted and straight-chain alkyl group. In specific embodiments, $R_6$ is an unsubstituted methyl group. In a specific embodiment, $R_6$ is an unsubstituted methyl group and $R_5$ is a straight-chain alkyl group having 9-13 carbon atoms. In a specific embodiment, $R_6$ is an unsubstituted methyl group and $R_5$ is a straight-chain alkyl group having 10-12 carbon atoms. In a specific embodiment, $R_5$ is a straight-chain alkyl group having 11 carbon atoms.

In specific embodiments, RhlR antagonists are compounds E22 (compound 2), E23, E21, E34, E11, E8, B4, C10:

(compound 2 (E22))

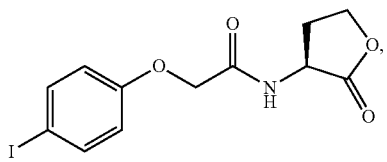

(E23)

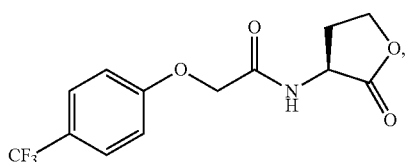

(E21)

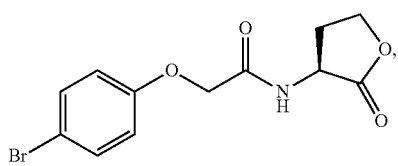

-continued (E34)

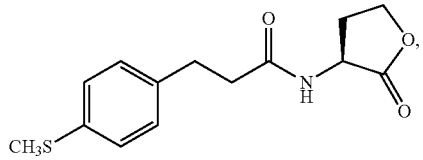

(E11)

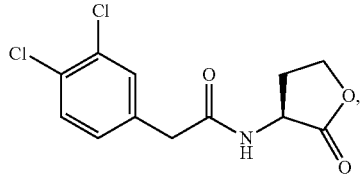

(E8)

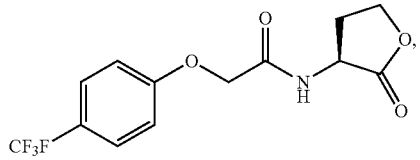

(C10)

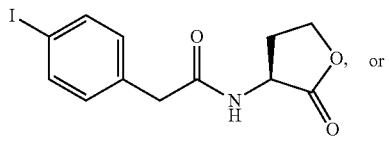

or (B4)

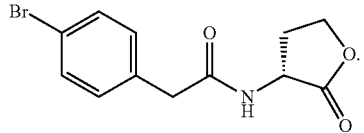

RhlR antagonists also include those of formula VII:

AII-L-W-HGII where:
—W— is —CO—NH—, —SO$_2$—NH—, —CO—NH—CH$_2$—, or —SO$_2$—NH—CH$_2$—;
L is —(CH$_2$)$_n$—, or —O—(CH$_2$)$_m$—, where n is 1, 2 or 3 and m is 1 or 2;
AII is selected from one or more of:
(1) a phenyl group substituted with one or more halogen, nitro group, alkyl group having 1-3 carbon atoms, haloalkyl group having 1-3 carbon atoms, an —O—R$_{II}$, and an —S—R$_{II}$ group, where R$_{II}$ is an alkyl or haloalkyl group having 1-3 carbon atoms;
(2) an optionally substituted naphthyl group; and
(3) in addition when L is —(CH$_2$)$_3$—, an optionally substituted cyclopentyl or cyclohexyl group,
where the groups of (2) or (3) are optionally substituted with one or more halogen, nitro group, alkyl group having 1-3 carbon atoms, haloalkyl group having 1-3 carbon atoms, an —O—R$_{II}$, and an —S—R$_{II}$ group, where R$_{II}$ is an alkyl or haloalky group having 1-3 carbon atoms; and
HGII is a cyclic group other than AHL of formula:

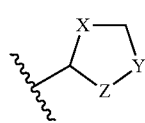

where:
X is $CH_2$, O, S or NH;
Y is $CH_2$, O, S or NH; and
Z is $CH_2$, C=O or CH(OH).

In specific embodiments, HGII is

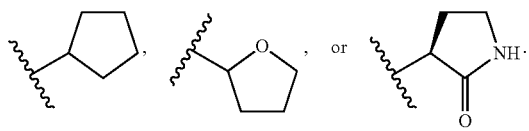

In more specific embodiments, HGII is

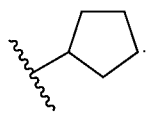 [SMILES: *C1CCCC1]

In more specific embodiments, HGII is

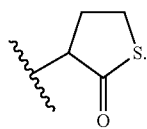 [SMILES: *C1CCSC1=O]

In more specific embodiments, HGII is

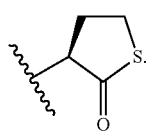

In more specific embodiments, HGII is

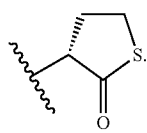

In specific embodiments, AII is p-I-phenyl. In specific embodiments, AII is p-I-phenyl and L is —O—$(CH_2)_m$—, where m is 1 or 2. In specific embodiments, AII is p-I-phenyl and L is —O—$(CH_2)_m$—, where m is 1 or 2, and W is —CO—NH— or —CO—NH—$CH_2$—. In specific embodiments, AII is p-I-phenyl, L is —O—$(CH_2)_m$—, where m is 1 or 2, and W is —CO—NH—. In specific embodiments, AII is p-I-phenyl, L is —O—$(CH_2)$—, and W is —CO—NH—.

In specific embodiments, AII is p-I-phenyl and HGII is

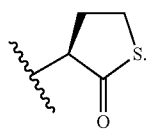 [SMILES: *[C@H]1CCSC1=O]

In specific embodiments, AII is p-I-phenyl and L is —O—$(CH_2)_m$—, where m is 1 or 2 and HGII is

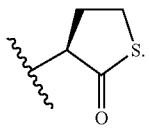 [SMILES: *[C@H]1CCSC1=O]

In specific embodiments, AII is p-I-phenyl and L is —O—$(CH_2)_m$—, where m is 1 or 2, and W is —CO—NH— or —CO—NH—$CH_2$— and HGII is

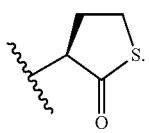 [SMILES: *[C@H]1CCSC1=O]

In specific embodiments, AII is p-I-phenyl, L is —O—$(CH_2)_m$—, where m is 1 or 2, and W is —CO—NH— and HGII is

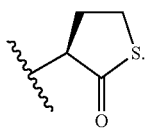 [SMILES: *[C@H]1CCSC1=O]

In specific embodiments, AII is p-I-phenyl, L is —O—$(CH_2)$—, and W is —CO—NH— and HGII is

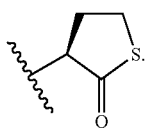 [SMILES: *[C@H]1CCSC1=O]

In embodiments, the compound of formula VII is

VIIB

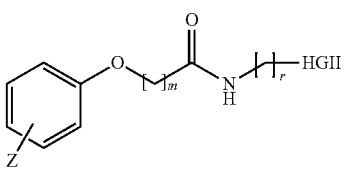

where Z represents substitution of the phenyl ring with 1-5 halogens, m is 1 or 2, r is 0 or 1 and HG II is as defined above for formula II. In specific embodiments, m is 1 and r is 0. In specific embodiments, m is 1 and r is 1.

In specific embodiments, Z represents substitution of the phenyl ring with 1, 2 or 3 halogens. In specific embodiments, Z represents substitution of the phenyl ring with 1, 2 or 3 halogens including a halogen in the para-ring position. In specific embodiments, Z represents substitution of the phenyl ring with 1, 2 or 3 halogens including a iodine in the para ring position. In specific embodiments, Z represents two halogens substituted on the phenyl ring. In specific embodiments, Z represents two halogens substituted on the phenyl ring. In specific embodiments, Z represents two halogens substituted on the phenyl ring with one of the halogens in the para ring position on the ring. In specific embodiments, Z represents two halogens substituted on the phenyl ring with one iodine in the para ring position on the ring. In specific embodiments, Z represents one halogen substituted on the phenyl ring. In specific embodiments, Z represents one halogen substituted on the phenyl ring in the para ring position. In specific embodiments, the halogens are I, Cl or F. In specific embodiments, the halogens are Br. In specific embodiments, the halogens are F. In specific embodiments, the halogens are I.

In specific embodiments of formula VIIB, HGII is

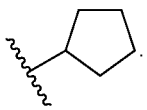 [SMILES: *C1CCCC1]

In specific embodiments of formula VIIB, HGII is

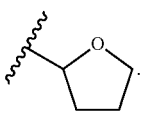

In specific embodiments of formula VIIB, HGII is:

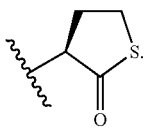 [SMILES: *[C@H]1CCSC1=O]

In specific embodiments, the compounds of formula VIIB are those which exhibit $IC_{50}$ measured as described herein in the *E. coli* reporter screen of 50 µM or less. In specific embodiments, the compounds of formula IIB are those which exhibit $IC_{50}$ measured in the *E. coli* reporter screen of 25 µM or less.

In specific embodiments, the compounds of formula VIIB are those which exhibit $IC_{50}$ measured as described herein in the *P. aeruginosa* reporter screen of 50 µM or less. In specific embodiments, the compounds of formula VIIB are those which exhibit $IC_{50}$ measured in the *P. aeruginosa* reporter screen of 25 µM or less.

In specific embodiments, the compounds of formula IIB are those which exhibit maximum inhibition measured in the *E. coli* reporter screen of 50% or more with respect to 10 µM BHL. In specific embodiments, the compounds of formula IIB are those which exhibit maximum inhibition measured in the *E. coli* reporter screen of 75% or more with respect to 10 µM BHL.

In specific embodiments, the compounds of formula VIIB are those which exhibit maximum inhibition measured in the *P. aeruginosa* reporter screen of 50% or more. In specific embodiments, the compounds of formula VIIB are those which exhibit maximum inhibition measured in the *P. aeruginosa* reporter screen of 75% or more.

Figure 15:
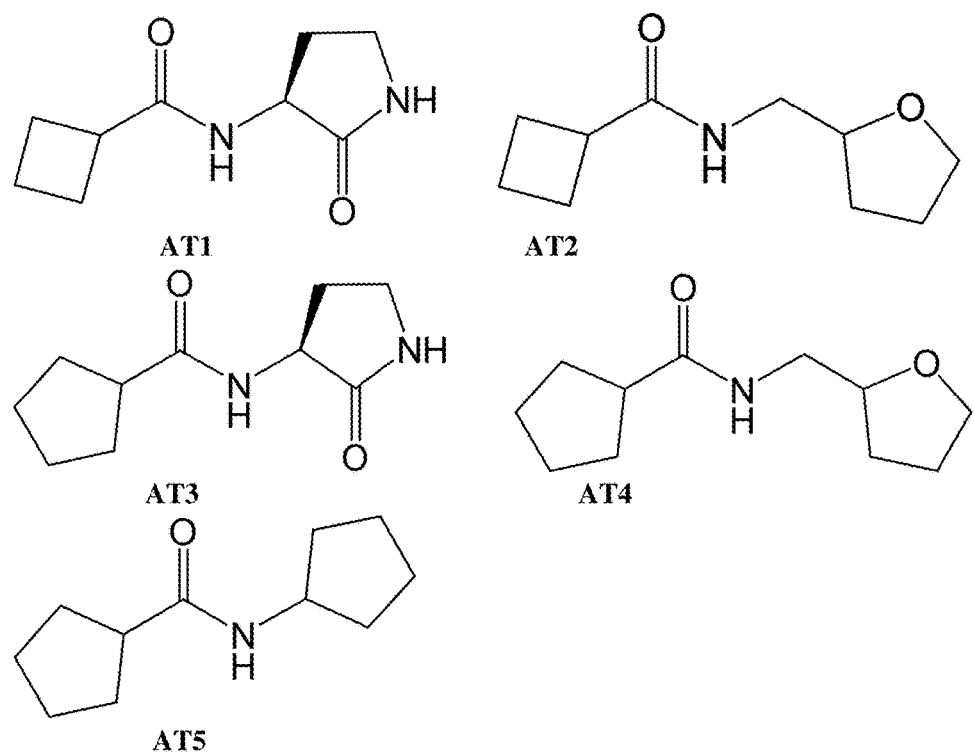
FIG. 15 provides structures of compounds AT1-AT5 which are exemplary RHlR antagonists.
Figure 16A:
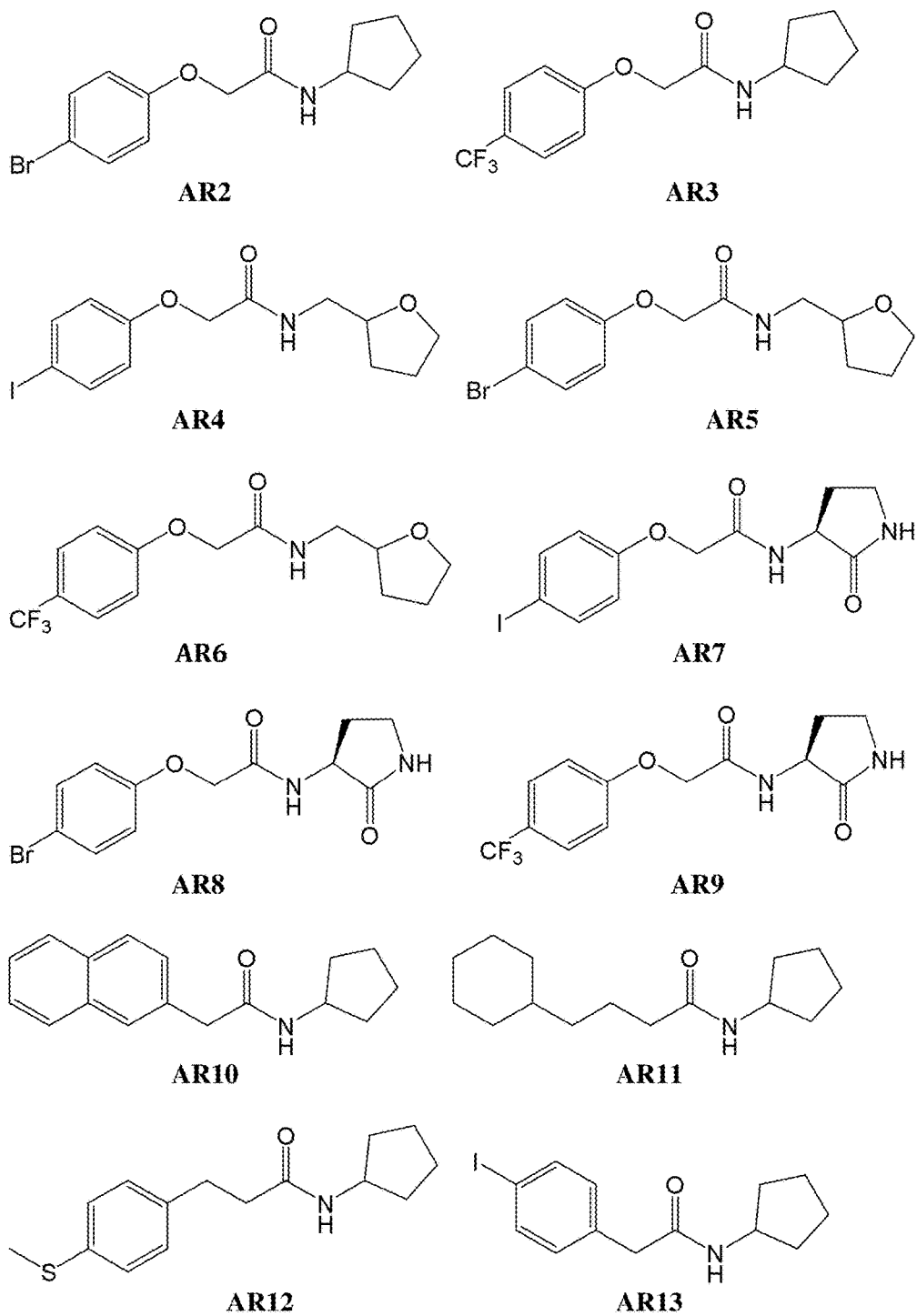
FIGS. 16A and 16B provide structures of additional exemplary RhlR modulators AR2-AR21.
Figure 16B:
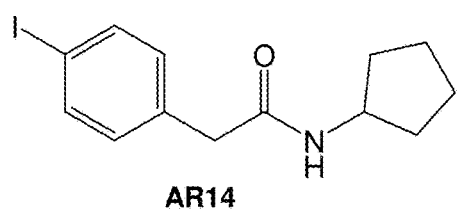
Figure 16B:
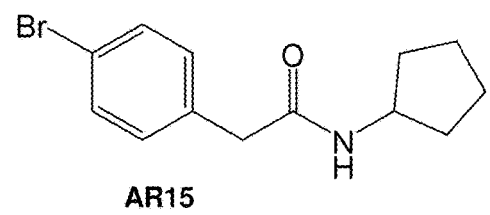
Figure 16B:
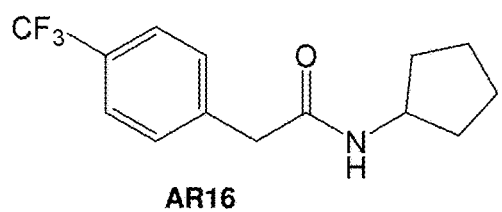
Figure 16B:
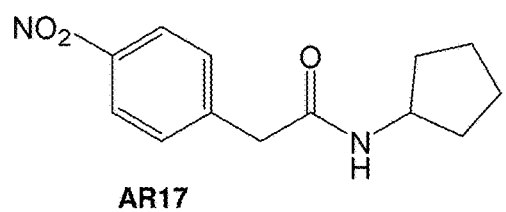
Figure 16B:
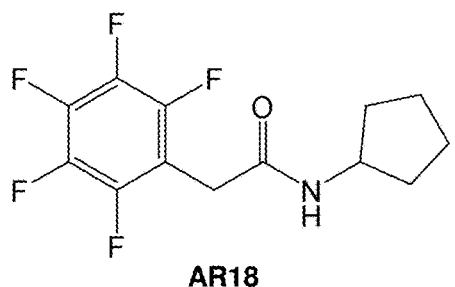
Figure 16B:
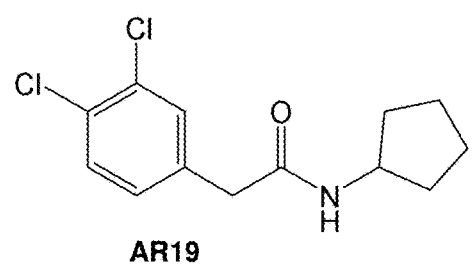
Figure 16B:
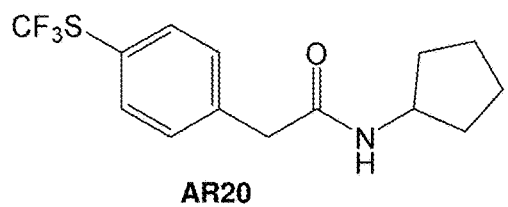
Figure 16B:
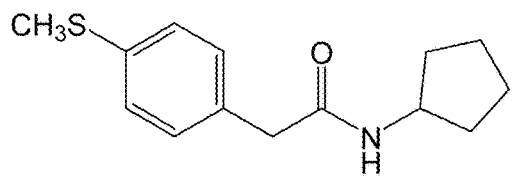

Exemplary RhlR antagonists AT1-AT5 are illustrated in FIG. 15 and RhlR antagonists AR2-AR21 are illustrated in FIGS. 16A and 16B.

In a specific embodiment, an RhlR antagonist useful in combinations herein is compound NR22:

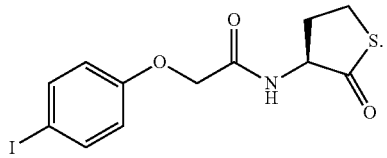

RhlR antagonists of formulas VII and VIIB are described in more detail in US provisional applications 62/329,942, filed Apr. 29, 2016 and 62/371,291, filed Aug. 17, 2016, each of which is incorporated by reference herein in its entirety for descriptions of RhlR modulators and particularly RhlR antagonists including information therein regarding $IC_{50}$ and other measures of antagonism.

PqsR antagonists include those of formula VITTII

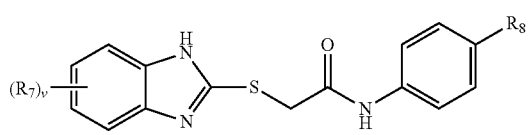

or salts thereof, where v is 1, 2, 3 or 4 (representing 1-4 $R_7$ substituents on the indicated ring);

$R_7$ is —NR'R", —NHCOR', —NO$_2$, —CN, —SR', or —SO$_2$R';

$R_8$ is an —OR$_9$ group or is a halogen;

$R_9$ is aryl, heteroaryl or heterocycloalkyl group which is unsubstituted or substituted with 1 to 5 substituents selected from —NR'R", —NO$_2$ or —NHCOR'", or two substituents together with the the carbon atoms to which they are attached form a heteroaryl or heterocycloalkyl moiety;

R' and R" are independently hydrogen or an unsubstituted alkyl having 1-6 carbon atoms (inclusive); and R'" is hydrogen, an unsubstituted alkyl having 1-6 carbon atoms (inclusive) or a haloalky having 1-6 carbon atoms (inclusive). In specific embodiments, $R_7$ is a 6-NO$_2$ (nitro at the 6-ring position) and $R_8$ is —OR$_9$. In specific embodiments, $R_9$ is an aryl group.

In specific embodiments, R' and R" are independently hydrogen or an alkyl have 1-3 carbon atoms. In specific embodiments, R' and R" are independently hydrogen or a methyl group. In specific embodiments, R' and R" are hydrogens. In specific embodiments, R'" is hydrogen. In specific embodiments, R'" is an unsubstituted alkyl having 1-3 carbon atoms (inclusive). In specific embodiments R'" is a methyl group. In specific embodiments, R'" is a haloalky having 1-3 carbon atoms (inclusive). In specific embodiments, R'" is a fluoro having 1-3 carbon atoms (inclusive). In specific embodiments, R'" is —CF$_3$.

In specific embodiments, $R_7$ is a 6-NO$_2$ and A is a phenyl group. In specific embodiments, $R_7$ is a 6-NO$_2$ group and $R_8$ is bromine or iodine.

In specific embodiments, the PqsR antagonist is:

(compound 4 (M64))

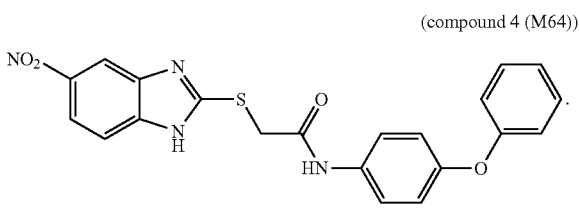 [SMILES: O=C(CSc1nc2cc([N+](=O)[O-])ccc2[nH]1)Nc1ccc(Oc2ccccc2)cc1]

In specific embodiments, the PqsR antagonist is:

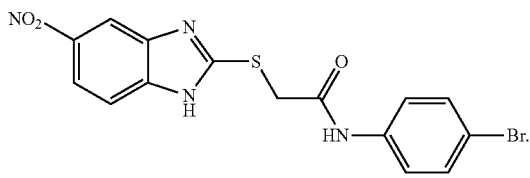 [SMILES: O=C(CSc1nc2cc([N+](=O)[O-])ccc2[nH]1)Nc1ccc(Br)cc1]

In specific embodiments, the PqsR antagonist is:

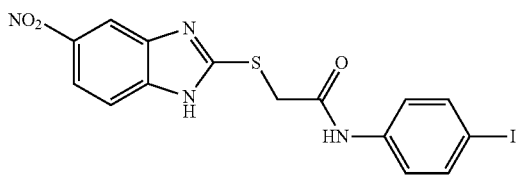 [SMILES: O=C(CSc1nc2cc([N+](=O)[O-])ccc2[nH]1)Nc1ccc(I)cc1]

With respect to compounds of formula VIII, U.S. Pat. No. 8,877,940 is incorporated by reference herein in its entirety for methods of synthesis of such compounds and for additional examples of such compounds. This reference further provides additional information on activity of compounds therein as inhibitors of quorum sensing.

The Rhl and Pqs systems work in tandem to drive virulence factor production in nutrient limiting conditions, while Las is only a minor contributor under such nutrient limiting conditions. LasR inhibitors display reduced activity in low iron and phosphate environments, and as a result, cocktails (mixtures) of RhlR and PqsR inhibitors can attenuate virulence in a broad range of conditions where Las antagonists are inactive. The activity trends uncovered herein are also predictive of compound activity in infection relevant environments, including the CF airway, which are nutrient limiting condition for the bacterium. Thus, the present work indicates unique roles for the *P. aeruginosa* QS systems in tailoring virulence factor production to the environment, and provides novel insights into pathways that, with further development, could potentially be targeted to fight this pathogen.

The terms "nutrient limiting" or "nutrient depleted" refer to bacterial environments that are limited or depleted with respect to the nutritional needs of a given bacterium, such that growth of the bacterium is limited under such conditions. Certain quorum sensing systems are sensitive to such "nutrient limiting" or "nutrient depleted" condition such that the systems are modulated in response to such limitation or depletion. The present work investigates quorum sensing inhibition and activation and the interaction of quorum sensing systems in such depleted or limited environments. Such limited or depleted environments can, for example, be bacterial infection sites, such as the CF airway, a burn or other wound site, the intestine or other in vivo site after surgery. Nutrient limitation or depletion in an in vivo environment can affect virulence of the bacteria in that environment and can affect the extent or virulence of a given infection. The term depleted and limited for a given nutrient are used relative to the level of that nutrient that supports unlimited growth of the bacterium or that is sufficiently high that a given quorum sensing system is not affected by the level of nutrient present. The amount of a given nutrient that results in such growth limitation or quorum sensing modulation will depend on the bacterium and may also depend upon other nutrients in the environment. One of ordinary skill in the art can determine if a given environment is depleted or limiting for a given bacterium without resort to undue experimentation using methods that are known in the art.

The combination of quorum sensing inhibitory compounds of the invention can be employed in any in vivo or in vitro application for inhibition of virulence of Gram-negative bacteria. Contact or administration of the combination of inhibitory compounds can be achieved by various means known in the art by combined or separate contact or combined or separate administration of component compounds of the combinations. Each component of a combination can be formulated separately or the combination of components can be formulated together.

In a specific embodiment, a composition for inhibition of virulence in a bacterium having multiple quorum sensing systems is provided, which comprises a combination of:
a selective LasR inhibitor and a selective RhlR inhibitor;
a selective LasR inhibitor and a selective PqsR inhibitor; or
a selective RhlR inhibitor and a selective PqsR inhibitor.

In a specific embodiment, the composition for inhibition of virulence in a bacterium having multiple quorum sensing systems consists of a combination of:
a selective LasR inhibitor and a selective RhlR inhibitor;
a selective LasR inhibitor and a selective PqsR inhibitor; or
a selective RhlR inhibitor and a selective PqsR inhibitor.

In a specific embodiment, the composition for inhibition of virulence in a bacterium having multiple quorum sensing systems comprises a combination of:
a selective RhlR inhibitor and a selective PqsR inhibitor.

In a specific embodiment, the composition for inhibition of virulence in a bacterium having multiple quorum sensing systems consists of a combination of:
a selective RhlR inhibitor and a selective PqsR inhibitor.

In a specific embodiment, the composition for inhibition of virulence in a bacterium having multiple quorum sensing systems comprises a selective Las R inhibitor which is a compound of formula I, formula II or formula III, a selective RhlR inhibitor which is a compound of formula IV, V, or VI and a selective PqsR inhibitors which is a compound of formula VIII.

In a specific embodiment, the composition for inhibition of virulence in a bacterium having multiple quorum sensing systems consists of a selective Las R inhibitor which is a compound of formula I, formula II or formula III, a selective RhlR inhibitor which is a compound of formula IV, V, or VI and a selective PqsR inhibitors which is a compound of formula VIII.

In a specific embodiment, the composition for inhibition of virulence in a bacterium having multiple quorum sensing systems comprises a LasR inhibitor of formula IE, a RhlR inhibitor of formula IVE and a PqsR inhibitor of formula VIII.

In a specific embodiment, the composition for inhibition of virulence in a bacterium having multiple quorum sensing systems consists of a LasR inhibitor of formula IE, a RhlR inhibitor of formula IVE and a PqsR inhibitor of formula VIII.

In a specific embodiment, the composition for inhibition of virulence in a bacterium having multiple quorum sensing systems comprises LasR inhibitor:

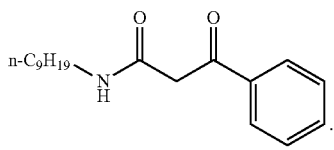

In a specific embodiment, the composition for inhibition of virulence in a bacterium having multiple quorum sensing systems comprises the RhlR inhibitor:

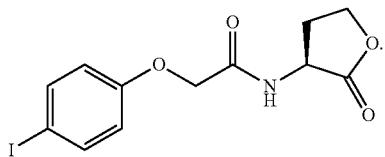 [SMILES: O=C(COc1ccc(I)cc1)N[C@H]1CCOC1=O]

In a specific embodiment, the composition for inhibition of virulence in a bacterium having multiple quorum sensing systems comprises the PqsR inhibitor:

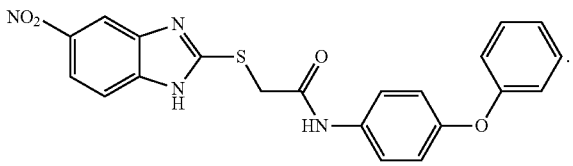 [SMILES: O=C(CSc1nc2cc([N+](=O)[O-])ccc2[nH]1)Nc1ccc(Oc2ccccc2)cc1]

In a specific embodiment, the composition for inhibition of virulence in a bacterium having multiple quorum sensing systems comprises:

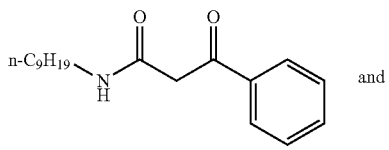

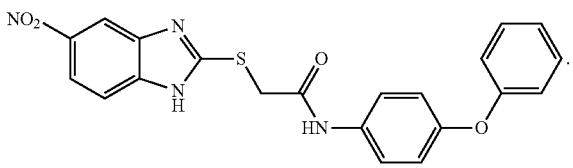

In a specific embodiment, the composition for inhibition of virulence in a bacterium having multiple quorum sensing systems comprises:

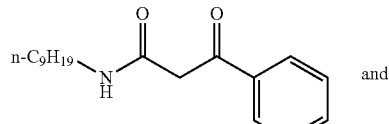

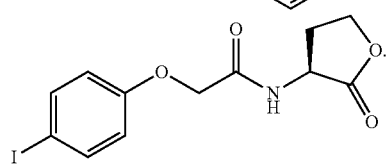

In a specific embodiment, the composition for inhibition of virulence in a bacterium having multiple quorum sensing systems comprises:

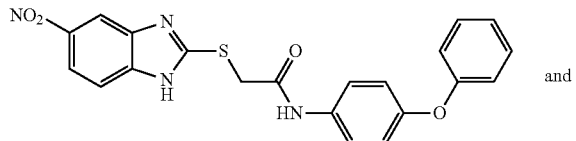

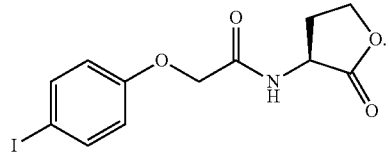 [SMILES: O=C(COc1ccc(I)cc1)N[C@H]1CCOC1=O]

In a specific embodiment, the composition for inhibition of virulence in a bacterium having multiple quorum sensing systems consists of:

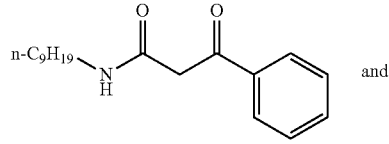

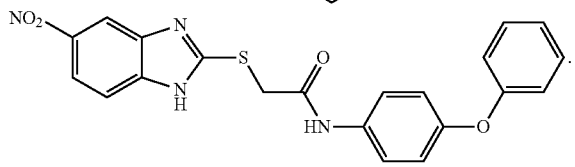

In a specific embodiment, the composition for inhibition of virulence in a bacterium having multiple quorum sensing systems consists of:

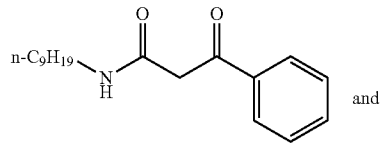

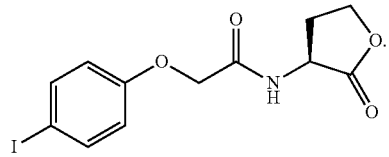

In a specific embodiment, the composition for inhibition of virulence in a bacterium having multiple quorum sensing systems consists of:

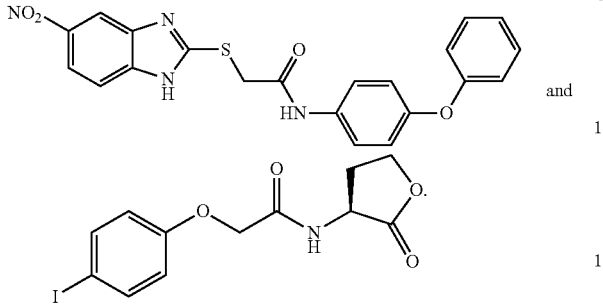

and

In a specific embodiment, the composition for inhibition of virulence in a bacterium having multiple quorum sensing systems comprises:

LasR inhibitor:

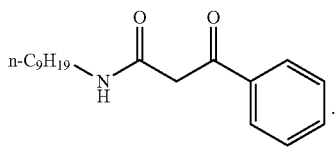

RHlR inhibitor:

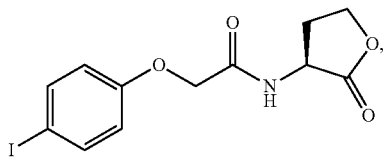

and

PqsR inhibitor:

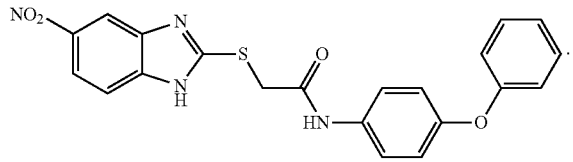 [SMILES: O=C(CSc1nc2cc([N+](=O)[O-])ccc2[nH]1)Nc1ccc(Oc2ccccc2)cc1]

In a specific embodiment, the composition for inhibition of virulence in a bacterium having multiple quorum sensing systems consists of:

LasR inhibitor:

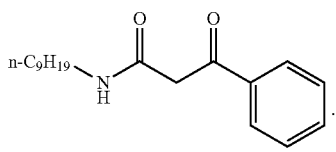

RHlR inhibitor:

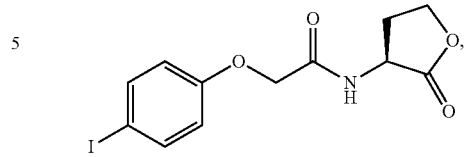

and

PqsR inhibitor:

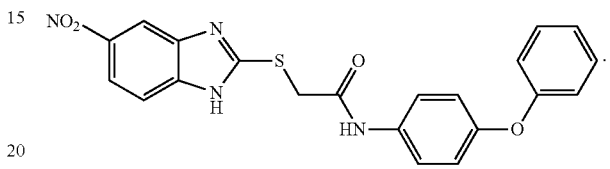

In specific embodiments of forgoing embodiments of compositions, the amount of a given inhibitor in the composition is an amount effective for selective inhibition of the indicated QS system.

The invention also provides a method for treating infections of Gram-negative bacteria in an individual in need of such treatment, wherein a therapeutically effective amount of a combination of compounds of any one or more formulas herein as further described herein or a pharmaceutically acceptable salt thereof are administered to said individual.

The invention also provides therapeutic compositions for treating infections of Gram-negative bacteria comprising a therapeutically effective amount of combinations of compounds of formulas herein or a pharmaceutically acceptable salt of the compound herein and a pharmaceutically acceptable carrier. In a specific embodiment, such therapeutic compositions comprise at least two quorum sensing compounds of formulas herein or a pharmaceutically acceptable salt thereof.

The invention also provides methods for making a medicament for treatment of a bacterial infection, particularly of a Gram-negative bacterium, and more particularly of a strain of *Pseudomonas* or a strain of *Burkholderia*, in which two or more different compounds of the invention, which are quorum sensing inhibitors, and particularly selective quorum sensing inhibitors, of different quorum sensing systems in the bacterium are combined to provide for enhanced inhibition. Such medicaments can further include a pharmaceutically acceptable carrier or excipient as are known in the art.

In an additional embodiment, the invention provides combinations of compounds of formulas herein and methods for reducing bacterial virulence and increasing susceptibility of quorum sensing bacterial to biocides and/or antibiotics.

For methods of inhibiting virulence or treating infections herein, compounds are administered to a patient or applied to an environment in an amount effective for inhibition of a given quorum sensing system. Generally an effective amount will be dependent upon the bacterium and the environment of the bacterium. In an embodiment for inhibiting a given bacterium in a given environment, the effective amount of a given compound is equal to or greater than the $IC_{50}$ of that compound for a given quorum sensing system. In an embodiment for administration to a mammal, the effective amount of a given compound for inhibition ranges from the $IC_{50}$ or $EC_{50}$ of the compound for inhibition to less than the toxicity level of the compound for mammalian cells. As defined herein, "contacting" means that a compound of the present invention is provided such that it is capable of making physical contact with another element, such as a microorganism, a microbial culture, a biofilm, or a substrate or other environment of a bacterium. In another embodiment, the term "contacting" means that a compound of the present invention is introduced into an individual receiving treatment, and the compound is allowed to come in contact in vivo. The term "administering" is also used for providing a compound or pharmaceutical composition to an individual in need of treatment. Various administration methods can be employed as will be appreciated by one of ordinary skill in the art.

The term "effective amount" is used generically herein to refer to the amount of a given compound or in case of a combination of compounds the combined amount of mixed components that provides a measurable effect for a listed function. In certain aspects of the invention, the effective amount is for treating an infection (see however, the more specific therapeutically effective amount below). In certain embodiments, the effective amount is for inhibition of virulence. In certain embodiments, the effective amount is for inhibition growth of a bacterium. Combinations of compounds of the invention, in certain embodiments, can inhibit growth or establishment of a biofilm. Combinations of compounds of the invention, in certain embodiments, can disperse an already formed biofilm.

For example, in certain aspects of the invention, a compound of the invention is contacted with an element (a substrate, a surface a tool an instrument or the like) in order to prevent formation of or disrupt a biofilm and in this case, the effective amount or combined effective amount of the compound or compounds is that amount that shows a measurable disruption of a biofilm. The effective amount will vary dependent upon the stated function, the environment or element being contacted, the organism forming the biofilm or which is to be contacted, the state of development of the biofilm, among other conditions of the use of the compound. It will be understood by one of ordinary skill in the art, that for a given application, the effective amount can be determined by application of routine experimentation and without undue experimentation by methods that are described herein or that are known in the art.

The term "therapeutically effective amount" is used generically herein to refer to the amount of a given compound or in case of a combination to the individual amount of components or the combined amount of a mixture components when administered to the individual (including a human, or non-human animal) that provides a measurable therapeutic effect for a listed disease, disorder or condition to at least partially ameliorate a symptom of such disease, disorder or condition. The present invention provides methods of treating disorders, diseases conditions and symptoms in a human or non-human animal and particularly in a human, by administering to an individual in need of treatment or prophylaxis, a therapeutically effective amount of one or more compounds of this invention to the individual in need thereof. The result of treatment can be partially or completely alleviating, inhibiting, preventing, ameliorating and/or relieving the disorder, condition or one or more symptoms thereof. As is understood in the art, the therapeutically effective amount of a given compound will depend at least in part upon, the mode of administration, any carrier or vehicle (e.g., solution, emulsion, etc.) employed, the extent of damage and the specific individual (human or non-human) to whom the compound is to be administered (age, weight, condition, sex, etc.). The dosage requirements needed to achieve the "therapeutically effective amount" vary with the particular compositions employed, the route of administration, the severity of the symptoms presented and the particular individual being treated. Based on the results obtained in standard pharmacological test procedures, projected daily dosages of active compound can be determined as is understood in the art.

Administration is intended to encompass administration of a compound (or combination of compounds as discussed herein), pharmaceutically acceptable salt, solvate or ester thereof alone or in a pharmaceutically acceptable carrier thereof or administration of a prodrug derivative or analog of a compound of this invention which will form an equivalent amount of the active compound or substance within the body. An individual in need of treatment or prophylaxis includes those who have been diagnosed to have a given disorder or condition and to those who are suspected, for example, as a consequence of the display of certain symptoms or of having been exposed to a pathogen, of having such disorders or conditions.

Compounds and combinations of compounds of this invention can be employed in unit dosage form, e.g. as tablets or capsules. In such form, the active compound or more typically a pharmaceutical composition containing the active compound is sub-divided in unit dose containing appropriate quantities of the active compound; the unit dosage forms can be packaged compositions, for example, packaged powders, vials, ampules, pre-filled syringes or sachets containing liquids. The unit dosage form can be, for example, a capsule or tablet itself, or it can be the appropriate number of any such compositions in package form.

The dosage can vary within wide limits and as is understood in the art will have to be adjusted to the individual requirements in each particular case. By way of general guidance, the daily oral dosage can vary from about 0.01 mg to 1000 mg, 0.1 mg to 100 mg, or 10 mg to 500 mg per day of a compound of formulas herein or of the corresponding amount of a pharmaceutically acceptable salt thereof. The daily dose may be administered as single dose or in divided doses and, in addition, the upper limit can also be exceeded when this is found to be indicated.

Any suitable form of administration can be employed in the methods herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts. Topical application can include those in which the biofilm-inhibitory compound is formulated in a hydrogel or encapsulated in microspheres or nanospheres, for example.

Compounds and combinations of compounds of this invention can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol. Administration includes any form of administration that is known in the art and is intended to encompass administration in any appropriate dosage form and further is intended to encompass administration of a compound, alone or in a pharmaceutically acceptable carrier.

Pharmaceutical carriers are selected as is known in the art based on the chosen route of administration and standard pharmaceutical practice.

The compounds and combinations of compounds of this invention can also be administered to the eye, preferably as a topical ophthalmic formulation. The compounds and combinations of compounds of this invention can also be combined with a preservative and an appropriate vehicle such as mineral oil or liquid lanolin to provide an ophthalmic ointment. The compounds and combinations of compounds of this invention may be administered rectally or vaginally in the form of a conventional suppository. The compounds and combinations of compounds of this invention may also be administered transdermally through the use of a transdermal patch containing the active compound and a carrier that is inert to the active compound, is non-toxic to the skin, and allows delivery of the agent for systemic absorption into the blood stream via the skin.

The compounds and combinations of compounds of the invention may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

Pharmaceutical compositions and medicaments of this invention comprise one or more compounds in combination with a pharmaceutically acceptable carrier, excipient, or diluent. Such compositions and medicaments are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety.

The invention also encompasses methods for making a medicament employing a combination of two or more compounds of this invention which exhibit a combined therapeutic effect.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Suitable examples of liquid carriers for oral and parenteral administration include water of appropriate purity, aqueous solutions (particularly containing additives, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form. The carrier can also be in the form of creams and ointments, pastes, and gels. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable.

Combinations of compounds of the invention include combinations of pharmaceutically acceptable salts if any of various compounds of the invention. The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. Compounds of formula I can also be present in the form of zwitterions.

Compounds of the invention can be in the form of salts which in specific embodiments are non-toxic and more specifically pharmaceutically-acceptable. Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl, Br), sulfate, acetates (e.g., acetate, trifluoroacetate), ascorbates, aspartates, benzoates, citrates, and lactate.

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

The invention expressly includes pharmaceutically usable solvates of compounds according to formulas herein. The compounds can be solvated, e.g. hydrated. The solvation can occur in the course of the manufacturing process or can take place, e.g. as a consequence of hygroscopic properties of an initially anhydrous compound of formulas herein (hydration).

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, Experimental and computational approaches to estimate solubility and permeability in drug discovery and development settings, Adv. Drug Del. Rev., 2001, 46, 3-26 and Arup K. Ghose, Vellarkad N. Viswanadhan, and John J. Wendoloski, A Knowledge-Based Approach in Designing Combinatorial or Medicinal Chemistry Libraries for Drug Discovery, J. Combin. Chem., 1999, 1, 55-68.) In general a preferred drug for oral administration exhibits no more than one violation of the following rules:

(1) Not more than 5 hydrogen bond donors (e.g., nitrogen or oxygen atoms with one or more hydrogens);

(2) Not more than 10 hydrogen bond acceptors (e.g., nitrogen or oxygen atoms);

(3) Molecular weight under 500 g/mol and more preferably between 160 and 480; and (4) log P less than 5 and more preferably between −0.4 to +5.6 and yet more preferably −1<log P<2.

Compounds of this invention preferred for therapeutic application include those that do not violate one or more of 1-4 above.

Compounds of this invention preferred for therapeutic application include those having log P less than 5 and more preferably between −0.4 to +5.6 and yet more preferably −1<log P<2.

The compounds of this invention may contain one or more chiral centers. Accordingly, this invention is intended to include racemic mixtures, diastereomers, enantiomers and mixture enriched in one or more stereoisomer. The scope of the invention as described and claimed encompasses the racemic forms of the compounds as well as the individual enantiomers and non-racemic mixtures thereof.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

As used herein, the term "treating" includes preventative as well as disorder remittent treatment. As used herein, the terms "reducing", "suppressing" and "inhibiting" have their commonly understood meaning of lessening or decreasing.

In certain embodiments, the present invention encompasses administering the compounds useful in the present invention to a patient or individual. A "patient" or "individual", used equivalently herein, refers to an animal. In particular, an animal refers to a mammal, preferably a human. The patient either: (1) has (is diagnosed to have or is believed to have) a condition remediable or treatable by administration of a compound of the invention; or (2) is susceptible to a condition that is preventable by administering a compound of this invention.

Additional embodiments of the invention include the following.

In an embodiment, the present invention provides a surface coating or polymer having incorporated therein a combination of compounds of the present invention. The amount of compounds or polymer in the surface coating is that sufficient to provide antifouling effect or provide for bacterial inhibition. In an embodiment, the combination of compounds of the present invention is useful as an antifouling agent or surface sterilizing agent. In specific embodiments, the compounds of this invention exhibit no substantial antimicrobial effect. Compounds of the present invention are further useful in a medical, scientific, and/or biological application.

In one aspect, the present invention provides a composition comprising one, two or more compounds of the present invention and a carrier or diluent. In a preferred embodiment, the carrier or diluent comprises a liquid. Such a liquid may comprises an aqueous solvent or a non-aqueous solvent. An exemplary solvent comprises one or more organic solvents. The carrier or diluent may also comprise an ionic liquid. In an embodiment of this aspect, the composition comprises an organic or inorganic polymeric substance. The polymeric substance may comprise one or more compounds of the present invention, admixed with a polymer, bound to a polymer, or adsorbed on to a polymer. In an exemplary embodiment of this aspect, the composition is in the form of a solution or suspension of said at least one compounds of the present invention, preferably in an aerosol or powder formulation.

In an embodiment of this aspect, the composition is formulated as a disinfectant or cleaning formulation. In another embodiment, the composition is in the form of a powder, a solution, a suspension, a dispersion, an emulsion, or a gel. In an exemplary embodiment, the composition is in the form of a pharmaceutical composition comprising a pharmaceutically acceptable carrier, diluent, and/or excipient and one or more compounds of the present invention. The composition may be in a form suitable for parenteral or non-parenteral administration. A preferred composition may be formulated for topical, intradermal, intramuscular, intraperitoneal, intravenous, subcutaneous, intranasal, epidural, ophthalmic, or oral administration. In an embodiment of this aspect the composition is formulated for administration by infusion or bolus injection, absorption through epithelial or mucocutanous linings and may be administered together with other biologically active agents. In an embodiment, the composition may further be formulated for use in an inhaler or nebulizer.

In another aspect, the present invention provides a method of treating an infection in a human or animal, the method comprising administration to the individual (human or animal) of a therapeutically effective amount of one or more compounds of the present invention. In an embodiment, the treatment is therapeutic or prophylactic.

In a related embodiment, the present invention provides a method of treating an infection or condition in an individual that is characterized by biofilm formation, the method comprising administering one or more compounds of the present invention. In an embodiment, the condition is cystic fibrosis. In an embodiment, the condition is dental caries, periodontitis, otitis media, muscular skeletal infections, necrotizing fasciitis, biliary tract infection, osteomyelitis, bacterial prostatitis, native valve endocarditis, cystic fibrosis pneumonia, or meloidosis. In an embodiment, the condition is a nosocomial infection; preferably the infection is ICU pneumonia or an infection associated with sutures, exit sites, arteriovenous sites, scleral buckles, contact lenses, urinary catheter cystitis, peritoneal dialysis (CAPD) peritonitis, IUDs, endotracheal tubes, Hickman catheters, central venous catheters, mechanical heart valves, vascular grafts, biliary stent blockage, orthopedic devices, or penile prostheses. In an embodiment, the infection is a skin infection, a burn infection, or a wound infection. According to this aspect, the individual may preferably be an immune-compromised individual.

In specific embodiments herein, contacting is achieved by release of combinations of the inhibitory compounds of the invention from a polymer film, multilayer film, hydrogel, or coating that contains the one or more biofilm-inhibitory compounds of the invention. In general, any art-known type of film, hydrogel or coating can be employed for containing and thereafter releasing one or more biofilm-inhibitory compounds of the invention. It will be appreciated that the film or coating (e.g., polymer) must be chemically compatible with and not inactivate the inhibitory compound. In other specific embodiments, contacting is achieved by encapsulation of and later release of one or more inhibitory compounds of the invention into the environment to be. Encapsulation can be by any art known method and can be in the form of micro- or nanoencapsulation.

Methods of this invention can be implemented employing thin films, multilayers, coatings, hydrogels, encapsulation and related delivery methods where the biofilm-inhibitory compounds are loaded in the films, coatings, hydrogels or are encapsulated for delivery over time to an environment having existing biofilms or which is susceptible to biofilm formation. Encapsulation can be in various forms including among others microspheres or nanospheres. The use of such delivery methods can provide for release of one or more biofilm-inhibitory compounds over time extending from days to week to months dependent upon the methods and specific materials employed. In specific embodiments, a surface is protected from biofilm formation by application of a thin film, a multilayer, a coating or the like to at least a portion of the surface. In a related embodiment, surfaces are protected from biofilm formation or cleaned of biofilms by application of a thin film, a multilayer, a coating or the like to a surface in the vicinity of the surfaces to be protected in order to release an effective amount of biofilm-inhibitory compound of the invention into the vicinity of the surfaces to be protected. In specific embodiments, films, multilayers, coatings or encapsulation methods provide a level of the biofilm-inhibitory compound to the surface or to the vicinity of a surface to be protected which ranges from the IC50 of the compound for biofilm inhibition to less than the toxicity level of the compound for mammalian cells. In specific embodiments, the concentration of biofilm-inhibitory compounds provided by such films, multilayers, coatings or encapsulation methods to the environment to be protected ranges from the $IC_{50}$ of the compound to less than 0.25 mM. More specifically, the concentration provided to the environment to be protected ranges from 10-100 micromolar.

In specific embodiments, films, multilayers and coatings generated using one or more polymers and which contain from about 0.001 to 1 mg or more preferably from 0.01 to 1 mg/gram of biofilm-inhibitory compound/gram of polymer are useful for biofilm inhibition or dispersion. In a specific embodiment, biofilm-inhibitory compounds of the invention are provided to a surface or a portion of a surface in film formed from a poly(lactide-co-glycolide).

The present invention further provides a method for treating or preventing biofilm formation on a surface, the method comprising contacting said surface with combined compounds of the invention in an amount effective for affecting biofilm formation of the present invention. In an embodiment, the surface is a non-biological surface. In an embodiment, the surface is a natural surface. In an embodiment, the surface is a surface of a plant, seed, wood, fiber or hair. In an embodiment, the surface is a biological surface; preferably the surface is a surface of a tissue, membrane, or skin. In an embodiment, the surface is a hard surface; preferably the surface comprises a metal, an organic polymer, an inorganic polymer, a natural elastomer, a synthetic elastomer, glass, wood, paper, concrete, rock, marble, gypsum, or ceramic. In an embodiment, the said surface is coated or wherein the surface is a coating; in a preferred embodiment, the coating comprises enamel, varnish, or paint.

In an embodiment of this aspect, the surface is a soft surface, and may be the surface of a fiber comprising a yarn, a textile, a vegetable fiber, or rock wool. In another embodiment, the surface is a porous surface. In an embodiment, the surface is a surface of process equipment or components of cooling equipment. In a preferred embodiment, the process equipment is or is a component of a cooling tower, a water treatment plant, a dairy processing plant, a food processing plant, a chemical process plant, or a pharmaceutical process plant. In a preferred embodiment, the surface is that of a filter or a membrane filter.

In an embodiment of this aspect, the surface is a surface of a toilet bowl, a bathtub, a drain, a high-chair, a counter top, a vegetable, a meat processing room, a butcher shop, food preparation areas, an air duct, an air-conditioner, a carpet, paper or woven product treatment, a diaper, personal hygiene products and a washing machine. In another embodiment, the surface is an industrial surface or a medical surface; preferably the surface is a surface in a hospital, a veterinary hospital, a mortuary, or a funeral parlor.

In another aspect, the combined compounds of the present invention are useful as a component of a dentifrice, a mouthwash, or a composition for the treatment of dental caries; for treatment of acne; or for cleaning and/or disinfecting contact lenses. The compounds of the present invention are further useful for incorporation into the surface of a medical device or an implant device. Preferably the implant device is an artificial heart valve, hip joint, an indwelling catheter, pacemaker, or surgical pin. The compounds of the present invention are further useful as an antifouling coating. The present invention further provides an optical lens, wherein at least a part of a surface of the lens is associated with one or more compounds of the present invention. Preferably, the optical lens is a contact lens.

In another aspect, the present invention provides a biofilm removing or inhibiting composition comprising combined compounds of the present invention in an amount effective for removing or inhibiting biofilm formation and a vehicle or carrier, wherein the amount of the mixture is effective to remove or disrupt a bacterial biofilm or inhibit normal biofilm formation. An embodiment of this aspect may further comprise a surfactant selected from the group consisting of an anionic surfactant, a nonionic surfactant, an amphoteric surfactant, a biological surfactant, and any combination of these; or a compound selected from the group consisting of a biocide, a fungicide, an antibiotic, and any combination of these.

The term antibacterial agent refers generically to chemical species that exhibit bacteriostatic or bactericidal effect. Of particular interest are antibacterial agents effective against one or more Gram-negative bacteria and particularly those that are effective against *Pseudomonas*, and more particularly against *P. aeruginosa*. Antibacterial agents include disinfectants such as chlorine, bromine and chlorine dioxide and quaternary ammonium compounds, as well as antibiotics. A variety of antibiotics are known in the art and one of ordinary skill in the art can select one or more antibiotics appropriate for use against a given species or strain of Gram-negative bacteria. Antibiotics useful in the method of this invention include among others gentamicin, kanamycin neomycin, streptomycin and other aminoglycoside antibiotics, which are of particular use against *P. aeruginosa* infections.

Additional exemplary classes of antibiotics include among others Penicillins, Cephalosporins, Carbapenems, Tetracyclines, Macrolides, Quinolones and Sulfonamides. One of ordinary skill in the art can readily chose amongst known antibiotics of these classes for use in the methods herein.

In another embodiment, the invention provides a film, multilayer film, hydrogel or coating, for application to a surface or in the vicinity of a surface, containing a combination of compounds of the invention to inhibit or prevent biofilm formation on the surface.

In another embodiment, the invention provides a combination of compounds of the invention, such as a pharmaceutical composition, a disinfectant composition, an encapsulated formulation, a coating for application to a surface or similar composition. Such compositions are useful to regulate a symbiotic behavior of quorum sensing bacteria. This symbiotic behavior may be biofilm formation. Other symbiotic behaviors that may be regulated include swarming, motility, sporulation, conjugation, bioluminescence and/or production of pigments, antibiotics and enzymes. Quorum sensing molecules of the formulas of this invention may in one embodiment inhibit, decrease or attenuate a behavior of quorum sensing bacteria, particularly Gram-negative quorum sensing bacteria, particularly *Pseudomonas* and more particularly *P. aeruginosa*.

In an embodiment, a coating containing a combination of compounds of the invention can be applied to a variety of surfaces using methods that are well-known in the art. The coating may be in the form of a film, including a multi-layer film, or a gel, particularly a hydrogel, comprising one or more of the compounds of this invention. Coatings can be employed in medical and non-medical applications. Specific applications include coated medical devices (e.g., stents, catheters, and feminine hygiene products) and industrial coatings (e.g., ship hulls and heat exchangers). The coating may be applied to the surfaces of interest using a variety of known methods. In specific embodiments, the coating loaded with one or more inhibitory compounds of this invention is formed by solvent casting. In other embodiments, the loaded coating is formed by spin coating. In other embodiments, the loaded coating is formed by dip coating. In other embodiments, one or more of solvent casting, spin coating or dip coating is employed to form surfaces carrying inhibitory loaded films of this invention.

In an embodiment, inhibitory compounds and combinations thereof the invention can be encapsulated in thin bulk films of conventional polymers, such as PLA, or PLGA by known methods such as dip-coating or solvent casting. Such films can be applied to surfaces as desired where the encapsulated inhibitor is released to inhibit or prevent biofilm formation on the surface. In an embodiment, biofilm inhibitors of this invention can be loaded into nanostructured polymer multilayers, for example, PEMs and other cross-linked multilayers, for example, using a layer-by-layer approach. Multilayers can be applied to or formed on surfaces to release biofilm inhibitor to inhibit or prevent biofilm formation on the surface. Sustained release of the inhibitors can be obtained using such methods. Methods useful for making films or coatings including multilayer films are described, for example, in Lynn and co-workers: Adv. Mater. 2007; Biomacromolecules 2009; Adv. Mater. 2010; Langmuir 2010; ACS App. Mater. Inter. 2010; Langmuir 2010; Chem. Mater. 2010; J. Mater. Chem. 2011; Adv. Biomat. 2011; Biomacromolecules 2011 and in U.S. Pat. Nos. 7,883,720; 8,071,210 and published US applications US20080286345 and US20090105375, each of which is incorporated by reference herein for descriptions of methods and materials, particularly polymers and co-polymers, useful for forming films, multilayer films and the like. It will be appreciated that combinations of the invention can be individually encapsulated or otherwise formulated and such individual encapsulated compounds or other individual formulations can be combined in an application, contacting step or administration step to achieve the desired combined effect that is discussed herein.

More generally for contact or administration herein, a combination of compounds can applied to a bacterium, an environment of a bacterium or administered to a patient simultaneously or separately, at the same site at the same time or a different time, in the same type of formulation or dosage form or in a different type of formulation or a different dosage form.

In specific embodiments, the invention provides films, coatings or hydrogels containing one of or a combination of the inhibitory compound of the invention. In specific embodiments, films, coatings and/or hydrogels or the like of this invention provide a concentration of an inhibitory compound into the environment to be protected (e.g., a surface) that is effective for inhibiting virulence. In an embodiment, such coatings, inhibit formation of a biofilm or disperse an already formed biofilm. Such coatings can provide for some level of decrease of bacteria on such surfaces. In specific embodiments, films, coatings and/or hydrogels or the like of this invention provide a concentration of a one or more inhibitory compounds into the environment to be protected that ranges from the $IC_{50}$ of the biofilm-inhibitory compound (which can be measured by methods as described herein) to the level of the compound that is cytotoxic to mammalian cells (which can be measured by methods as described herein). In specific embodiments, films, coatings and/or hydrogels or the like of this invention provide a concentration of a inhibitory compound into the environment to be protected that ranges from the $IC_{50}$ of the inhibitory compound (which can be measured by methods as described herein) to 0.250 mM. In more specific embodiments, the concentration of inhibitory compound provided to the environment to be protected ranges from 4 microM to 200 microM. In yet more specific embodiment, the concentration ranges from 2-10 time the $IC_{50}$ of the biofilm-inhibitory compound to 200 microM. In additional embodiments, the concentration ranges from 10-200 microM, 10-100 microM, 20-100 microM, 40-200 microM, or 40 to 100 microM. Combination of the compounds of the invention can be achieved by combination of the compounds in a film, coating or hydrogel or can be achieved in a combination of films, coatings or hydrogels wherein each film, coating or hydrogel contains a different compound of the combination of compounds.

In specific embodiments, the loading of the film, coating or hydrogel with the biofilm-inhibitory compound ranges from 0.001 to 1 mg of compound/gram of polymer in the film, coating or hydrogel. In more specific embodiments, the loading of the film, coating or hydrogel with the biofilm-inhibitory compound ranges from 0.005 to 1 mg, 0.01 to 1 mg, 0.05 to 1 mg, 0.1 to 1 mg, 0.5 to 1 mg, 0.01 to 0.5 mg of compound/gram of polymer in the film, coating or hydrogel.

The combination of compounds of the invention can be applied to an environment or administered by individual controlled-release of the component compounds of the combination of inhibitory compounds of the invention or by combined controlled-release of a combination of compounds. Controlled release can be from a film formed on the surface to be protected or on a surface in the vicinity of the surface to be protected. Similar release can be used to disperse already-formed biofilms. Release from the film provides for spatially localized release at or near the surface to be protected or cleaned of biofilm enhancing the effectiveness of biofilm-inhibition. The rate of release can be controlled by changing the composition of film, coating or hydrogel as is known in the art. The release profile from the film can also be affected by varying the thickness of the films and the concentration of the one or more biofilm-inhibitory compounds in the film. The concentration of biofilm-inhibitory compounds in the film can be generally uniform throughout the film or the concentration may be non-uniform in the film.

The film, coating or hydrogel may be formed on the surface of a selected substrate by any known method. For example, the film may be formed by contacting of the surface with a solution of the polymer and active ingredient (e.g., one or more inhibitory compounds), allowing a film to form on the surface and repeating the contacting step until a film of desired thickness is formed. The concentration of active ingredient(s) can be the same or different in the contacting steps. For example, the solution in one or more steps may contain polymer, but no active ingredient.

The films of this invention may also be formed by dip-coating, spin coating, or solvent casting using methods known in the art.

In additional embodiments, the inhibitory compounds of the invention be provided in bulk objects and optionally released from such objects. Bulk objects include disks, slabs and other substrates and other structural elements that can be implanted, incorporated or used in other ways in biomedical or non-biomedical application. For example, one or more inhibitory compounds of a combination of compounds of the invention can be incorporated into such objects, e.g., by absorption. In a specific embodiment, one or more biofilm-inhibitory compounds of the invention can be introduced into porous matrix of an object to provide for biofilm protection.

In specific embodiments, the inhibitory compounds and combinations thereof of this invention are non-bactericidal or can be employed at levels which are inhibitory without being bactericidal. In such embodiments, concerns associated with evolved resistance currently faced by approaches based on the use of conventional microbiocidal agents (e.g., antibiotics) are lessened.

The term alkyl as used herein refers to a saturated hydrocarbon group which is straight-chain or branched. Unless otherwise stated, an alkyl group can have from 1-20 carbon atoms. More specifically, an alkyl group can have from 1-18 carbon atoms. In certain embodiments, an alkyl group can have from 1-3 carbon atoms. In certain embodiments, an alkyl group can have from 6-20 carbon atoms. In certain embodiments, an alkyl group can have from 6-16 carbon atoms. In certain embodiments, an alkyl group can have from 8-20 carbon atoms. In certain embodiments, an alkyl group can have from 8-16 carbon atoms.

The term alkoxy refers to an —O-alkyl group where the alkyl group is as defined above.

The term haloalkyl refers to an alkyl group substituted with one or more halogens. Halogens include fluorine, chlorine, bromine or iodine. Specific haloalkyl groups include halomethyl groups having 1-3 halogen substituents. Specific haloalkyl groups include —$CF_3$, —$CCl_3$, —$C_2F_5$, —$C_2Cl_5$ among others.

The term haloalkoxy refers to an —O-haloalkyl group where the haloalkyl group is defined herein.

The term aryl refers to monocyclic or polycyclic (e.g., having 2 or more fused rings). Preferred polycyclic aryl groups have 2 or 3 rings, which may be fused or not fused. Aryl groups include phenyl, naphthyl, indanyl, indenyl, anthracenyl, phenanthrenyl among others. In certain embodiments, aryl groups have 6-20 carbon atoms. The term aryl oxy refers to an —O-aryl group. An example aryl oxy group is phenoxy.

The term cycloalkyl refers to a non-aromatic cyclic hydrocarbon which can have moncyclic or polycyclic ring systems. Polycyclic ring systems can include those with 2-4 fused rings or 2-4-ring spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, among others. Carbon atoms of the cycloalkyl group can be optionally oxidized, i.e., have an oxo or sulfildo group to form CO or CS. In specific embodiments, cycloalkyl group may include one or more double or triple bond in a ring. In specific embodiments, cycloalkyl group may include one double or triple bond in a ring.

The term heteroaryl refer to an aromatic heterocyclic group having at least one heteroatom ring member such as sulfur, oxygen, or nitrogen. Heteroaryl groups can be monocyclic or polycyclic (e.g., having 2, 3 or 4 fused rings) systems. Exemplary heteroaryl groups include among others, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl. In certain embodiments, the heteroaryl group has from 1 to about 20 carbon atoms. In other embodiments, the heteroaryl group has from 3 to 20 carbon atoms. In certain embodiments, a heteroaryl group contains 3 to about 14, 3 to about 7, or 5 to 6 ring-forming atoms. In certain embodiments, the heteroaryl group has 1 to about 4, 1 to about 3, or 1 to 2 heteroatoms.

The term heterocycloalkyl refers to non-aromatic heterocyclic group wherein one or more of the ring-forming carbon atoms are replaced by a heteroatom such as an O, N, or S atom. Heterocycloalkyl groups include those having one or more than one ring (not all rings need contain an O, S or N atom). Rings may be fused or non-fused. These groups can also include moieties in which one or more aromatic rings are fused to the nonaromatic heterocyclic ring, for example phthalimidyl, naphthalimidyl, and benzo derivatives of heterocycles such as indolene and isoindolene groups. Heterocyclic groups can be monocyclic or polycyclic and may contain from 1-20 carbon atoms, or in other embodiments, 3 to 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds.

In some embodiments, the heterocycloalkyl group contains 0 to 2 triple bonds. Exemplary heterocycloalkyl groups include morpholino, thiomorpholino, piperazinyl, tetrahydrofuranyl, tetrahy-drothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, 3H-isobenzofuran-1-one, 1,3-dihydro-isobenzofuran, 2,3-dihydro-benzo[d]isothiazole 1,1-dioxide, among others.

The term arylalkyl refers to alkyl substituted by aryl and cycloalkylalkyl" refers to alkyl substituted by cycloalkyl. An example arylalkyl group is benzyl.

The term amino refers to $NH_2$. The term alkylamino refers to an amino group substituted by an alkyl group. The term dialkylamino refers to an amino group substituted by two alkyl groups.

The various chemical groups defined above may be unsubstituted or substituted at a carbon or at a heteroatom which can be substituted, with one or more non-hydrogen substitutents. Generally, non-hydrogen substituents for the above groups include halogen, alkyl group having 1-6 or 1-3 carbon atoms, alkoxy group having 1-6 or 1-3 carbon atoms, alkylsulfanyl (—S-alkyl) group having 1-6 or 1-3 carbon atoms, a haloalkyl having 1-6 or 1-3 carbon atoms, a haloalkoxy having 1-6 or 1-3 carbon atoms, nitro, cyano, isocyano, thiocyano, isothiocyano, $-SO_2$, —OH, azide, sulfhydryl (—SH), $-CO_2H$, COH, —NHCOH, $-CONH_2$, $-OCONH_2$, $-NH_2$, $-CO_2R_{sub}$, $COR_{sub}$, $-NHCOR_{sub}$, $-CON(R_{Nsub})_2$, $-OCON(R_{Nsub})_2$, $-N(R_{Nsub})_2$, -phenyl group which are in turn are optionally substituted with one or more of the listed non-hydrogen substituents, -benzyl groups which are in turn optionally substituted with one or more of the listed non-hydrogen substituents, or where two substituents together with the atoms to which they are bonded can form a 5- to 8-member carbo cyclic or heretocyclic ring wherein the heteroatom is one or two N, S or O. Substitution also included substitution of one or more —O—, —S—, —NH—, —CO—, or —CS— in a carbon or heterocyclic ring. Haloalkyl and haloalkoxy substituent include fluoroalkyl and fluoralkoxy groups having 1-6 or 1-3 carbon atoms and having 1-13 fluorines.

As to substitution of any of the above groups, it is understood, that such groups do not contain any substitution or substitution patterns which are sterically impractical and/or synthetically non-feasible. In addition, the compounds of this invention include all stereochemical isomers arising from the substitution of these compounds.

Welsh et al., 2015; Moore et al., 2015 and Eibergen et al., 2015 provide detailed description of certain QS sensing modulators useful in this invention and useful in general for modulation of QS in bacteria, particularly Gram-negative bacteria and more particularly in *P. aeruginosa*. These references also provide assays for assessment of the relative antagonism and agonism caused by various QS modulators that are useful in the assessment of the selectively of a given antagonist or agonist for a given QS system with respect to other QS systems in the same bacterium. In particular, the Appendices provide assays for the assessment of the selectivity of LasR inhibitors with respect to inhibition and/or activation of RhlR and PqsR. In particular, these references provide assays for the assessment of the selectivity of RhlR inhibitors with respect to inhibition and/or activation of LasR and PqsR. In particular, these references provide assays for the assessment of the selectivity of PqsR inhibitors with respect to inhibition and/or activation of LasR and RhlR.

QS modulators include those of formula CI:

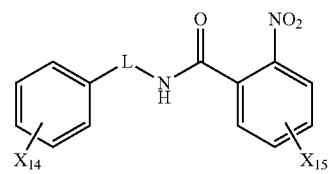

and salts thereof where:

L is $-(CH_2)_z-$, where z is 0, 1, 2 or 3 (noting that when z is 0, L is a single bond), $-CH(CH_3)-$, or $-(CH(CH_3)-CH_2)-$, $X_{14}$ represents 5 hydrogens on the indicated ring or 1-5 non-hydrogen substituents on the ring with the remaining ring carbons carrying hydrogen;

$X_{15}$ represents 4 hydrogens on the indicated ring or 1-4 non-hydrogen substituents on the ring with the remaining ring carbons carrying hydrogen, with the exception that $X_{15}$ does not include substitution with a nitro group;

wherein non-hydrogen substituents are selected from an amino, alkylamino, nitro, halogen, alkyl having 1-6 carbon atoms, alkoxy having 1-6 carbon atoms, alkylsulfanyl (alkyl-S—) having 1-6 carbon atoms, a haloalkyl having 1-3 carbon atoms or a haloalkoxy having 1-3 carbon atoms.

In a specific embodiment, L is $-(CH_2)_z-$, where z is 0, 1, 2 or 3.

In a specific embodiment, L is $-(CH(CH_3)-CH_2)-$, wherein the methyl group is on the carbon bonded to the ring having $X_{14}$ substituents. In specific embodiments, L is selected from:

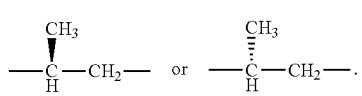

In a specific embodiment, L is $-CH(CH_3)-$, In specific embodiments, L is selected from:

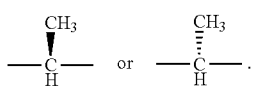

An amino group herein is —NH$_2$. An alkylamino group herein is —N(R$_{14}$)$_2$ where each R$_{14}$ is hydrogen or alkyl having 1-3 carbon atoms and at least one R$_{14}$ is alkyl.

In specific embodiments, alkyl, alkoxy or alkylsulfanyl substituents have 1-4 carbon atoms. In specific embodiments, alkyl, alkoxy or alkylsulfanyl substituents have 1-3 carbon atoms. In specific embodiments substituents include methyl, methoxy or methylsulfanyl (CH$_3$—S—) groups. In specific embodiments, haloalkyl or haloalkoxy substituents have 1-3 carbon atoms and 1 to 7 halogens. In specific embodiments, haloalkyl or haloalkoxy substituents have 1 or 2 carbon atoms and 1 to 5 halogens. In specific embodiments, haloalkyl or haloalkoxy substituents have 1 carbon atom and 1 to 3 halogens. In specific embodiments, haloalkyl or haloalkoxy groups are fluoroalkyl groups. In a specific embodiment, the haloalkyl group is —CF$_3$. In a specific embodiment, the haloalkoxy group is —OCF$_3$. In specific embodiments, X$_{15}$ represents the presence of 4 hydrogens on the indicated ring. In specific embodiments, X$_{15}$ represents the presence of a single substituent selected from halogen or haloalkyl. In specific embodiments, X$_{15}$ represents the presence of a single substituent selected from alkyl or alkoxy.

In specific embodiments, X$_{14}$ represents 1 or 2 halogens substituted on the indicated ring. In specific embodiments, X$_{14}$ represents 1 or 2 alkyl groups substituted on the indicated ring. In specific embodiments, X$_{14}$ represents 1 or 2 alkoxy groups substituted on the indicated ring. In specific embodiments, X$_{14}$ represents 1 or 2 nitro groups substituted on the indicated ring. In specific embodiments, X$_{14}$ represents 1 or 2 amino or alkyl amino groups substituted on the indicated ring.

In specific embodiments, X$_{14}$ represents 1 or 2 halogens substituted on the indicated ring, wherein at least one halogen is in the para-ring position. In specific embodiments, X$_{14}$ represents 1 or 2 halogens substituted on the indicated ring, wherein at least one halogen is in the ortho-ring position. In specific embodiments, X$_{14}$ represents 1 or 2 halogens substituted on the indicated ring, wherein at least one halogen is in the meta-ring position. In specific embodiments, X$_{14}$ represents 1 or 2 alkyl groups substituted on the indicated ring, wherein at least one alkyl group is at the ortho-position. In specific embodiments, X$_{14}$ represents 1 or 2 alkoxy groups substituted on the indicated ring, wherein at least one alkoxy group is in the para-position. In specific embodiments, X$_{14}$ represents 1 or 2 alkoxy groups substituted on the indicated ring, wherein at least one alkoxy group is in the ortho-position. In specific embodiments, X$_{14}$ represents 1 or 2 nitro groups substituted on the indicated ring, wherein at least one nitro group is in the ortho-position. In specific embodiments, X$_{14}$ represents 1 or 2 nitro groups substituted on the indicated ring, wherein at least one nitro group is in the meta-position. In specific embodiments, X$_{14}$ represents 1 or 2 nitro groups substituted on the indicated ring, wherein at least one nitro group is in the para-position. In specific embodiments, X$_{14}$ represents 1 or 2 amino or alkyl amino groups substituted on the indicated ring, wherein at least one amino or alkyl amino group is at the ortho position.

In specific embodiments, X$_{14}$ represents a single halogen substituted on the indicated ring in the meta-ring position. In specific embodiments, X$_{14}$ represents a single Br substituted on the indicated ring in the meta-ring position. In specific embodiments, X$_{14}$ represents a single nitro group substituted on the indicated ring in the ortho-ring position. In specific embodiments, X$_{14}$ represents a single nitro group substituted on the indicated ring in the meta-ring position.

In specific embodiments of all the forgoing embodiments, z is 1 or 2. In specific embodiments of all the forgoing embodiments, z is 0. In specific embodiments of all the forgoing embodiments, z is 3. In specific embodiments of all the forgoing embodiments, z is 1. In specific embodiments of all the forgoing embodiments, z is 2.

Modulators further include compounds of formula C2A:

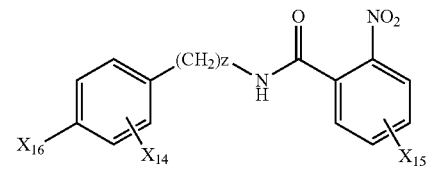

where
z is o, 1, 2, or 3 (preferably 1 or 2);
X$_{16}$ is a halogen and preferably is Br or I; and
X$_{14}$ represents 4 hydrogens or 1 or 2 substituents selected from halogen, alkyl, alkoxy, alkylsulfanyl (alkyl-S—), haloalkyl or a haloalkoxy (preferably 4 hydrogen or a single halogen substituent).
and X$_{15}$ is as defined above and is preferably 4 hydrogens.

Modulators further include compounds of formula C2B:

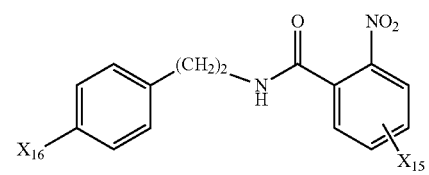

where X$_{16}$ is a halogen and preferably is Br or I;
and X$_{15}$ is as defined above and is preferably 4 hydrogens.

Modulators further include compounds of formula C3:

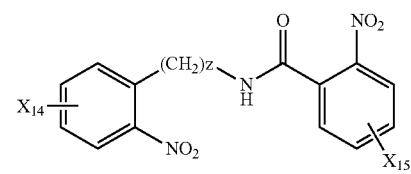

where:
z is 0, 1, 2 or 3 (preferably 1);
X$_{14}$ represents 4 hydrogens on the indicated ring or 1-4 and preferably 1 non-hydrogen substituent selected from halogen, alkyl having 1-6 carbon atoms, alkoxy having 1-6 carbon atoms, alkylsulfanyl (alkyl-S—) having 1-6 carbon atoms, a haloalkyl having 1-3 carbon atoms or a haloalkoxy having 1-3 carbon atoms; and
X$_{15}$ is as defined above and is preferably 4 hydrogens.

Modulators include agonists and antagonists of LasR.
Antagonist of LasR include compounds of formula CI above wherein:

$X_{14}$ substituents are selected from all hydrogen on the ring, or non-hydrogen substituents selected from ortho-nitro, halogen, alkyl having 1-6 carbon atoms, alkoxy having 1-6 carbon atoms, alkylsulfanyl (alkyl-S—) having 1-6 carbon atoms, a haloalkyl having 1-3 carbon atoms or a haloalkoxy having 1-3 carbon atoms; or $X_{14}$ substituents are selected from 1 or 2 ortho-halogen, meta-halogen, or para-halogen, or mixture of two thereof; or $X_{14}$ substituents are selected from ortho-nitro; or $X_{14}$ includes halogen substitution on the meta-position of the indicted ring, or $X_{14}$ includes halogen substitution on the meta-position of the indicted ring and L is —(CH$_2$)—, or $X_{14}$ includes halogen substitution on the para-position of the indicated ring, L is —(CH$_2$)$_2$—.

Specific antagonists of formula CI are compounds 4, 6, 8, 10, 13 and 17 (as numbered in O'Reilly and Blackwell, 2015), where L is —CH$_2$—, $X_{15}$ is 4-hydrogens and $X_{14}$-substituted phenyl is 3-fluoro-phenyl (m-fluropheny), 3,5-difluorophenyl, 3,4-difluorophenyl, 3-chlorophenyl, or 3-bromophenyl, or where L is —CH$_2$—CH$_2$—, $X_{15}$ is 4-hydrogens and $X_{14}$-substituted phenyl is 4-bromophenyl.

Agonists of the compounds of formula CI include those in which $X_{14}$ substitution includes a single meta-nitro group.

In specific embodiments, $X_{15}$ is 4 hydrogens, or $X_{15}$ having one alkyl, alkoxy or halogen.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

When a chemical group, including any substituent group, is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Isotopic variants of the compounds disclosed herein are part of the invention. Isotopic variants include those in which one or more hydrogens are substituted with deuterium or tritium. Isotopic variants include those in which one or more carbons, nitrogens, oxygens or fluorines are substituted at least in part with one or more stable isotopes such that the isotopic content of a given chemical species is different from the isotopic natural abundance. Isotopic variants of compounds of the invention are useful for example in biological assays and as isotopic labels.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

THE EXAMPLES

Example 1

Experimental Procedures

A. General Experimental Information. All absorbance and fluorescence measurements were made in 200 μL of solution in a 96-well microtiter plate (Costar 3370) using a Biotek Synergy 2 plate reader running Gen 5 software (version 1.05). Assay data were analyzed using Microsoft 329 Excel for Mac 2011 and GraphPad Prism 6 for Mac OS X (version 6.0f).

Compounds 1 (O'Loughlin et al., 2013), 2 (Geske et al., 2008a), and 3 (Mattmann et al., 2011) were synthesized as previously reported. Compound 4 (Starkey et al., 2014) was prepared as described in Example 3. Stock solutions of compounds (100 mM) were prepared in DMSO and stored at −20° C. in sealed vials.

B. Bacterial Strains and Growth Conditions. The bacterial strains and plasmids used in this study are listed in Table 1.

The MOPS minimal medium used in this study was prepared as described (Mellbye and Schuster, 2014). The assay medium was prepared prior to each experiment by diluting 10×MOPS Buffer (500 mM MOPS, 40 mM Tricine, 500 mM NaCl, 10 mM $K_2HSO_4$, 500 μM $MgCl_2$, 100 μM $CaCl_2$, 3 μM $(NH4)6Mo_7O_{24}$, 400 μM $H_3BO_3$, 30 μM $Co(OAc)_2$, 10 μM $CuSO_4$, 80 μM $MnSO_4$, 10 μM $ZnSO_4$, pH 7.0, filter sterilized) into sterile 18 MΩ water. To this solution, sterile 10× stock solutions of the carbon source (250 mM D-glucose or L-glutamic acid) followed by sterile 100× stock solutions of the phosphate (400 mM $K_2HPO_4$), iron (500 μM $FeSO_4$), and nitrogen source (1.5 M $NH_4Cl$) were added in appropriate amounts.

SCFM2 was prepared as described (Turner et al., 2015). SCFM2 is composed of 10 mM MOPS, 1.3 mM $NaH_2PO_4$, 1.25 mM $Na_2HPO_4$, 348 μM $KNO_3$, 271 μM $K_2SO_4$, 2.28 mM $NH_4Cl$, 14.9 mM KCl, 51.8 mM NaCl, 1.75 mM $CaCl_2$, 606 μM $MgCl_2$, 3.6 μM $FeSO_4$, 3 mM D-glucose, 9.3 mM DL-lactic acid, 1.45 mM L-serine, 1 mM L-threonine, 1.8 mM L-alanine, 1.2 mM L-glycine, 1.7 mM L-proline, 1.1 mM L-isoleucine, 1.6 mM L-leucine, 1.1 mM L-valine, 0.8 mM L-aspartate, 1.5 mM L-glutamate,

TABLE 1

Bacterial strains and plasmids used herein.

| Strain or plasmid | Description* | Reference |
|---|---|---|
| *Pseudomonas aeruginosa* | | |
| PAO1 | Wild-type | (Holloway, 1955) |
| PAO-JG33 | PAO1 ΔlasR::Tet; $Tc^R$ | (Gerdt and Blackwell, 2014) |
| PAO-KT1 | PAO1 ΔrhlR | This work |
| PAO-MW1 | PAO1 ΔpqsR | This work |
| *Escherichia coli* | | |
| DH5☐ | F−, j80dlacZDM15D(lacZYA-argF)U169 deoR recA1 endA1 hsdR17(rk−, mk+)phoA supE44 λ− thi-1 gyrA96 relA1 | Invitrogen |
| S17-1 λpir | recA pro thi hsdR− hsdM+ RP4-2-Tc::Mu-Km::Tn7 λpir; $Sm^R$ $Tp^R$ | (Simon et al., 1983) |
| Plasmids | | |
| pEAL08-2 | PqsR expression vector and pqsA'-lacZ transcriptional fusion; PqsR reporter vector; $Ap^R$ | (Cugini et al., 2007) |
| pEX18-Gm | Gene-replacement vector; sacB oriT $Gm^R$ | (Hoang et al., 1998) |
| pJG055 | pEX18-Gm with markerless ΔrhlR cassette | (Gerdt and Blackwell, 2014) |
| pMW4099 | pEX18-Gm with markerless ΔpqsR cassette | This work |

*Abbreviations: $Tc^R$, tetracycline resistance; $Gm^R$, gentamicin resistance; $Ap^R$, Ampicillin resistance; $Sm^R$, streptomycin resistance; $Tp^R$, trimethoprim resistance.

Protocols for construction of genetic knockout strains are described below in Example 2. All reagents for bacterial culture were purchased from Sigma-Aldrich unless indicated otherwise. Bacteria were routinely cultured in Luria-Bertani broth (LB) at 37° C. with shaking at 200 rpm. Freezer stocks of bacterial strains were maintained at −80° C. in 1:1 LB:glycerol. Bacterial growth was routinely assessed by measuring the culture cell density according to absorbance at 600 nm (OD600341). Cell growth in simulated cystic fibrosis sputum medium (SCFM2) was determined by serially diluting assay cultures, plating on LB agar, and counting the number of colony forming units (CFU) appearing after overnight incubation at 37° C. No compound had an effect on bacterial growth over the concentrations tested, except where noted in the text (FIGS. 2A-2D).

0.5 mM L-phenylalanine, 0.8 mM L-tyrosine, 13 μM L-tryptophan, 2.1 mM L-lysine, 0.5 mM L-histidine, 0.3 mM L-arginine, 0.7 mM L-ornithine, 0.2 mM L-cysteine, 0.6 mM L-methionine, 0.3 mM N-acetylglucosamine, 100 μg/mL 1,2-dioleoyl-sn-glycero-3-phosphocholine (DOPC), 0.6 mg/mL salmon sperm DNA, 5 mg/mL bovine maxillary mucin (Alfa Aesar), pH 6.8. The turbid nature of SCFM2 medium prevented routine OD600 readings; thus, the data presented in FIG. 12 (discussed below) are not growth normalized. However, no growth effects were observed in SCFM2 when full growth curves were generated in the presence of each compound (see FIGS. 2A-2D).

Example 2

Biological Methods

A. Construction of Strain PAO-KT1 (rhlR Knockout). The plasmid pJG055 was transformed into *E. coli* S17-1 λpir by electroporation and then transferred into wild-type *P. aeruginosa* (PAO1) by conjugation. Individual colonies were isolated on VB agar plates (0.2 g/L $MgSO_4$, 2 g/L citric acid, 10 g/L $K_2HPO_4$, 3.5 g/L $NaNH_4HPO_4$, 1.5% agar) containing 10 μg/mL gentamycin. Strain PAO-KT1 was isolated by counter-selection on LB-sucrose agar plates. The deletion was confirmed by sequencing of genomic DNA amplified from around the rhlR region.

B, Construction of Plasmid pMW4099 and Strain PAO-MW1 (pqsR Knockout) To delete the pqsR gene, an approximately 1 kb region up-stream of pqsR was amplified from PAO1 genomic DNA using primers:

```
                                    (SEQ ID NO: 1)
KN03 (5'-ACTTCTAGAAGCGTTCTCCAGCAGACGC-3')
and
                                    (SEQ ID NO: 2)
KN04 (5'-TATAAGCTTGGTGCGCGACATGCTCAAG-3').
```

This insert was cut with XbaI and HindII and ligated into XbaI/HindIII-cut pEX18-Gm to provide plasmid pMW4078. An approximately 1 kb region down-stream of pqsR was amplified from PAO1 genomic DNA using primers:

```
                                    (SEQ ID NO: 3)
KN02 (5'-GTATCTAGACCCTTATTCCTTTTATTGGGTGGC-3')
and
                                    (SEQ ID NO: 4)
KN08 (5'-ATAGATGAATTCTTGAGGATCTTCGCC-3').
```

This insert was cut with XbaI and EcoRI and ligated into XbaI/EcoRI-cut pMW4078. The resulting plasmid pMW4099 was inserted into *E. coli* S17-1 λpir by electroporation and transferred into wild-type *P. aeruginosa* (PAO1) by conjugation. Individual merodiploid colonies were isolated on VB agar plates (see above) containing 10 μg/mL gentamycin. Strain PAO-MW1 was isolated by counter-selection on LB-sucrose agar plates. The deletion was confirmed by sequencing of genomic DNA amplified from around the pqsR region.

C. *E. Coli* PqsR Reporter Gene Assay Protocol. β-galactosidase assays to quantify PqsR activity were performed in *E. coli* DH5a/pEAL08-2 using a previously reported method (Geske et al., 2007), with the following modifications (Cugini et al., 2007, Lu et al., 2012). A DMSO stock solution of 4 (25 mM) was serially diluted and added to the wells of a clear plastic 96-well microtiter plate in 2 μL aliquots. A subculture of *E. coli* DH5a/pEAL08-2 was prepared by diluting an overnight culture 1:1000 with fresh LB medium containing 100 μg/mL ampicillin and incubated until the bacteria had grown to $OD_{600}$=0.15. The subculture was treated with 100 nM PQS (Sigma-Aldrich), from a 1 mM DMSO stock, and 198 μL aliquots of this culture was added to each well of the microtiter plate (1% DMSO, final). Plates were incubated for 2 h. To assess β-galactosidase activity, 20 μL of final culture was lysed, and 100 μL of the aqueous layer from each lysate was transferred to the wells of a clear, flat-bottom 96-well microtiter plate. The substrate, chlorophenol red-β-D-galactopyranoside (CPRG, Roche) (4 mg/mL in phosphate-buffered saline), was added to each well in 16.7 μL volumes. Plates were incubated at room temperature until the positive control wells developed a deep red color (approximately 5 min). The amount of processed CPRG substrate was assessed by measuring the absorbance of each well at 570 nM using a plate reader. Enzymatic activity was calculated using the following equation:

Miller Units=$1000*Abs_{570}/(OD_{600}*t*V)$, where $t$=the incubation time (min) of CPRG with lysate and $V$=the volume of culture lysed (mL).

Example 3

Synthesis of Compound 4

A. General All reagents and solvents were purchased from Sigma-Aldrich and used without further purification. Thin-layer chromatography (TLC) was performed on 250 μm silica plates from Silicycle. Flash column chromatography was performed using Silica Gel P60 from Silicycle. NMR spectra were recorded at room temperature in deuterated acetone at 500 MHz on a Bruker Avance-500 spectrometer with a DCH cryoprobe and SampleXpress. Exact mass measurements were obtained using a Waters LCT electrospray ionization (ESI) TOF mass spectrometer. Samples were dissolved in acetonitrile and sprayed with a cone voltage of 20 V.

B. Synthesis of N-(4-phenoxyphenyl)-chloroacetamide

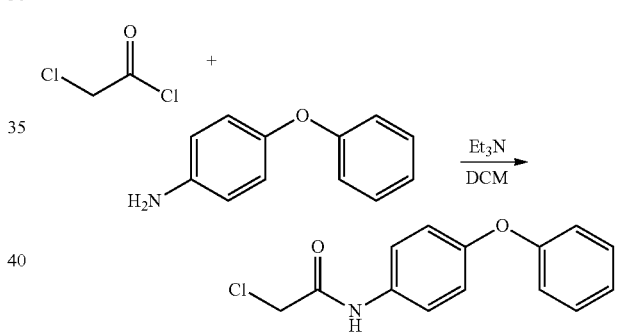

4-phenoxyaniline (1 g, 5.4 mmol, 1 eq.) was dissolved in anhydrous dichloromethane (DCM; 11 mL) in a flame-dried 50 mL round-bottom flask, and triethylamine (828 μL, 5.94 mmol, 1.1 eq.) was added. Chloroacetyl chloride (473 μL, 5.94 mmol, 1.1 eq.) was dissolved in anhydrous DCM (6 mL) and slowly added drop-wise to the round-bottom flask at room temperature with stirring. The reaction mixture was stirred under $N_2$ at room temperature until the starting materials were consumed (as gauged via TLC; approximately 2 h). The reaction mixture was washed 2× with sat. $NaH_2CO_3$ and 1× with brine, and the organic layer was separated and dried over $MgSO_4$. Volatiles were removed in vacuo to afford a dark gray solid. The crude product was used without further purification.

C. Synthesis of 2-[(6-nitro-1H-benzimidazol-2-yl)-sulfanyl]-N-(4-phenoxyphenyl)acetamide (i.e., Compound 4)

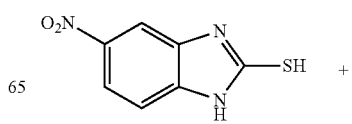

-continued

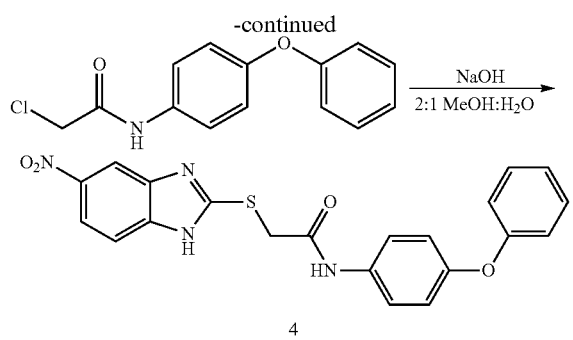

4

In a 250 mL round-bottom flask, the crude N-(4-phenoxyphenyl)-chloroacetamide (1.41 g, 5.4 mmol, 1 eq.) was dissolved in methanol (MeOH; 60 mL). 6-nitro-2-thiobenzimidazole (1.05 g, 5.4 mmol, 1 eq.) was added, followed by 3 M aqueous NaOH (30 mL). The reaction mixture was stirred at 70° C. for 3 h. After cooling to room temperature, MeOH was removed in vacuo, and the aqueous layer was extracted 3× with ethyl acetate (EtOAc). The organic layers were combined, washed 1× with brine, and dried over $MgSO_4$, and the solvent was removed in vacuo. The crude product was purified by flash column chromatography on silica gel (eluting with 2:1 to 1:1 hexane:EtOAc) and isolated from a co-eluting orange side product by recrystallization in 1:1 hexane:EtOAc to afford compound 4 as a pale yellow solid (153 mg, 6.7% yield over two steps).
$^1$H NMR (500 MHz, Acetone-$d_6$) δ 12.36 (s, 1H), 10.15 (s, 1H), 8.45 (s, 1H), 8.14 (dd, J=8.8, 2.2 Hz, 1H), 7.77-7.64 (m, 3H), 7.35 (dd, J=8.6, 7.2 Hz, 2H), 7.09 (t, J=7.4 Hz, 1H), 6.99-6.96 (m, 4H), 4.27 (s, 2H); EI-MS: calculated m/z [M+1]$^+$421.0965, observed m/z [M+1]$^+$421.0952.

Example 4

Assays

A. Pyocyanin Assay Protocol. The amount of pyocyanin in *P. aeruginosa* culture supernatants was measured following a reported protocol (O'Loughlin et al., 2013) with modifications. A 10 mL overnight culture of *P. aeruginosa* PAO1 was grown for 16 h. DMSO stock solutions of test compounds (20 mM) were prepared, and 10 μL or 5 μL aliquots were added to sterile 15 mL borosilicate glass test tubes. An inoculating culture was prepared by diluting the overnight culture 1:100 into freshly prepared assay medium (see above), and 2 mL aliquots of this subculture were added to each test tube (0.5% DMSO, final). The cultures were grown for 17 h, and the final cell density measured by reading OD600. Relative pyocyanin levels were measured by first pelleting 1.5 mL of well-mixed culture at 4,000 g for 10 min, transferring 200 μL of the resulting supernatant to a clear, plastic 96-well microtiter plate, and reading absorbance at 695 nm. Media background absorbance (measured from a "no bacteria" control) was subtracted, the resulting values growth normalized by dividing by the final OD600378, and the data plotted relative to a DMSO-treated positive control.
B. Rhamnolipid Assay Protocol. Rhamnolipid was quantified following a reported protocol (Koch et al., 1991) with modifications. Assay cultures were prepared and grown in an identical manner to the pyocyanin assay above. Aliquots of the final culture supernatant (1 mL) were transferred to 1 dram glass vials and extracted twice with 1 mL diethyl ether. The pooled organic fractions were evaporated to dryness, and the resulting residue reconstituted in 200 μL de-ionized water. In a 1.7 mL plastic centrifuge tube, 50 μL of this extract was diluted into 450 μL of a solution of 0.19% (w/v) orcinol in 50% (v/v) concentrated $H_2SO_4$ (or 20 μL extract into 480 μL orcinol solution for cultures grown in MOPS Glucose medium). The tubes were vortexed thoroughly to mix and incubated in an 80° C. heating block for 30 min. After briefly cooling to room temperature, 200 μL of the resulting yellow to yellow-orange solution was transferred to a clear 96-well microtiter plate, and the absorbance at 421 nm measured. Media background absorbance (measured from a "no bacteria" control) was subtracted, the resulting values growth normalized by dividing by the final OD600, and the data plotted relative to a DMSO-treated positive control.
C. Elastase B Assay Protocol. The amount of elastase B in *P. aeruginosa* culture supernatants was measured following a reported protocol (Geske et al., 2007) with modifications. Assay cultures were prepared and grown in an identical manner to the pyocyanin assay above. Aliquots of the final culture supernatant (50 μL) were added to the wells of a clear, plastic 96-well plate. To each well, 150 μL of 0.5% (w/v) elastin-congo red conjugate (Elastin Products Co.) in Tris buffer (10 mM Tris-HCl, 1 mM $CaCl_2$, pH 7.2) was added. The plate was sealed with a polypropylene storage mat (Costar 3080) and incubated in a 37° C. shaking incubator (200 rpm) attached to a Labquake rotator for 12 h (for experiments in SCFM2) or 24 h (for experiments in MOPS medium). To quantify elastase B activity, the undigested elastin was pelleted by centrifugation of the assay plate at 1,500 g for 10 min, after which 100 μL of the supernatant was transferred to a new, clear 96-well plate, and the absorbance at 490 nm measured. Media background absorbance (measured from a "no bacteria" control) was subtracted, the resulting values growth normalized by dividing by the final OD600, and the data plotted relative to a DMSO-treated positive control.

Example 5

LasR Inhibitor is Ineffective Under Low Phosphate Conditions

*P. aeruginosa* strains carrying nonfunctional lasR mutations are known to produce virulence factors through Rhl and Pqs in stationary phase, when essential nutrients begin to be depleted from the assay medium (Dekimpe and Ddziel, 2009, Cabeen, 2014). In particular, low phosphate concentrations are known to stimulate Rhl and Pqs via the response regulator PhoB (FIG. 1A) (Jensen et al., 2006). Therefore, both the contribution of Las to virulence and the ability of a LasR antagonist to attenuate virulence may be conditional. To test this hypothesis, WT *P. aeruginosa* (PAO1) was grown in a MOPS buffered minimal medium, MOPS100 Glutamate (Mellbye and Schuster, 2014), with or without phosphate diluted 10-fold from the medium. The cells were treated with compound 1, a strong LasR antagonist (Müh et al., 2006; Moore et al., 2015) (FIG. 1B), and production of the virulence factor pyocyanin was monitored over time.

Figure 3:
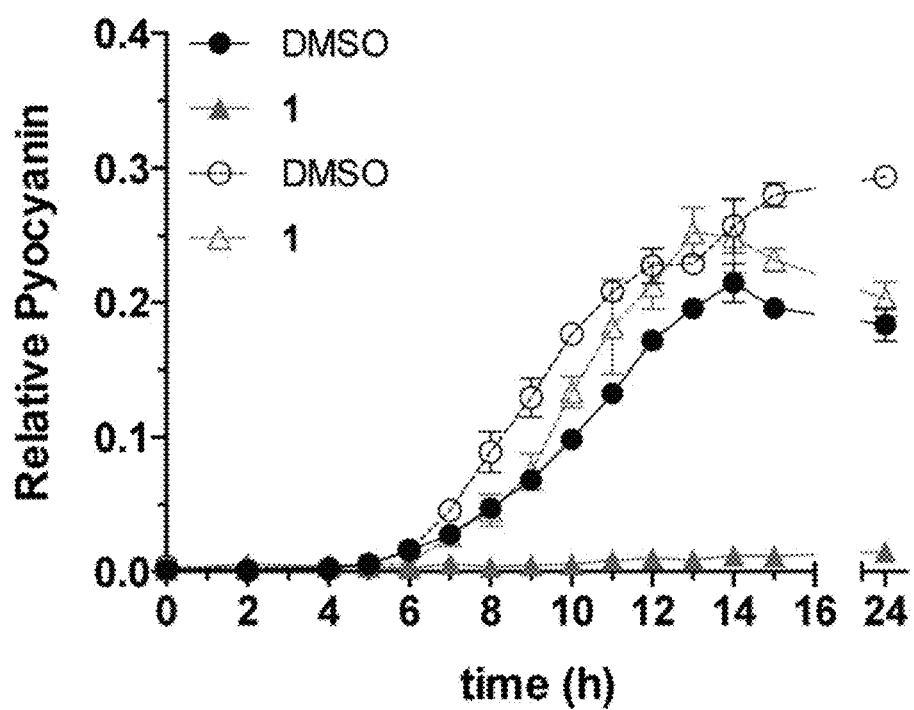
FIG. 3 is a graph showing chemical inhibition of LasR does not attenuate pyocyanin production in low phosphate medium. *P. aeruginosa* strain (PAO1) was grown in MOPS Glutamate medium treated with DMSO or 100 microM compound 1, and pyocyanin levels were quantified at the indicated time points. Filled shapes indicate experiments in complete MOPS Glutamate. Open shapes indicate experiments in MOPS Glutamate where the phosphate concentration in the medium was diluted 10-fold. Error bars represent the standard error of two biological replicates (n=2). Compound 1 had no effect on cell growth as shown in FIGS. 2A-2D, above.
Figure 4A:
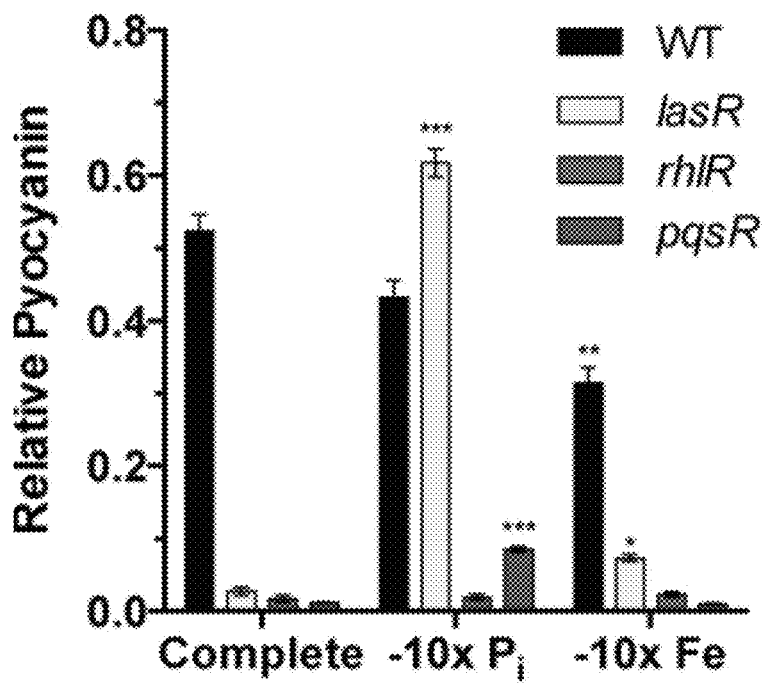
FIGS. 4A-4F are graphs of the relative amounts of certain virulence factors generated by certain *P. aeruginosa* strains in different media. The legend in FIG. 4A applies to all of FIG. 4A-4F. The data illustrate that *P. aeruginosa* requires Rhl and Pqs for full virulence when iron and phosphate are depleted. *P. aeruginosa* (PAO1) and isogenic lasR, rhlR, and pqsR mutants were grown in (FIGS. 4A, B, and C) MOPS Glutamate and (FIGS. 4D, E, and F) MOPS Glucose medium. The relative levels of pyocyanin, rhamnolipid, and elastase B in the final culture supernatant were quantified after 17 h incubation and normalized to the final cell density (OD600601). Error bars represent the standard error of at least three biological replicates (n≥3). P values (calculated by one-way ANOVA and Dunnett's multiple comparison post-test using GraphPad Prism software) indicate a statistical change from complete medium. *=$p<0.05$, =$p<0.005$, *=$p<0.0005$.
Figure 4B:
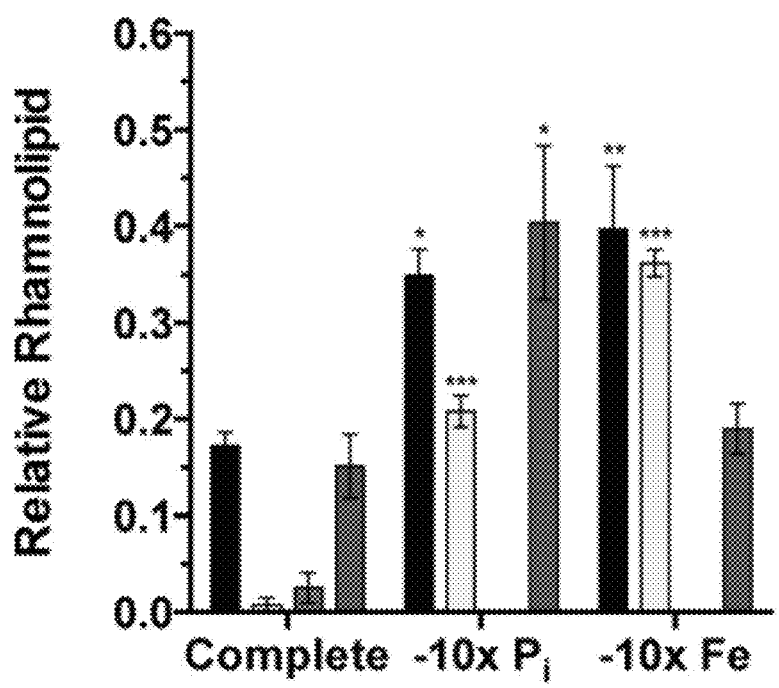
Figure 4C:
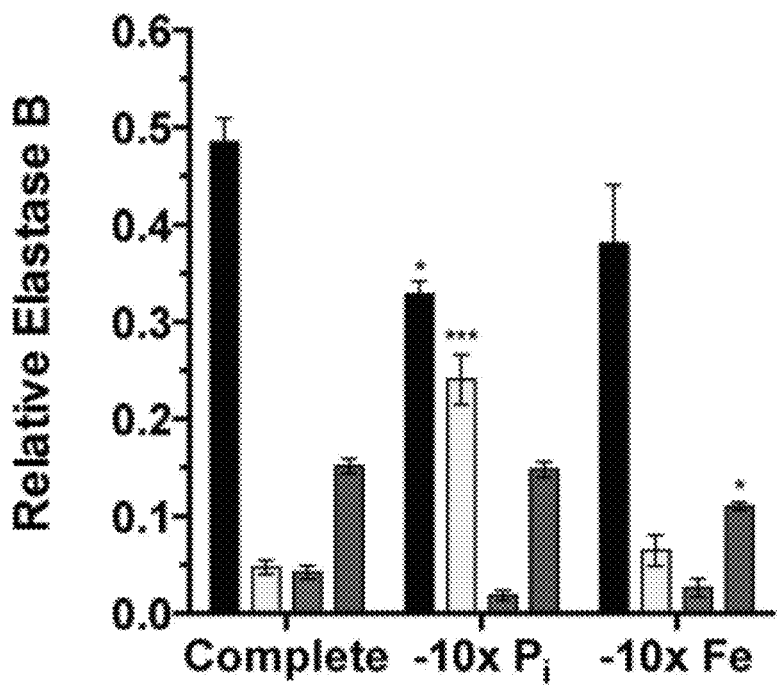
Figure 4D:
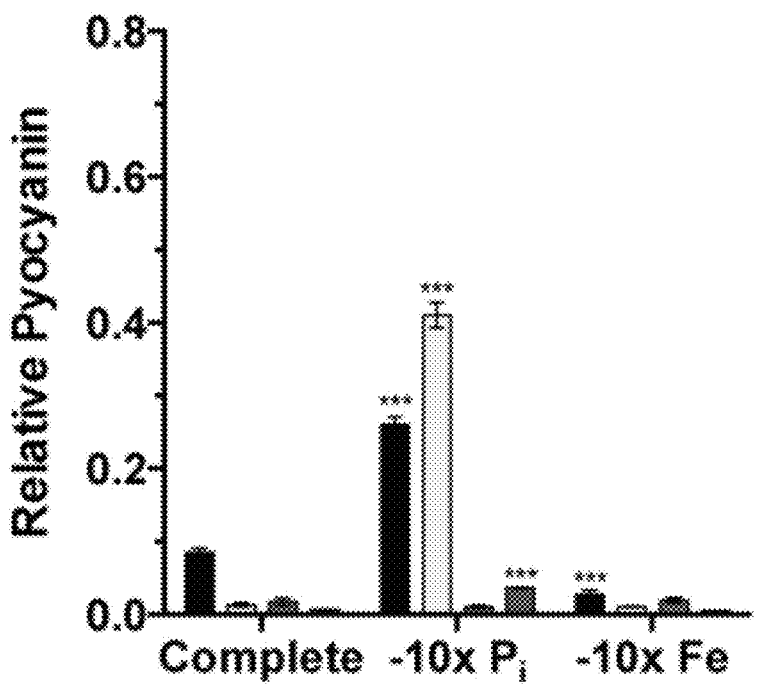
Figure 4E:
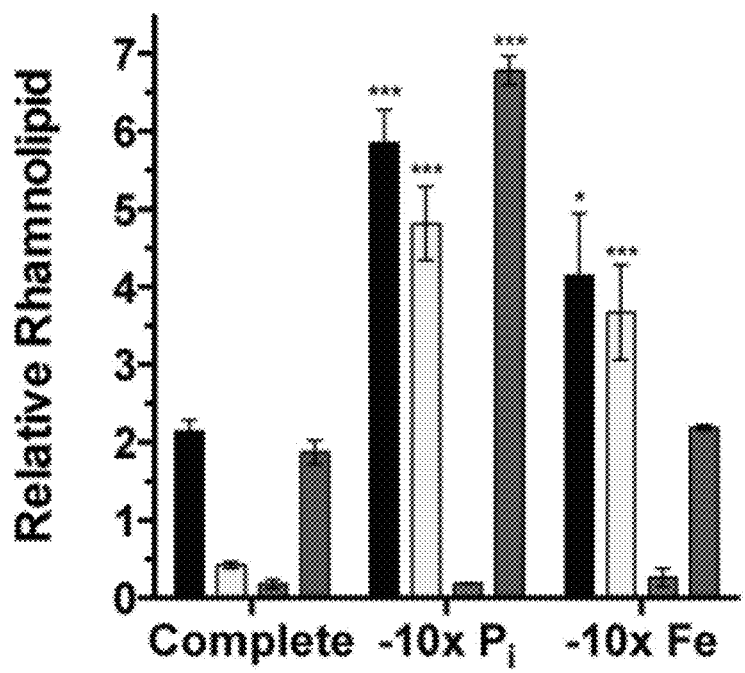
Figure 4F:
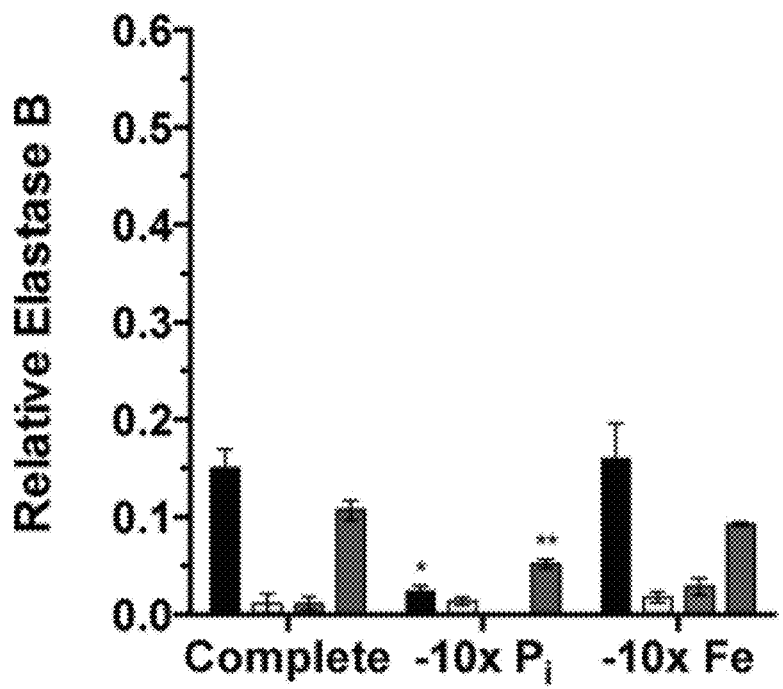

Pyocyanin synthesis is directly regulated by RhUPqs and indirectly by Las through induction of the former systems. Hence, LasR inhibitors are thought to attenuate pyocyanin production through suppression of Rhl and Pqs. Under the most nutrient replete conditions (what we refer herein to as "complete" medium), LasR inhibition by compound 1 eliminated pyocyanin synthesis, but, strikingly, under phosphate poor conditions compound 1 had little to no effect (FIG. 3).

This result indicates that Las does not contribute to pyocyanin production under low phosphate conditions. Instead, activation of Rhl and Pqs, presumably via PhoB, is able to compensate for the loss of Las-dependent induction of these systems in the presence of compound 1 under these conditions.

Rhl and Pqs are required for full virulence in nutrient limiting environments. Having defined one environmental condition where a QS circuit is unessential for virulence, we examined the individual contributions of all three QS circuits in *P. aeruginosa* in additional nutrient conditions that feed into QS activation. Glutamate was replaced in the above MOPS minimal medium with glucose, a carbon source that is disfavored by carbon catabolite repression relative to glutamate in *P. aeruginosa* (FIG. 1A) (Shrout et al., 2006; Rojo, 2010). The effect of iron levels in the MOPS media was also examined because iron is tightly sequestered in most tissues and can influence Pqs activity (FIG. 1A) (Oglesby et al., 2008). WT *P. aeruginosa* and isogenic lasR, rhlR, and pqsR mutants were grown in MOPS Glutamate and MOPS Glucose with or without the iron and phosphate levels diluted 10-fold from the medium, and then quantified the amount of three virulence factors (elastase B, rhamnolipid, and pyocyanin) in the culture supernatant. Each of these virulence factors is closely has been associated in the art with one QS circuit—elastase B with Las, rhamnolipid with Rhl, and pyocyanin with Pqs, but is subject to direct or indirect regulation from all three circuits (FIG. 1B) (Cao et al., 2001; Diggle et al., 2003; Ddziel et al., 2005; Gilbert et al., 2009; Reis et al., 2011; Recinos et al., 2012). These virulence factors, therefore, are a representative sample of the global QS-controlled virulence regulon of *P. aeruginosa*.

WT *P. aeruginosa* exhibits highly distinct virulence profiles under these varied environmental conditions, suggestive of unique QS activity in each medium (FIG. 4A-F). Pyocyanin and elastase B production were higher in MOPS Glutamate, but, congruent with a previous report (Shrout et al., 2006), rhamnolipid synthesis was nearly 10-fold higher when growing on glucose. Further, the QS mutants displayed varying abilities to activate virulence factor production in response to nutrient limitation stress (FIG. 4A-F). For example, the lasR mutant produced no virulence factors in either complete medium, but depletion of phosphate induced elastase B, rhamnolipid, and pyocyanin production, characteristic of Rhl and Pqs activation in this environment (Dekimpe and Ddziel, 2009). Further, low iron concentrations uniquely induced rhamnolipid synthesis in the lasR mutant, suggesting that Rhl responds preferentially to this condition. Notably, rhlR was required for virulence factor production under all conditions tested; nutrient limitation did not induce virulence factor production in the rhlR mutant. Finally, pqsR was essential for full pyocyanin and elastase B production, and nutrient depletion did not induce production of either of these virulence factors beyond levels observed in complete medium in this mutant strain. However, pqsR was only necessary for full rhamnolipid synthesis in low iron media. These data suggest that the Rhl and Pqs systems are required for *P. aeruginosa* to adapt its virulence profile to nutrient limitation stress, while the Las system plays a lesser role.

Example 6

Small Molecule QS Inhibitors have Environment-Dependent Activity

The relative contribution of Rhl and Pqs to virulence in defined nutrient environments was next assessed. The genetic knockouts, discussed above, can provide only limited information because gene deletion destroys the interregulation between QS circuits. A group of small molecules representing some of the most potent synthetic inhibitors of *P. aeruginosa* QS circuits known were assembled. This group included: the LasR antagonist compound 1 (Müh et al., 2006; Moore et al., 2015); the RhlR antagonist compound 2, (Welsh et al., 2015; Eibergen et al., 2015); and the PqsR antagonist compound 4, (Rahme et al.) (FIG. 1B) (Starkey et al., 2014).

Figure 5:
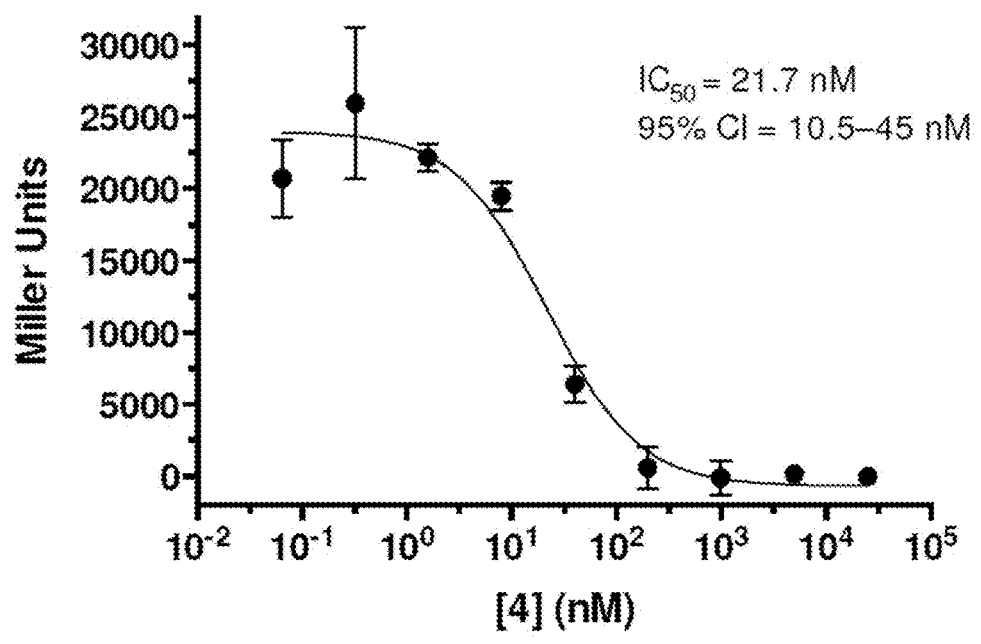
FIG. 5 is a graph that illustrates the PqsR antagonism dose response curve for compound 4 in the *Escherichia coli* PqsR reporter strain. Related to FIGS. 6A and B and 12. See the Examples and Table 1 below for full assay and strain information. Error bars represent the standard error of three biological replicates (n=3). $IC_{50}$ and 95% confidence interval (95% CI) values were calculated using GraphPad Prism software.
Figure 6A:
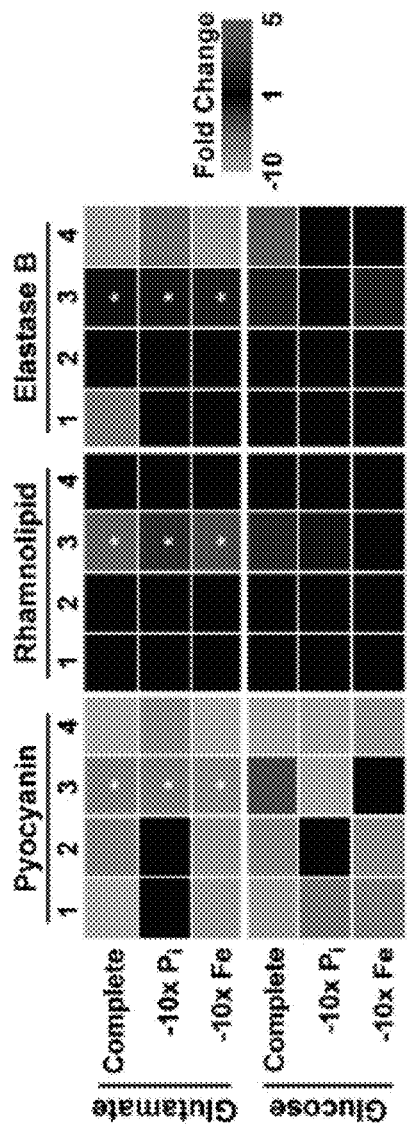
FIGS. 6A and B illustrate that QS modulators have environment-dependent effects on virulence factor production.

Each compound is capable of inhibiting the activity of its target receptor by ≥85% in reporter gene assays (see FIG. 5 and the above references for each compound). WT *P. aeruginosa* cultures treated with each of these compounds were grown in MOPS Glutamate and Glucose media, and production of elastase B, rhamnolipid, and pyocyanin was quantitifed. Each compound had environment-specific activity (FIG. 6A). Chemical inhibition of LasR and RhlR by compounds 1 and 2 resulted in strong pyocyanin inhibition, unless phosphate concentrations were low, but had little to no effect on rhamnolipid and elastase B. Thus, even when Las and Rhl are inhibited in WT *P. aeruginosa*, key virulence factors associated with these systems (i.e., elastaseB and rhamnolipid) are still produced under many conditions. This result suggests that Pqs is involved in the recovery of some Las- and Rhl-associated virulence factor production when the latter systems are inhibited. Accordingly, PqsR antagonism by compound 4 eliminated pyocyanin synthesis under all conditions tested, even low iron and phosphate, and resulted in strong attenuation of elastase B production in MOPS Glutamate. But, like the other compounds, compound 4 failed to inhibit rhamnolipid production. Thus, Pqs inhibition results in attenuation of virulence factor production in nutrient limiting conditions where Las and Rhl antagonists are inactive. These results imply that Pqs is important for adapting virulence factor production to nutrient depletion in WT *P. aeruginosa*.

Figure 7A:
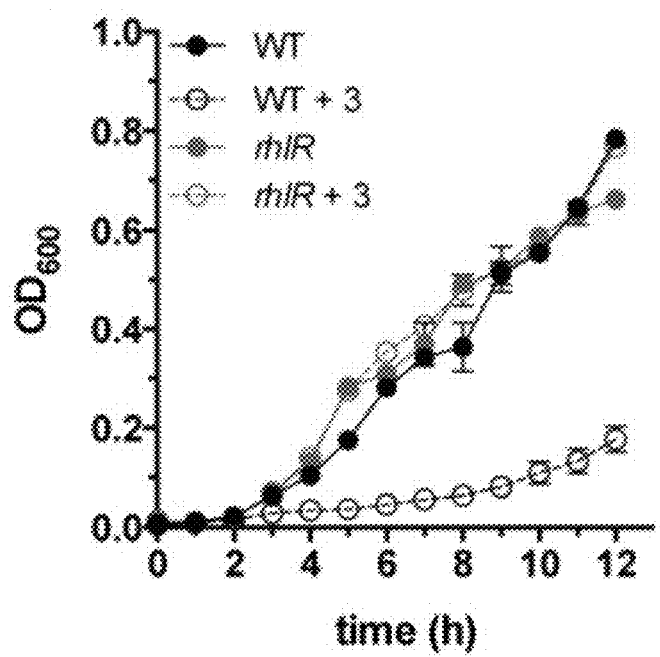
Figure 7B:
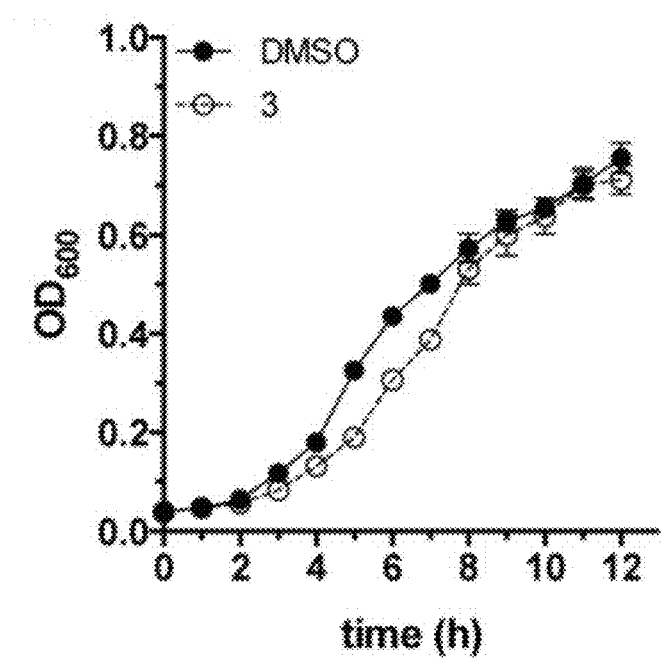
Figure 7C:
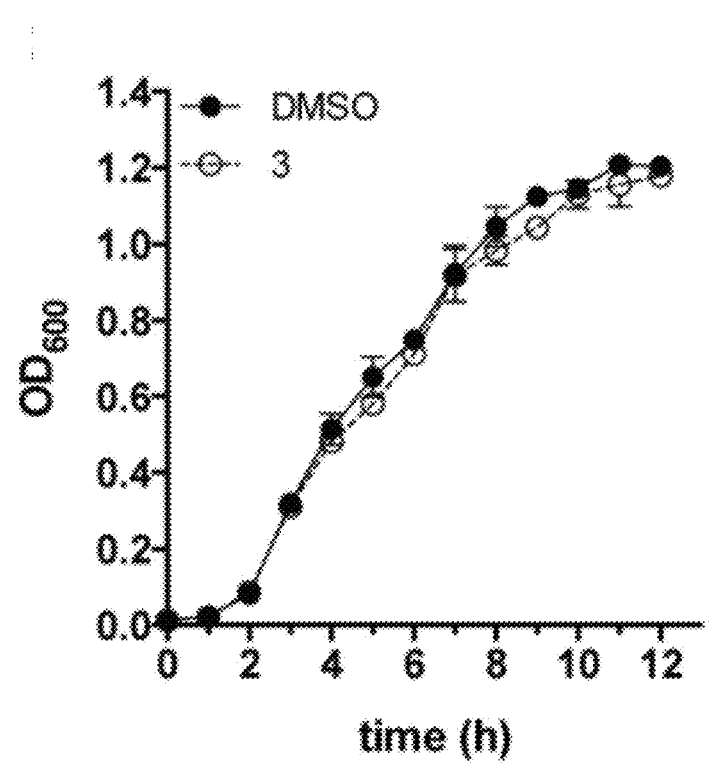
Figure 8A:
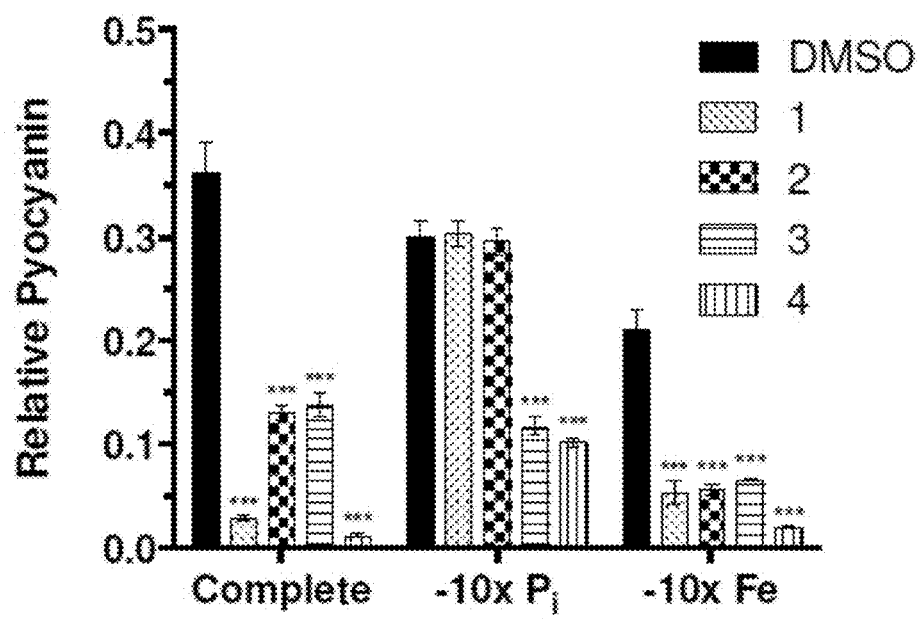
FIGS. 8A-F provide primary pyocyanin, rhamnolipid, and elastase B assay data for single compound screens. Cultures of wild-type *P. aeruginosa* (PAO1) were grown in (FIG. 8A-C) MOPS/Glutamate or (FIGS. 8 D-F) MOPS/Glucose in the presence of the indicated compounds. The final amounts of pyocyanin, rhamnolipid, and elastase B in the supernatant were quantified after 17 h. See Examples for full assay protocols and medium compositions. Final compound concentrations were 100 µM for compounds 1, 2, and 3 and 25 µM for compound 4. Error bars represent the standard error of at least three biological replicates (n≥3). P values were calculated by one-way ANOVA and Dunnett's multiple comparison post-test using GraphPad Prism software. *=p <0.05, =p<0.005, *=p<0.0005.
Figure 8B:
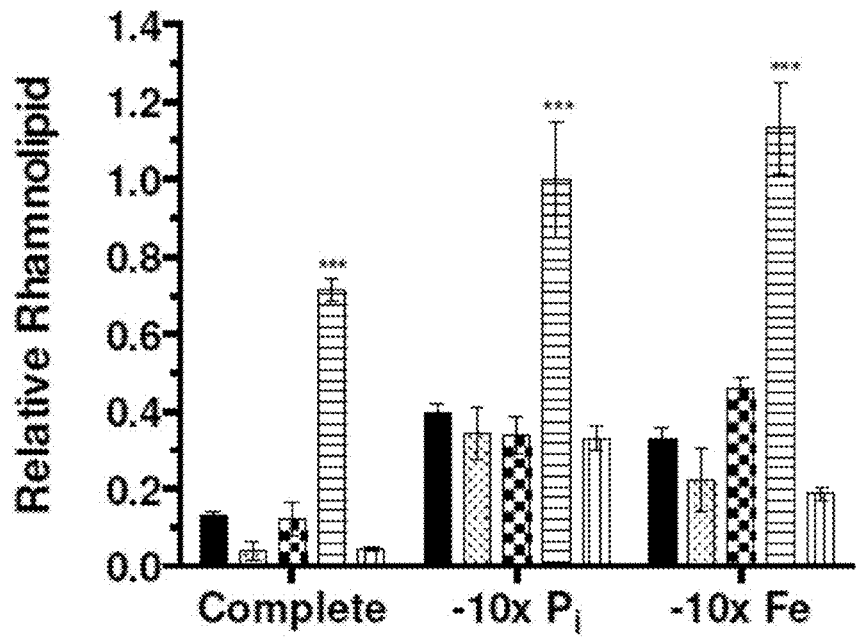
Figure 8C:
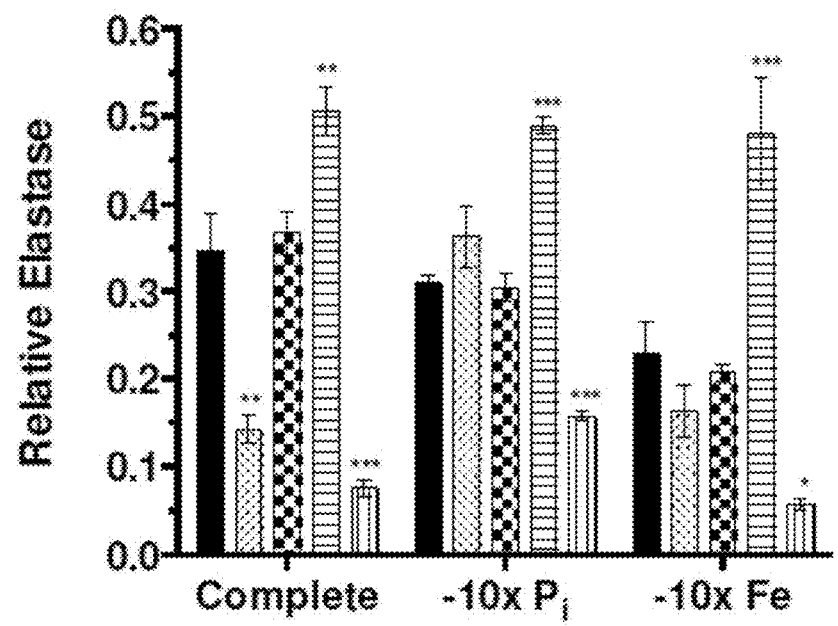
Figure 8D:
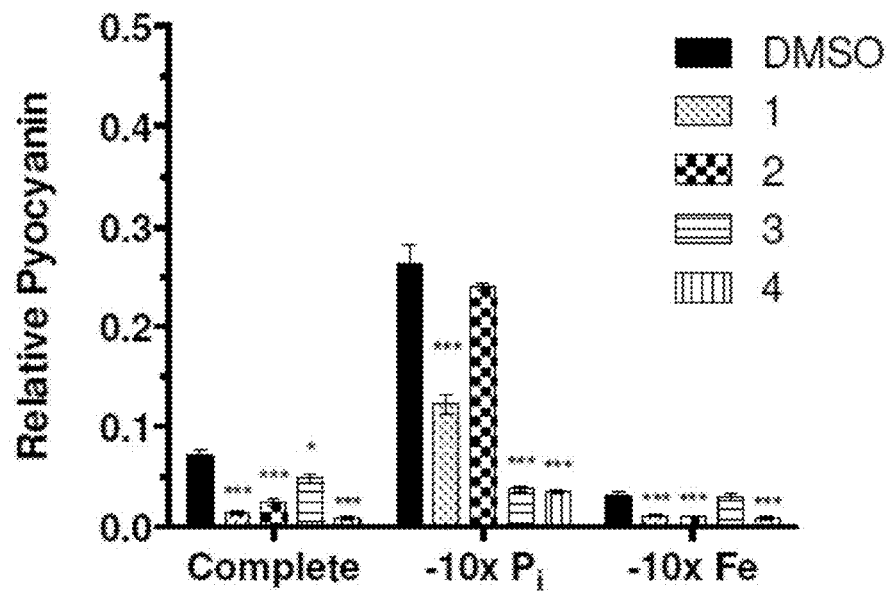
Figure 8E:
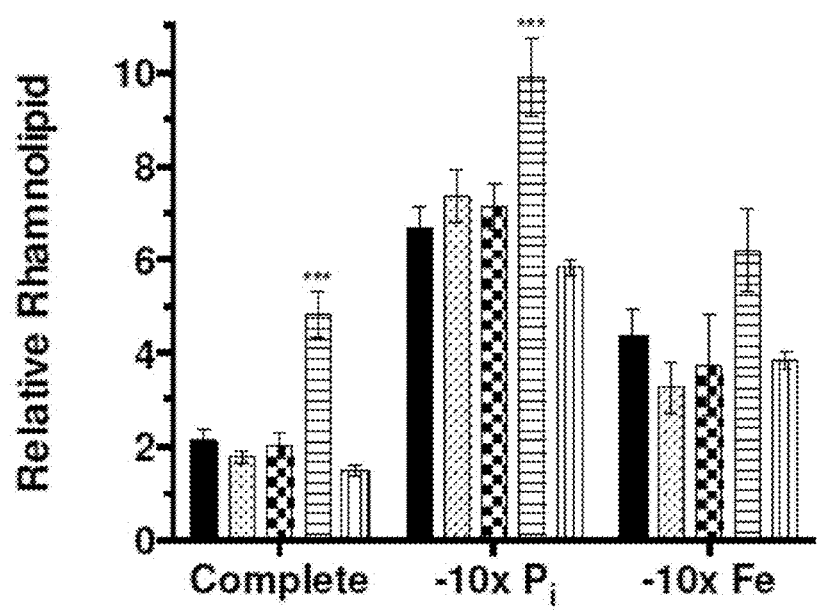
Figure 8F:
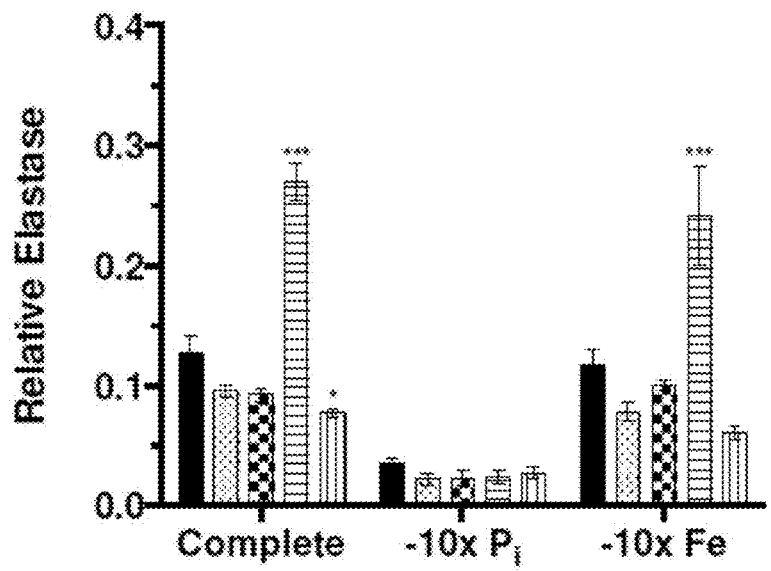
Figure 9A:
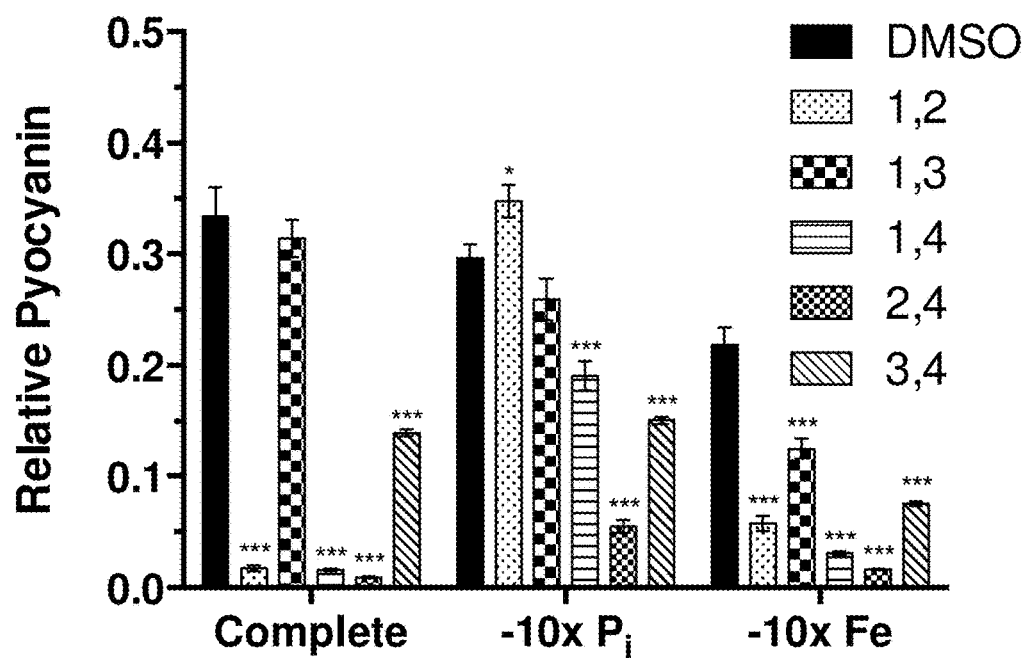
FIGS. 9A-F illustrate primary pyocyanin, rhamnolipid, and elastase B assay data for compound cocktail screens (Related to FIGS. 6A and 6B). Cultures of wild-type *P. aeruginosa* (PAO1) were grown in MOPS Glutamate (FIGS. 9A-C) or MOPS Glucose (FIGS. 9 D-F) in the presence of the indicated compounds. The final amounts of pyocyanin, rhamnolipid, and elastase B in the supernatant were quantified after 17 h. See Examples for full assay protocols and medium compositions. Final compound concentrations were 50 µM for compounds 1, 2, and 3 and 10 µM for compound 4. Error bars represent the standard error of at least three biological replicates (n≥3). P values were calculated by one-way ANOVA and Dunnett's multiple comparison post-test using GraphPad Prism software. *=p<0.05, =p <0.005, *=p<0.0005.
Figure 9B:
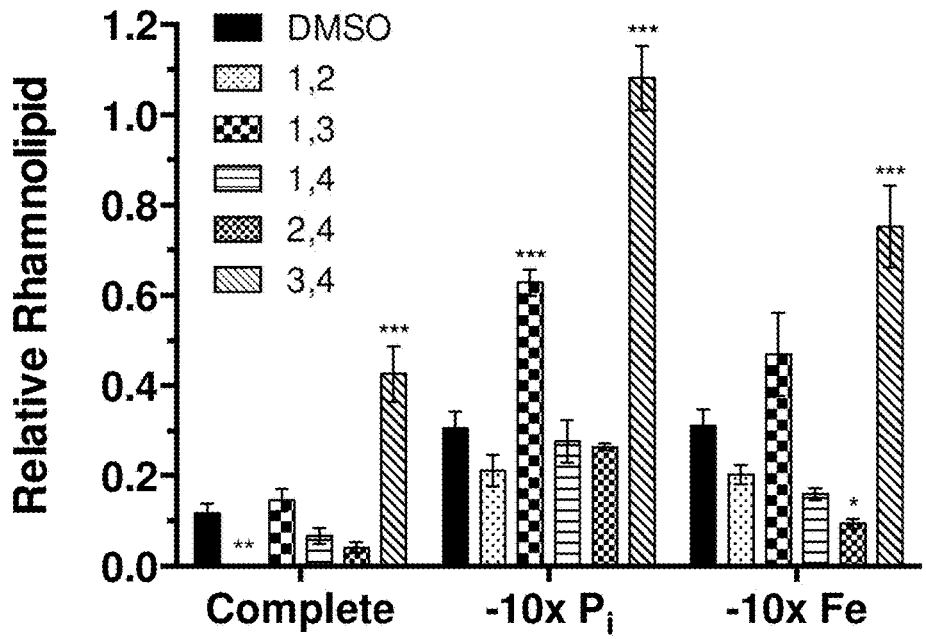
Figure 9C:
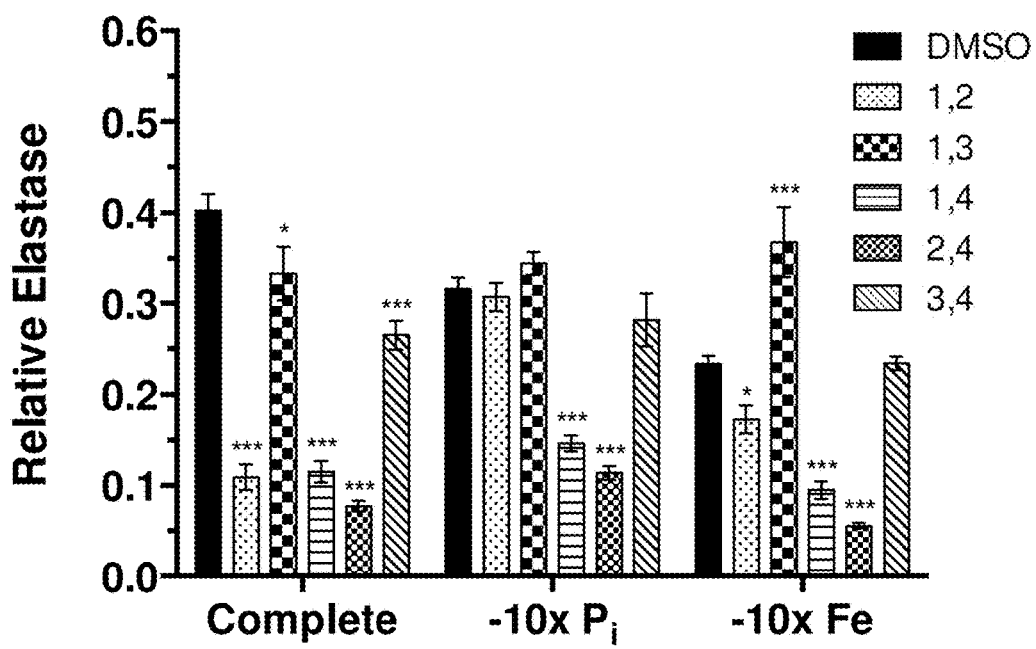
Figure 9D:
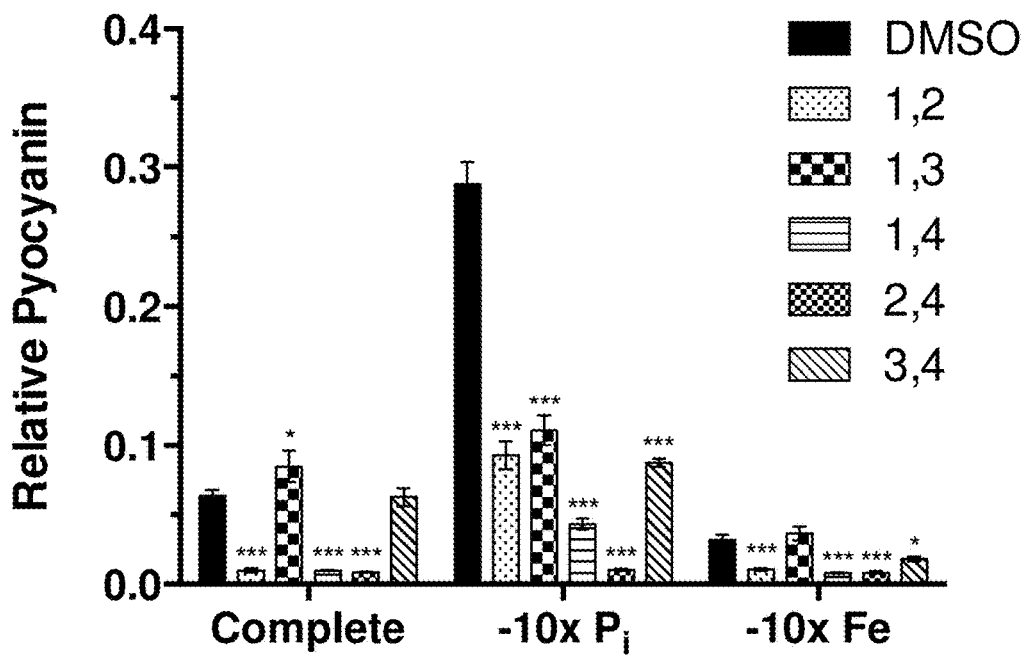
Figure 9E:
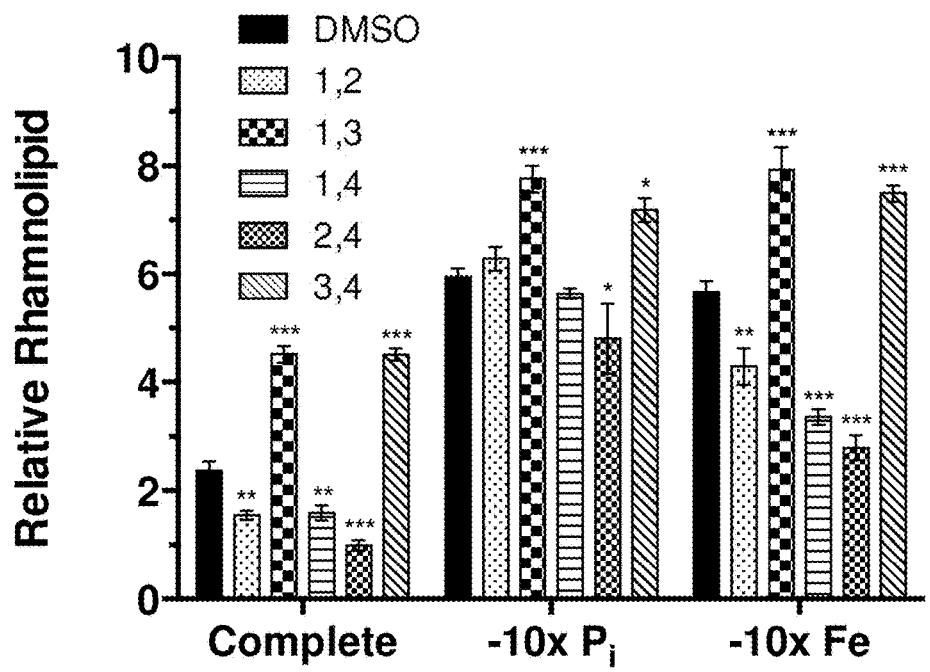
Figure 9F:
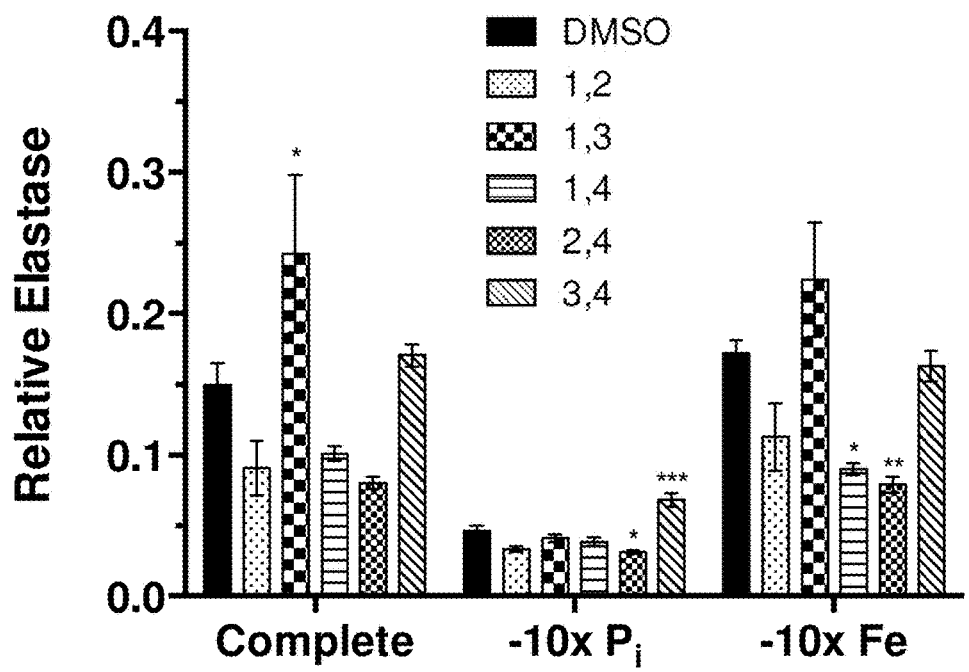
Figure 10A:
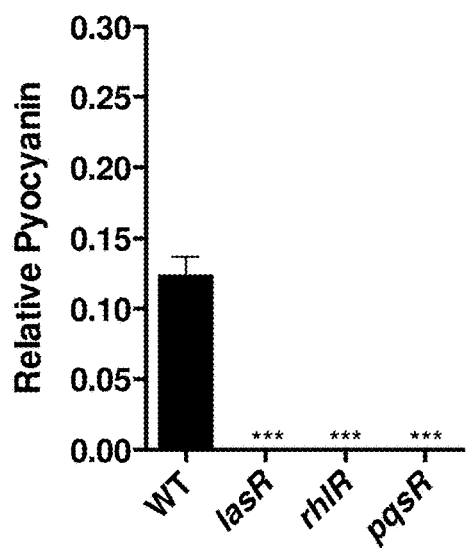
FIGS. 10A-10I illustrate primary pyocyanin, rhamnolipid, and elastase B assay data in SCFM2 (Related to FIG. 12.) Cultures of wild-type *P. aeruginosa* (PAO1) or the QS mutant were grown for 17 h in the presence of the indicated compounds, and the final amounts of pyocyanin, rhamnolipid, and elastase B in the supernatant quantified. See Examples for full assay protocols and media composition. Final compound concentrations in single compound screens were 100 µM for compounds 1, 2, and 3 and 25 µM for compound 4. Final compound concentrations in cocktail screens were 50 µM for compounds 1, 2, and 3 and 10 µM for compound 4. Error bars represent the standard error of at least three biological replicates (n≥3). P values were calculated by one-way ANOVA and Dunnett's multiple comparison post-test using GraphPad Prism software. *=p <0.05, =p<0.005, *=p<0.0005.
Figure 10B:
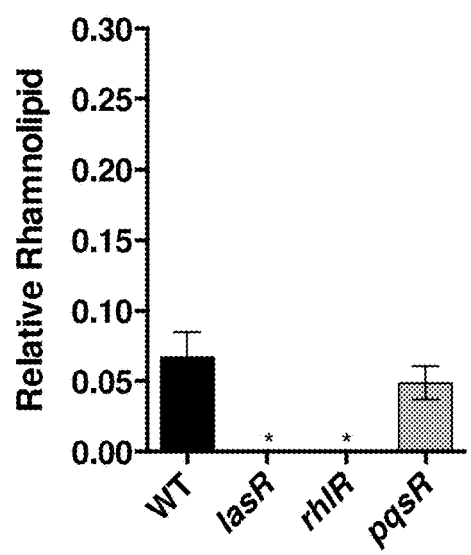
Figure 10C:
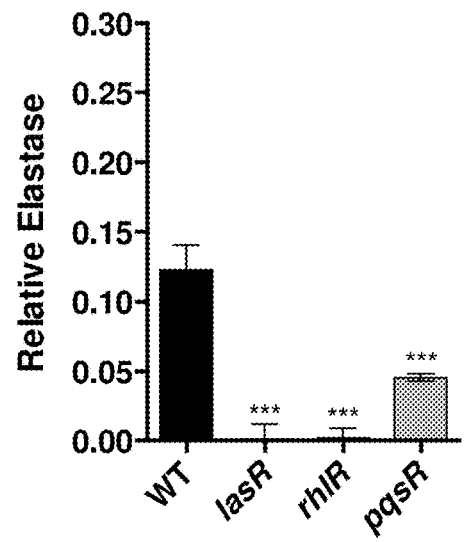
Figure 10D:
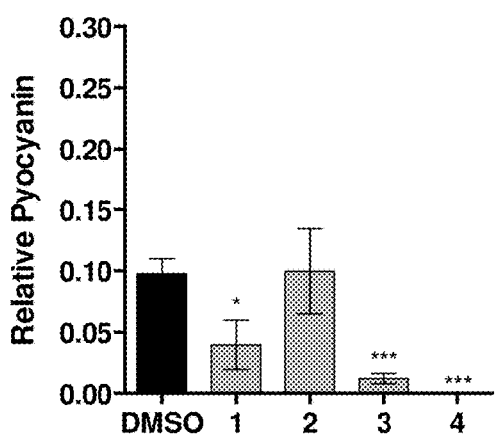
Figure 10E:
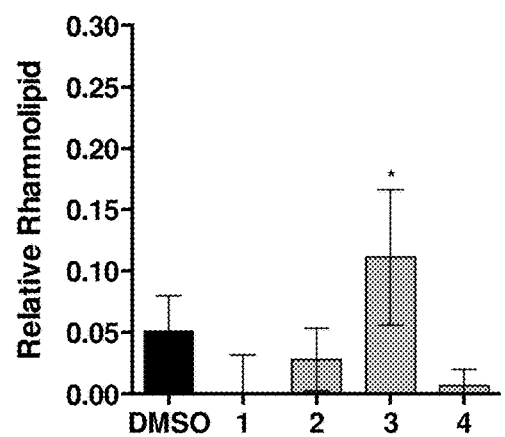
Figure 10F:
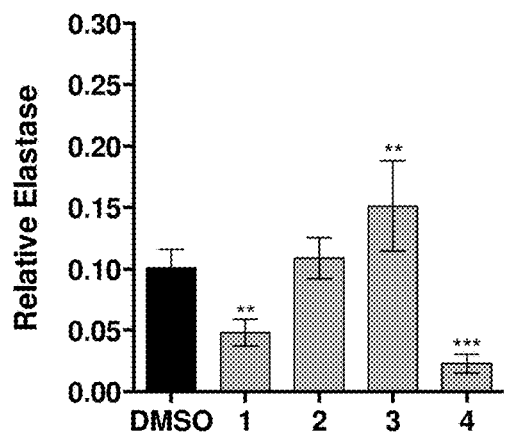
Figure 10G:
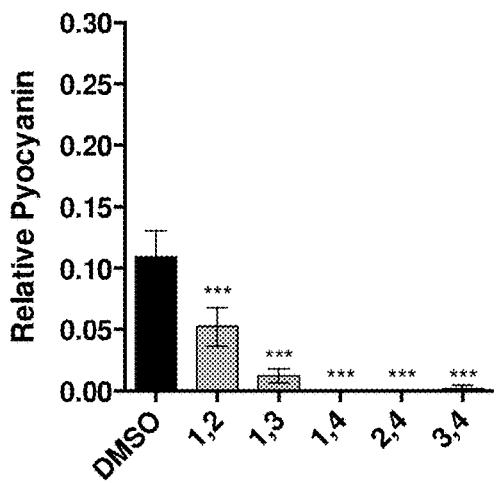
Figure 10H:
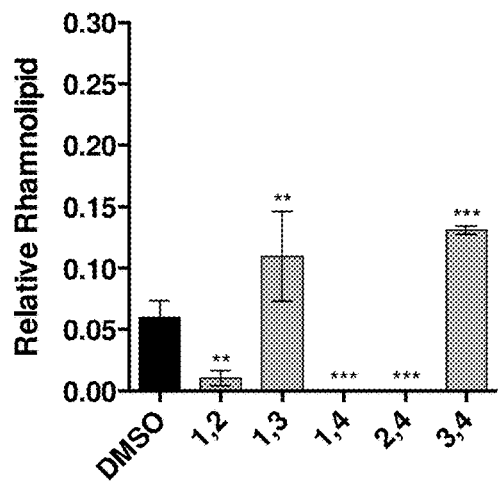
Figure 10I:
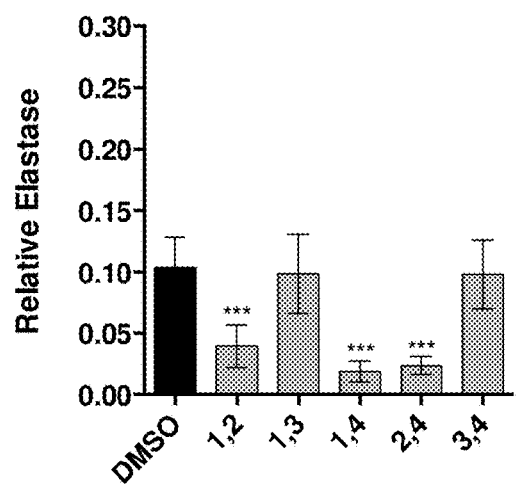
Figure 11A:
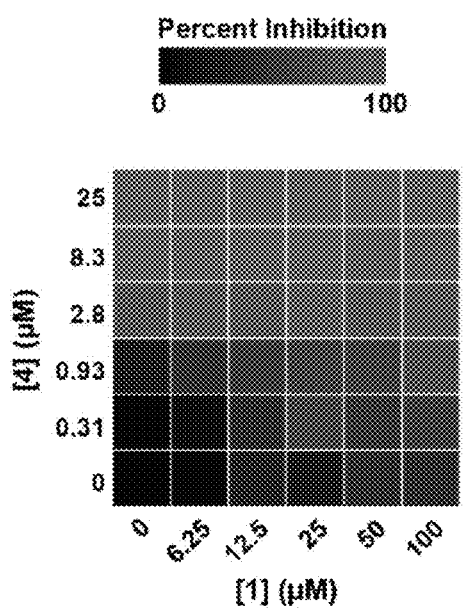
FIGS. 11A-D illustrate checkerboard compound interaction analysis for lead compound cocktails (Related to FIGS. 6A and 6B and 12.) Cultures of wild-type *P. aeruginosa* (PAO1) were grown for 17 h in SCFM2 in the presence of varying amounts of the indicated compounds, and the pyocyanin (FIGS. 11A, 11B) and elastase B (FIGS. 11C, 11D) levels in the final culture supernatant were quantified. See Examples for full assay protocols and media composition. Data are plotted relative to a DMSO-treated control. Error bars represent the standard error of three biological replicates (n=3). No combination of compounds resulted in statistically significant synergistic interactions as determined by calculating fractional inhibitory concentrations (Farha and Brown, 2010).
Figure 11B:
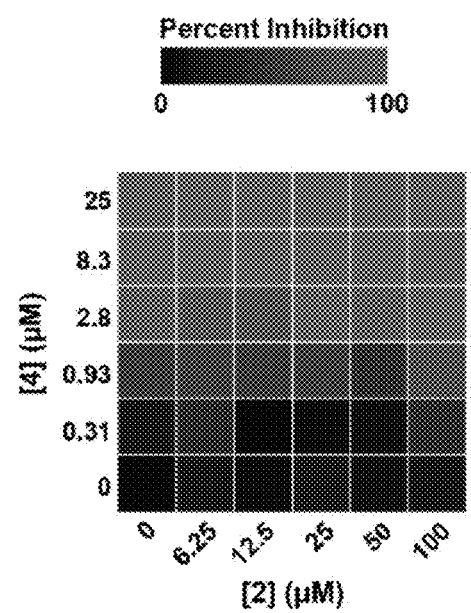
Figure 11C:
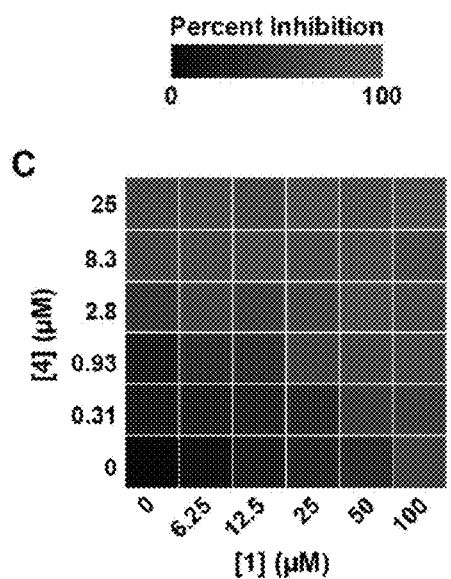
Figure 11D:
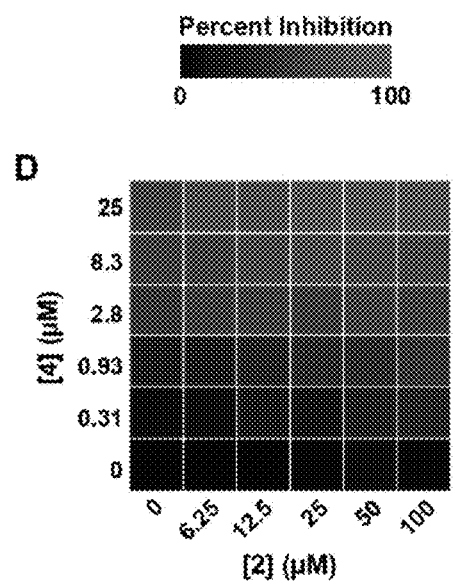

The RhlR agonist compound 3 can inhibit pyocyanin production through Rhl-mediated suppression of Pqs (FIG. 1A) (Welsh et al., 2015). To confirm the importance of Pqs in environmental adaptation, the above experiments were repeated with compound 3. Consistent with the earlier assessment, indirect Pqs suppression by compound 3 blocked pyocyanin production under nearly all of the environmental conditions tested (FIG. 6A). However, RhlR agonism by compound 3 induced additional rhamnolipid and elastase B production. These results, along with our observation that compound 4 cannot inhibit rhamnolipid, indicate that Rhl remains the major contributor to rhamnolipid production in WT *P. aeruginosa* and is essential for pyocyanin production when iron is depleted (FIG. 6A). Intriguingly, it was unexpected found that compound 3 delayed *P. aeruginosa* growth in MOPS Glutamate (FIG. 7A and FIGS. 2A-2D). This delay was only found when *P. aeruginosa* was growing on glutamate, as we did not observe growth effects with other carbon sources (FIGS. 7A and 7B). Further, the effect was dependent on RhlR, as growth of a rhlR-null strain was not delayed by compound 3 (FIG. 7A), and the structurally similar native RhlR ligand, N-butyryl homoserine lactone (BHL), also produced the growth delay (FIGS. 2A-2D). This growth effect is further discussed below.

Example 7

Cocktails of Compounds Improve Efficacy of Inhibition

Figure 6B:
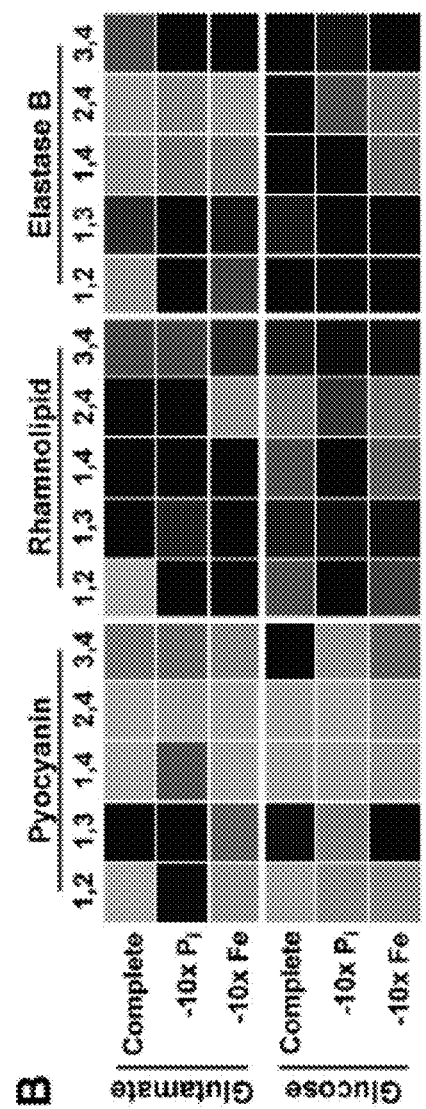
(FIG. 6B) Cocktail screens in MOPS minimal media. *P. aeruginosa* (PAO1) was treated with the indicated compound(s), and the level of pyocyanin, rhamnolipid, and elastase B in the culture supernatant were quantified after 17 h incubation. The resultant values were normalized to cell density ($OD_{600}$) and plotted relative to a DMSO-treated control (see FIG. 8 and FIG. 9 for full assay data). Compound concentrations in single compound screens (FIG. 6A) were 100 μM (compounds 1, 2, and 3) and 25 μM (compound 4) (approximately 10× the $IC_{50}$ or $EC_{50}$ for each compound). Compound concentrations in cocktail screens (B) were 50 μM (compounds 1, 2, or 3) and 10 μM (compound 4). All data represent the mean of at least three biological replicates (n≥3). Colored squares indicate a statistical change ($p<0.05$, calculated by unpaired one way ANOVA using GraphPad Prism software) relative to the DMSO-treated control. An asterisk (*) indicates that growth was delayed by treatment with compound 3 in this medium (see.

The virulence factor production assays above were extended to pairwise combinations of each compound. Certain cocktails (combinations) of QS modulators gave superior activity relative to single compounds (FIG. 6B). By combining a LasR and a RhlR antagonists (e.g., compounds 1 and 2, respectively), greatly improved rhamnolipid inhibition was observed; however, this cocktail was generally inactive under phosphate- and iron-depleted conditions. However, combining a LasR antagonist (e.g., compound 1) or a PqsR antagonist (e.g., compound 4) with an RhlR agonist (e.g., compound 3) did not improve activity. A cocktail of an RhlR antagonist and a PqsR antagonist (e.g. compounds 2 and 4, respectively) proved to be the best combination in these screens. With this combination, we observed no pyocyanin production under any condition and significantly improved elastase B and rhamnolipid inhibition in low phosphate and, particularly, low iron media. This effect appears to be additive as checkerboard analysis did not reveal synergistic interactions between compounds 2 and 4 (FIG. 11A-F). Together, these results provide additional evidence that Rhl and Pqs are important for *P. aeruginosa* to respond to nutrient depletion. Furthermore, they demonstrate that small molecule cocktails targeting multiple QS receptors provide increased attenuation of virulence factor production in nutritional environments where single compounds are ineffective.

Example 8

Studies in Simulated Cystic Fibrosis (CF) Sputum

Figure 12:
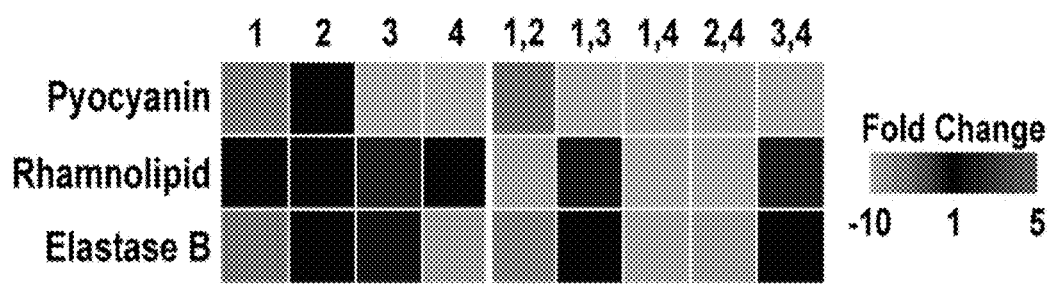
FIG. 12 illustrates that QS modulators inhibit virulence factor production in simulated cystic fibrosis sputum (SCFM2). *P. aeruginosa* (PAO1) was treated with the indicated compound(s), and the level of pyocyanin, rhamnolipid, and elastase B in the culture supernatant were quantified after 17 h incubation (see FIG. 11 for full assay data). Compound concentrations in single compound screens were 100 µM for (compounds 1, 2, and 3) and 25 µM for compound 4. Compound concentrations in cocktail screens were 50 µM for compounds 1, 2, or 3 and 10 µM for compound 4. All data represent the mean of at least three biological replicates (n≥3). Colored squares indicate a statistical change (p<0.05, calculated by unpaired one way ANOVA using GraphPad Prism software) relative to the DMSO-treated control.

Experiments in minimal media provided valuable insights into the environmental requirements for QS circuit activity (and inhibition). Assays were conducted in more infection-relevant environments to assess compound efficacy. Recently, a synthetic CF sputum medium (SCFM2) that accurately mimics the nutrient environment of the airways of CF patients was reported (Turner et al., 2015). The fitness requirements of natural CF sputum are recapitulated in this medium, validating it as an in vitro CF model. The nutrient composition of SCFM2 consists, primarily, of amino acid carbon sources with phosphate and iron concentrations that are similar to complete MOPS media. Thus, based on data discussed above, we predicted that *P. aeruginosa* would have a virulence profile in SCFM2 similar to that in MOPS Glutamate. Congruent with this prediction, WT *P. aeruginosa* was found to produce similar amounts of pyocyanin, rhamnolipid, and elastase in SCFM2 as in MOPS Glutamate (FIG. 10). In addition, the lasR mutant strain did not produce any pyocyanin, rhamnolipid, or elastase B, consistent with the relatively high phosphate and iron levels in SCFM2 (FIG. 10). Based on these results, it was considered that the combinations of representative example compounds would display similar activities in SCFM2. Indeed, a combination of a Las R antagonist and a PqsR antagonist (e.g., compounds 1 and 4) had nearly identical effects on virulence factor production in SCFM2 as in MOPS/Glutamate (FIG. 12). Likewise, combining a PqsR antagonist (e.g., compound 4) with a Las R antagonist (e.g., compound 1) or a RhlR antagonist (e.g., compound 2) inhibited nearly all pyocyanin, rhamnolipid, and elastase B production in SCFM2. The only difference observed between the MOPS/Glutamate and SCFM2 data was that the RhlR antagonist (compound 2) when used alone did not attenuate pyocyanin in SCFM2. However, the additional rhamnolipid inhibition observed when the RhlR antagonist (e.g., compound 2) is combined with a Las R antagonist (e.g., compound 1) or a PqsR antagonist (e.g., compound 4) in SCFM2 suggests that Rhl, much like in complete MOPS/Glutamate, still serves as an important regulator of virulence in this medium. Thus, the effectiveness of certain small molecule modulators and certain combinations of small molecule modulators in an environment commonly encountered by *P. aeruginosa* in infection (CF environment) has been demonstrated.

Example 9

Determination of Percent LasR, RhlR, and QscR Inhibition and Activation

Figure 13A:
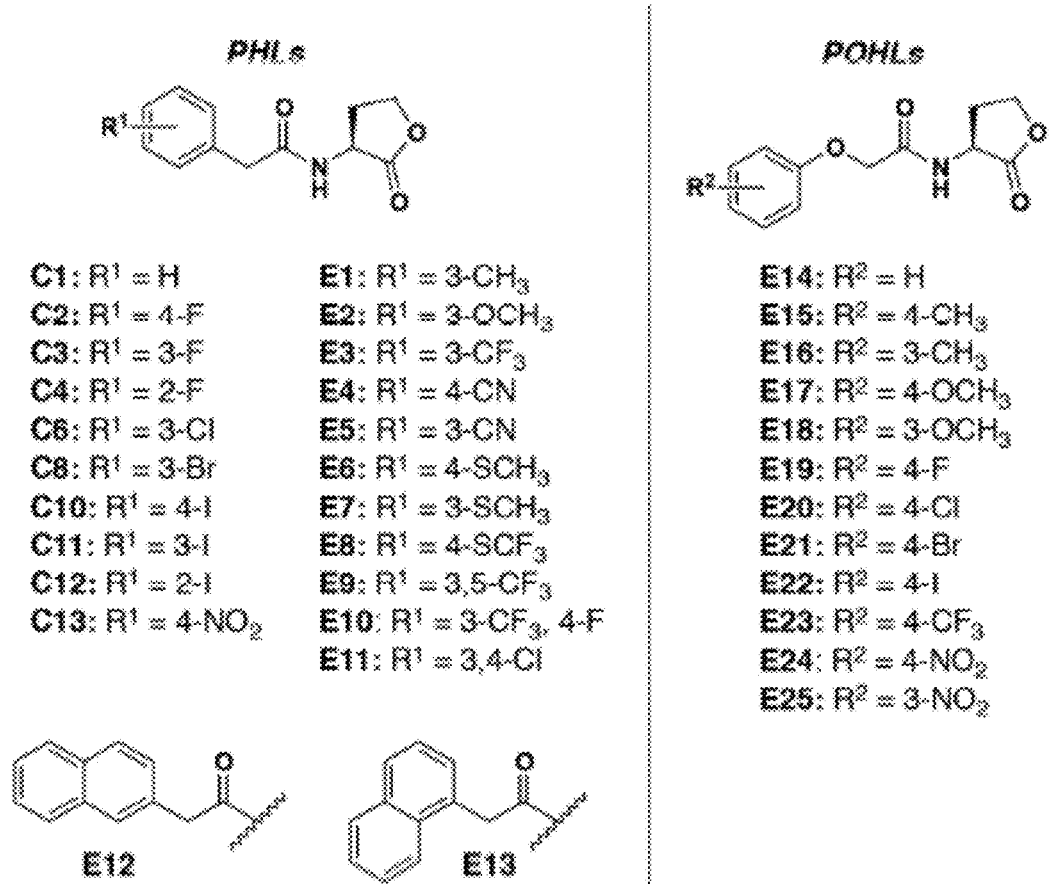
FIGS. 13A and 13B provide a list and structures of exemplary QS modulators which are non-native AHL compounds. Most of the illustrated compounds are subdivided into a PHL group, a POHL group and a PPHL group, where the structural relationship within the groups are indicated. Seceral additional QS modulation not classified in the listed groups are also illustrated. Additional structures of modulators may be found in Welsh et al., 2015; Moore et al., 2015 and Eibergen et al., 2015, each of which is incorporated by reference herein in its entirety for descriptions of such modulators.
Figure 13B:
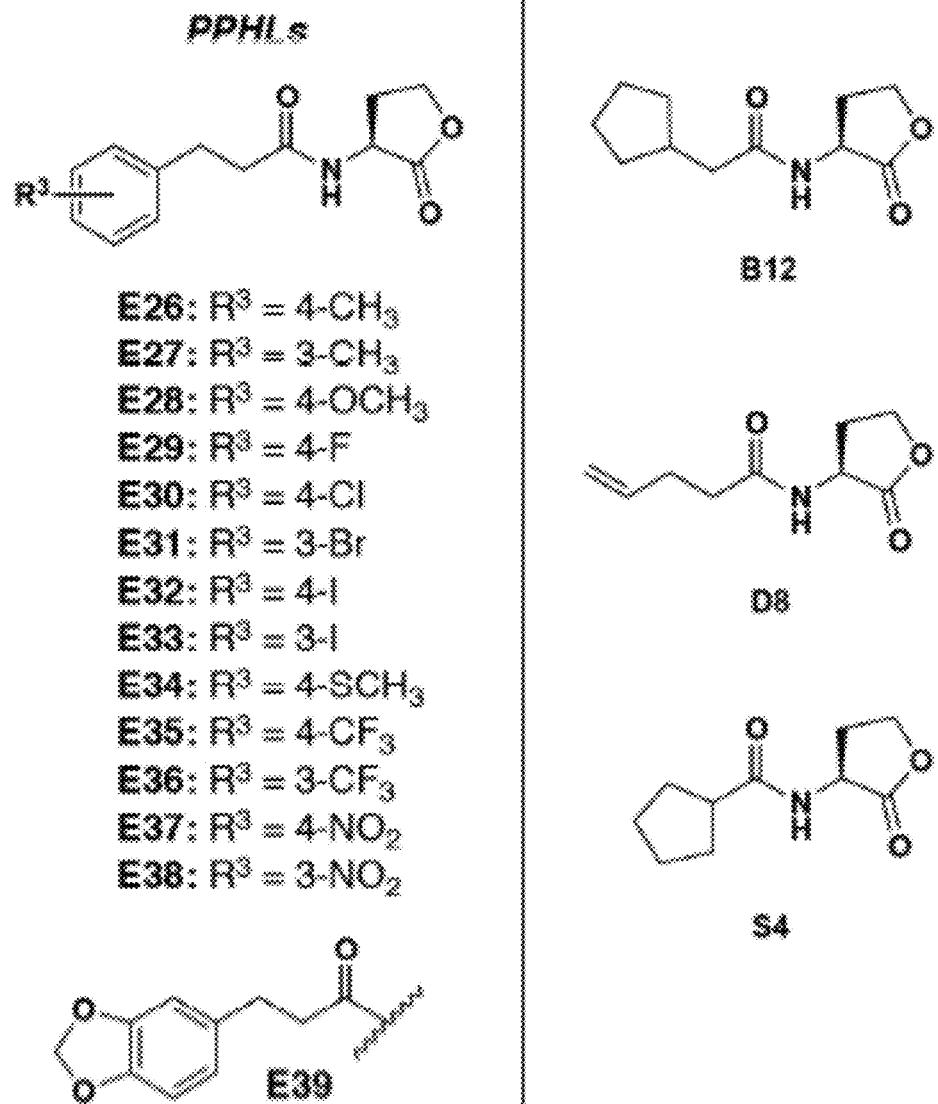

Table 2 provides percent inhibition (antagonism) data for three different QS systems LasR, RhlR and QscR for exemplary compounds in FIGS. 13A and 13B. This example is described in Eibergen et al., 2015, which is incorporated by reference herein for all description regarding assays for percent inhibition and activation. Table 3 provides percent activation (agonism) data for three different QS systems LasR, RhlR and QscR for exemplary compounds in FIGS. 13A and 13B.

The non-native AHLs examined in this example were synthesized and purified as described previously. (see Mattmann et al., 2011; Geske et al., 2007; Geske et al., 2008a; Geske et al., 2008b; and Mattmann et al., 2008). OdDHL was purchased from Sigma-Aldrich and BHL was purchased from Cayman Chemical Company. Chlorophenol red-beta-d-galactopyranoside (CPRG), the substrate for the beta-galactosidase assays, was purchased from Roche. Stock solutions of compounds were prepared in DMSO (at 100 mm) and stored at −20° C. in sealed vials. The amount of DMSO used in small-molecule screens did not exceed 1% (v/v). All synthetic compounds were tested in triplicate, and 3 separate trials were performed on unique cultures. No compound had an effect on bacterial growth over the concentrations tested, as gauged by monitoring OD600 over the time course of the assays. $IC_{50}$ and $EC_{50}$ values were calculated with GraphPad Prism software (v. 4.0) by using a variable slope sigmoidal curve fit.

Construction of pSC11-Q: A 348 bp fragment spanning the upstream region of PA1897 (¢304 to +43 relative to the PA1897 translationalstart codon) was amplified from plasmid pJL101*by using primers 5'-GAATAT <u>GGATCC</u> TCTCTC CGCAGA TACCTG-3' (BamHI site underlined) SEQ ID NO:5 and 5'-GCTATT <u>GAATTC</u> TGAAGA TGAATA GCGCCAC-3' (EcoRI site underlined) SEQ ID NO:6. The PCR-generated fragment was digested with EcoRI and BamHI and subsequently ligated into EcoRI/BamHI-digested pPROBE-KT to generate pPROBE-KQ2. From this plasmid, a 340 bp fragment spanning the upstream region of PA1897 (−300 to +39 relative to the PA1897 translational start site) was amplified by using:

5'-CAGATT <u>GTCGAC</u> TCTCTC CGCAGATACC-3' (SalI site underlined) SEQ ID NO:7 and 5'-CAGCTA <u>GGATCC</u> GAAGATGAATAG CGCC-3' (BamHI site underlined) SEQ ID NO:8. The PCR-generated fragment was digested with SalI and BamHI and subsequently ligated into SalI/BamHI-digested pSC11 to generate pSC11-Q.

*E. coli* reporter gene assays: Primary assays for RhlR, LasR, and QscR activity in *E. coli* JLD271 reporter (beta-galactosidase) strains were performed as reported by Welsh et al. 2015, with the following modifications:

For all primary and dose-response antagonism assays, the concentration of native ligand utilized was approximately equal to its $EC_{50}$ value in each bacterial reporter strain. For RhlR, LasR, and QscR primary antagonism assays, synthetic ligand (100 mm) was screened against BHL (10 mm), OdDHL (2 nm), and OdDHL (15 nm), respectively. For RhlR, LasR, and QscR primary agonism assays, synthetic compound (100 mm) was screened alongside and compared to the natural ligand (900 mm BHL or 100 mm OdDHL) for the receptor. As part of the beta-galactosidase assay protocol, plates to which CPRG substrate had been added were incubated at either 25° C. (LasR assay) or 30° C. (RhlR and QscR assays) until positive control wells developed a deep red color (10 min for LasR, 30 min for RhlR, and 60 min for QscR). Dose-response reporter gene assays were performed according to these protocols by using varying concentrations of compound.

P. aeruginosa reporter assays: Primary assays for RhlR activity in P. aeruginosa were performed as previously reported for LasR, [33] with the following modifications: OdDHL was added to the subculture to a final concentration of 100 nm immediately before it was dispensed into plates to induce expression of RhlR. For RhlR antagonism assays, synthetic ligand (100 mm) was screened against BHL at its $EC_{50}$ (30 mm). For RhlR agonism assays, synthetic ligand (100 mm) was screened alongside and compared to BHL (at 900 mm) for the system. Dose-response reporter gene assays were performed according to these protocols by using various concentrations of compound.

TABLE 2

Percent LasR, RhlR and QscR inhibition

| Compound | Inhibition [%] | | |
|---|---|---|---|
| | LasR[a] | RhlR[b] | QscR[c] |
| B4 | 15 | 66 | 37 |
| C10 | 58 | 84 | −79 |
| C13 | 91 | 60 | 14 |
| C16 | 76 | 66 | 74 |
| C19 | 81 | 87 | 64 |
| C20 | 93 | 86 | 26 |
| D15 | −80 | 61 | 4 |
| E6 | 85 | 78 | 24 |
| E8 | 23 | 65 | 40 |
| E11 | 28 | 62 | 15 |
| E12 | 81 | 77 | 60 |
| E15 | 84 | 75 | 33 |
| E17 | 83 | 66 | 36 |
| E21 | 31 | 66 | 20 |
| E22 | −9 | 74 | 18 |
| E23 | −49 | 64 | 22 |
| E34 | −52 | 62 | −190 |
| S6 | 56 | 69 | 34 |

[a]Compounds were evaluated at 100 mm against 2 nm OdDHL in E. coli beta-galactosidase reporter strain JLD271/pJN105L/pSC11. Activity for untreated culture set to 100%. All assays were performed in triplicate. Error = ±10%. Negative values indicate receptor agonism;
[b]Compounds were evaluated at 100 mm in the presence of 10 mm BHL. Untreated culture was set to 100%. All assays were performed in triplicate. Error = ±10%. Selected percent inhibittion data reproduced from Welsh et al. 2015. Bold values indicate activities that confer RhlR-selective antagonism;
[c]Compounds were evaluated at 100 mm against 15 nm OdDHL in E. coli beta-galactosidase reporter strain JLD271/pJN105Q/pSC11-Q. Activity for untreated culture was set to 100%. All assays were performed in triplicate. Error = ±10%.

TABLE 3

Percent LasR, RhlR, an QscR Activation

| Compound | Activation [%] | | |
|---|---|---|---|
| | LasR[a] | RhlR[b] | QscR[c] |
| B12 | −10 | 79 | 12 |
| C1 | −3 | 84 | 3 |
| C2 | 12 | 71 | 10 |
| C3 | −2 | 79 | 13 |
| C4 | −4 | 66 | 0 |

TABLE 3-continued

Percent LasR, RhlR, an QscR Activation

| Compound | Activation [%] | | |
|---|---|---|---|
| | LasR[a] | RhlR[b] | QscR[c] |
| C6 | 30 | 82 | 30 |
| C8 | 44 | 80 | 33 |
| C11 | 56 | 63 | 34 |
| C12 | −4 | 70 | 5 |
| D8 | 26 | 81 | 13 |
| E1 | 21 | 69 | 29 |
| E2 | 23 | 86 | 26 |
| E5 | 62 | 67 | 34 |
| E7 | 32 | 70 | 24 |
| E30 | 53 | 64 | 79 |
| E31 | 71 | 65 | 58 |
| E37 | 22 | 69 | 65 |
| S4 | −4 | 91 | 4 |

[a]Compounds were evaluated at 100 mm in E. coli beta-galactosidase reporter strain JLD271/pJN105L/pSC11. Activity for 100 mm OdDHL was set to 100%. All assays were performed in triplicate. Error = ±10%.
[b]Compounds were evaluated at 100 mm. Activity for 900 mm BHL was set to 100%. All assays were performed in triplicate. Error = ±10%. Selected percent activation data reproduced from Welsh et al., 2015.
[c]Compounds were evaluated at 100 mm in E. coli beta-galactosidase reporter strain JLD271/pJN105Q/pSC11-Q. Activity for 100 mm OdDHL set to 100%. All assays were performed in triplicate. Error = ±10%.

Example 10

Exemplary Thiolactone of Formula VII

The synthesis of thiolactones of formula VII is exemplified by the synthesis of Compound RN22:

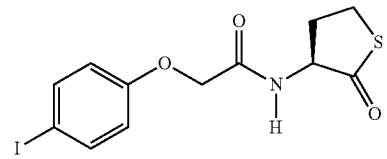 [SMILES: O=C(COc1ccc(I)cc1)N[C@H]1CCSC1=O]

This compound was synthesized using previously established solution-phase, EDC-mediated amide coupling procedures (Morkunas et al., 2012). The two starting materials, 4-iodophenoxyacetic acid and 1,4-thiolactone hydrochloride, were purchased from Sigma Aldrich. The final product was purified using flash column chromatography in a EtOAc/Hex gradient, and purity was checked via NMR and Mass spectrometry (MS). This example is found in U.S. provisional application 62/376,291, Aug. 17, 2016.

Characterization Data: $^{1}$H NMR (500 MHz, CDCl$_3$) δ 7.70-7.48 (m, 2H), 6.94 (d, J=7.6 Hz, 1H), 6.77-6.68 (m, 2H), 4.61 (dt, J=13.2, 6.7 Hz, 1H), 4.50 (d, J=2.6 Hz, 2H), 3.39 (td, J=11.8, 5.1 Hz, 1H), 3.32-3.27 (m, 1H), 3.02-2.88 (m, 1H), 2.01 (qd, J=12.4, 7.0 Hz, 1H); $^{13}$C NMR (126 MHz, CDCl$_3$) δ 204.7, 168.4, 157.0, 138.8, 117.2, 84.9, 67.4, 59.1, 31.8, 27.7; Expected [M+H]$^+$: 377.9655, observed: 377.9650; IR (cm$^{-1}$): 3282, 2974, 2926, 2858, 1696, 1655, 1536, 1233

Antagonism activity data for thiolactone compound RN22 were collected as described above in the E. coli reporter and the P. aeruginosa reporter. For the E. coli reporter the results were: IC$_{50}$: 19.6 μM and 95% CI: 14.3 μM-26.9 μM. For the P. aeruginosa reporter the results were: IC$_{50}$: 31.4 μM and 95% CI: 19.6 μM-50.4 μM. Compound RN22 is amongst the most potent RhlR inhibitors (IC$_{50}$=31 μM in P. aeruginosa). For context, the native ligand QS ligand for RhlR has an $EC_{50}$ of ~8 µM, so compound RN22 can block the activity of the native ligand by 50% at a less than 4-fold higher concentration.

REFERENCES

Allen, R. C., Popat, R., Diggle, S. P. & Brown, S. P. (2014). Targeting virulence: can we make evolution-proof drugs? Nat. Rev. Microbiol., 12, 300-308.

Amara, N., Krom, B. P., Kaufmann, G. F. & Meijer, M. M. (2011). Macromolecular inhibition of quorum sensing: enzymes, antibodies, and beyond. Chem. Rev., 111, 195-208.

Balasubramanian, D., Schneper, L., Kumari, H. & Mathee, K. (2013). A dynamic and intricate regulatory network determines Pseudomonas aeruginosa virulence. Nucleic Acids Res., 41, 1-20.

Cabeen, M. T. (2014). Stationary phase-specific virulence factor overproduction by a lasR mutant of Pseudomonas aeruginosa. PLoS ONE, 9, e88743.

Camilli, A. & Bassler, B. L. (2006). Bacterial small-molecule signaling pathways. Science, 311, 1113-1116.

Cao, H., Krishnan, G., Goumnerov, B., Tsongalis, J., Tompkins, R. & Rahme, L. G. (2001). A quorum sensing-associated virulence gene of Pseudomonas aeruginosa encodes a LysR-like transcription regulator with a unique self-regulatory mechanism. Proc. Natl. Acad. Sci. U.S.A, 434 98, 14613-14618.

Cegelski, L., Marshall, G. R., Eldridge, G. R. & Hultgren, S. J. (2008). The biology and future prospects of antivirulence therapies. Nat. Rev. Microbiol., 6, 17-27.

Chen, G.; Swem, L. R.; Swem, D. L.; Stauff, D. L.; O'Loughlin, C. T.; Jeffrey, P. D.; Bassler, B. L.; Hughson, F. M. (2011) A strategy for antagonizing quorum sensing. Mol. Cell 42, 199-209.

Costas, C.; Lopez-Puente, V.; Bodelon, G.; Gonzalez-Bello, C.; Perez-Juste, J.; Pastoriza-Santos, I.; Liz-Marzan, L. M. (2015) Using surface enhanced Raman scattering to analyze the interactions of protein receptors with bacterial quorum sensing modulators. ACS Nano 9, 5567-5576.

Cugini, C., Calfee, M. W., Farrow, J. M., Morales, D. K., Pesci, E. C. & Hogan, D. A. (2007). Farnesol, a common sesquiterpene, inhibits PQS production in Pseudomonas aeruginosa. Mol. Microbiol., 65, 896-906.

D'Argenio, D. A., et al. (2007). Growth phenotypes of Pseudomonas aeruginosa lasR mutants adapted to the airways of cystic fibrosis patients. Mol. Microbiol., 64, 512-533.

Davenport, P., Griffin, J. L. & Welch, M. (2015). Quorum sensing is accompanied by global metabolic changes in the opportunistic human pathogen, Pseudomonas aeruginosa. J. Bacteriol., 441 197, 2072-2082.

Dekimpe, V. & Déziel, E. (2009). Revisiting the quorum-sensing hierarchy in Pseudomonas aeruginosa: the transcriptional regulator RhlR regulates LasR-specific factors. Microbiology, 444 155, 712-723.

Déziel, E., Gopalan, S., Tampakaki, A. P., Lépine, F., Padfield, K. 445 E., Saucier, M., Xiao, G. & Rahme, L. G. (2005). The contribution of MvfR to Pseudomonas aeruginosa pathogenesis and quorum sensing circuitry regulation: multiple quorum sensing-regulated genes are modulated without affecting lasRI, rhlRI or the production of N-acyl-L-homoserine lactones. Mol. 449 Microbiol., 55, 998-1014.

Diggle, S. P., Winzer, K., Chhabra, S. R., Worrall, K. E., Cámara, M. & Williams, P. (2003). The Pseudomonas aeruginosa quinolone signal molecule overcomes the cell density-dependency of the quorum sensing hierarchy, regulates rhl-dependent genes at the onset of stationary phase and can be produced in the absence of LasR. Mol. Microbiol., 50, 29-43.

Duan, K. & Surette, M. G. (2007). Environmental regulation of Pseudomonas aeruginosa PAO1 Las and Rhl quorum-sensing systems. J. Bacteriol., 189, 4827-4836.

Eibergen, N. R., Moore, J. D., Mattmann, M. E. & Blackwell, H. E. (2015). Potent and selective modulation of the RhlR quorum sensing receptor by using non-native ligands: an emerging target for virulence control in Pseudomonas aeruginosa. ChemBioChem, 16, 2348-2356.

Farha, M. A. & Brown, E. D. (2010). Chemical probes of Escherichia coli uncovered through chemical-chemical interaction profiling with compounds of known biological activity. Chem. Biol., 17, 852-862.

Folkesson, A., Jelsbak, L., Yang, L., Johansen, H. K., Ciofu, O., Høiby, N. & Molin, S. (2012). Adaptation of Pseudomonas aeruginosa to the cystic fibrosis airway: an evolutionary perspective. Nat. Rev. Microbiol., 10, 841-851.

Fuqua, C. & Greenberg, E. P. (2002). Listening in on bacteria: acyl-homoserine lactone signalling. Nat. Rev. Mol. Cell Biol., 3, 685-695.

Galloway, W. R. J. D., Hodgkinson, J. T., Bowden, S. D., Welch, M. & Spring, D. R. (2011). Quorum sensing in Gram-negative bacteria: small-molecule modulation of AHL and AI-2 quorum sensing pathways. Chem. Rev., 111, 28-67.

Gerdt, J. P. & Blackwell, H. E. (2014). Competition studies confirm two major barriers that can preclude the spread of resistance to quorum-sensing inhibitors in bacteria. ACS Chem. Biol., 9,469 2291-2299.

Geske, G. D., Mattmann, M. E. & Blackwell, H. E. (2008). Evaluation of a focused library of N-aryl L-homoserine lactones reveals a new set of potent quorum sensing modulators. Bioorg. Med. Chem. Lett., 18, 5978-5981(a).

Geske, G. D., O'Neill, J. C., Miller D. M., Wezeman, R. J., Mattmann, M. E., Lin, Q., Blackwell, H. E., (2008). Comparative analyses of N-acylated homoserine lactones reveal unique structural features that dictate their ability to activate or inhibit quorum sensing. ChemBioChem 9, 389-400 (b) Geske, G. D., O'Neill, J. C., Miller, D. M., Mattmann, M. E. & Blackwell, H. E. (2007). Modulation of bacterial quorum sensing with synthetic ligands: systematic evaluation of N-acylated homoserine lactones in multiple species and new insights into their mechanisms of action. J. Am. Chem. Soc., 129, 13613-13625.

Geske, G. D.; Wezeman, R. J.; Siegel, A. P.; Blackwell, H. E. (2005) Small molecule inhibitors of bacterial quorum sensing and biofilm formation. J. Am. Chem. Soc. 127, 12762-12763.

Gilbert, K. B., Kim, T. H., Gupta, R., Greenberg, E. P. & Schuster, M. (2009). Global position analysis of the Pseudomonas aeruginosa quorum-sensing transcription factor LasR. Mol. Microbiol., 73, 1072-1085.

Goo, E., An, J. H., Kang, Y. & Hwang, I. (2015). Control of bacterial metabolism by quorum sensing. Trends Microbiol., 23, 567-576.

Hense, B. A. & Schuster, M. (2015). Core principles of bacterial autoinducer systems. Microbiol. 483 Mol. Biol. Rev., 79, 153-169.

Hentzer, M.; Wu, H.; Andersen, J. B.; Riedel, K.; Rasmussen, T. B.; Bagge, N.; Kumar, N.; Schembri, M. A.; Song, Z.; Kristoffersen, P.; Manefield, M.; Costerton, J. W.; Molin, S.; Eberl, L.; Steinberg, P.; Kjelleberg, S.; Hoiby, N.; Givskov, M. (2003) Attenuation of *Pseudomonas aeruginosa* virulence by quorum sensing inhibitors. EMBO J. 22, 3803-3815.

Hoang, T. T.; Karkhoff-Schweizer, R. R., Kutchma, A. J. & Schweizer, H. P. (1998). A broad-host-range Flp-FRT recombination system for site-specific excision of chromosomally-located DNA sequences: application for isolation of unmarked *Pseudomonas aeruginosa* mutants. Gene, 212, 77-86.

Hodgkinson, J. T. et al. (2012). Design, synthesis and biological evaluation of non-natural modulators of quorum sensing in *Pseudomonas aeruginosa*. Org. Biomol. Chem., 10, 6032-6044.

Holloway, B. W. (1955). Genetic recombination in *Pseudomonas aeruginosa*. J. Gen. Microbiol., 13, 572-581.

Ishida, T.; Ikeda, T.; Takiguchi, N.; Kuroda, A.; Ohtake, H.; Kato, J. (2007) Inhibition of Quorum Sensing in *Pseudomonas aeruginosa* by N-Acyl Cyclopentylamides. Appl. Environ. Microbiol. 73, 3183-3188.

Jensen, V., Lons, D., Zaoui, C., Bredenbruch, F., Meissner, A., Dieterich, G., Munch, R. & Haussler, S. (2006). RhlR expression in *Pseudomonas aeruginosa* is modulated by the *Pseudomonas* quinolone signal via PhoB-dependent and -independent pathways. J. Bacteriol., 188, 8601-8606.

Koch, A. K., Käppeli, O., Fiechter, A. & Reiser, J. (1991). Hydrocarbon assimilation and biosurfactant production in *Pseudomonas aeruginosa* mutants. J. Bacteriol., 173, 4212-4219.

Lee, J., Wu, J., Deng, Y., Wang, J., Wang, C., Wang, J., Chang, C., Dong, Y., Williams, P. & Zhang, L.-H. (2013). A cell-cell communication signal integrates quorum sensing and stress response. Nat. Chem. Biol., 9, 339-343.

Lee, J. & Zhang, L. (2015). The hierarchy quorum sensing network in *Pseudomonas aeruginosa*. Protein Cell, 6, 26-41.

Long, J., Zaborina, O., Holbrook, C., Zaborin, A. & Alverdy, J. (2008). Depletion of intestinal phosphate after operative injury activates the virulence of *P. aeruginosa* causing lethal gut derived sepsis. Surgery, 144, 189-197.

Lu, C., Kirsch, B., Zimmer, C., De Jong, Johannes C., Henn, C., Maurer, Christine K., Müsken, M., Häussler, S., Steinbach, A. & Hartmann, Rolf W. (2012). Discovery of antagonists of PqsR, a key player in 2-alkyl-4-quinolone-dependent quorum sensing in *Pseudomonas aeruginosa*. Chem. Biol., 19, 381-390.

Lyczak, J. B., Cannon, C. L. & Pier, G. B. (2000). Establishment of *Pseudomonas aeruginosa* infection: lessons from a versatile opportunist. Microbes Infect., 2, 1051-1060.

Markou, P. & Apidianakis, Y. (2014). Pathogenesis of intestinal *Pseudomonas aeruginosa* infection in patients with cancer. Front. Cell. Infect. Microbiol., 3, 115.

Mattmann, M. E., Shipway, P. M., Heth, N. J. & Blackwell, H. E. (2011). Potent and selective synthetic modulators of a quorum sensing repressor in *Pseudomonas aeruginosa* identified from second-generation libraries of N-acylated L-homoserine lactones. ChemBioChem, 12, 942-949.

M. E. Mattmann, G. D. Geske, G. A. Worzalla, J. R. Chandler, K. J. Sappington, E. P. Greenberg, H. E. Blackwell (2008). Synthetic ligands that activate and inhibit a quorum-sensing regulator in *Pseudomonas aeruginosa*. Bioorg. Med. Chem. Lett. 18, 3072-075.

McInnis, C. E.; Blackwell, H. E. (2011). Thiolactone modulators of quorum sensing revealed through library design and screening. Biorgan. Med. Chem. 19, 4812-4819.

Mellbye, B. & Schuster, M. (2014). Physiological framework for the regulation of quorum sensing-dependent public goods in *Pseudomonas aeruginosa*. J. Bacteriol., 196, 1155-1164.

Moore, J. D., Rossi, F. M., Welsh, M. A., Nyffeler, K. E. & Blackwell, H. E. (2015). A comparative analysis of synthetic quorum sensing modulators in *Pseudomonas aeruginosa*: New insights into mechanism, active efflux susceptibility, phenotypic response, and next-generation ligand design. J. Am. Chem. Soc., 137(46), 14626-14639.

Moore, J. D., Gerdt, J. P., Eibergen, N. R., Blackwell, H. E. (2014) Active efflux influences the potency of quorum sensing inhibitors in *Pseudomonas aeruginosa*. ChemBioChem 15, 435-442.

Morkunas, B et al. (2012). Inhibition of the production of the *Pseudomonas aeruginosa* virulence factor pyocyanin in wild-type cells by quorum sensing autoinducer-mimics. Org. Biomol., 42, 8452-8464.

Müh, U., Schuster, M., Heim, R., Singh, A., Olson, E. R. & Greenberg, E. P. (2006). Novel *Pseudomonas aeruginosa* quorum-sensing inhibitors identified in an ultra-high-throughput screen. Antimicrob. Agents Chemother., 50, 3674-3679(a)

Müh, U.; Hare, B. J.; Duerkop, B. A.; Schuster, M.; Hanzelka, B. L.; Heim, R.; Olson, E. Muh, U.; Hare, B. J.; Duerkop, B. A.; Schuster, M.; Hanzelka, B. L.; Heim, R.; Olson, E. R.; Greenberg, E. P. (2006) A structurally unrelated mimic of a *Pseudomonas aeruginosa* acyl-homoserine lactone quorum-sensing signal. Proc. Natl. Acad. Sci. U.S.A 103, 16948-16952 (b)

Murray, E. J., et al. (2014). Targeting *Staphylococcus aureus* quorum sensing with nonpeptidic small molecule inhibitors. J. Med. Chem., 57, 2813-2819.

O'Brien, K. T.; Noto, J. G.; Nichols-O'Neill, L.; Perez, L. J. (2015). Potent Irreversible Inhibitors of LasR Quorum Sensing in *Pseudomonas aeruginosa*. ACS Medicinal Chemistry Letters, 6, 162-167.

O'Loughlin, C. T., Miller, L. C., Siryaporn, A., Drescher, K., Semmelhack, 516 M. F. & Bassler, B. L. (2013). A quorum-sensing inhibitor blocks *Pseudomonas aeruginosa* virulence and biofilm formation. Proc. Natl. Acad. Sci. U.S.A, 110, 17981-17986.

O'Reilly, M. C. and Blackwell, H. E. (2015). Structure-Based Design and Biological Evaluation of Triphenyl Scaffold-Based Hybrid Compounds as Hydrolytically Stable Modulators of a LuxR-Type Quorum Sensing Receptor. ACS Infect. Dis, 2, 32-38.

Oglesby, A. G., Farrow, J. M., Lee, J.-H., Tomaras, A. P., Greenberg, E. P., Pesci, E. C. & Vasil, M. L. (2008). The influence of iron on *Pseudomonas aeruginosa* physiology: a regulatory link between iron and quorum sensing. J. Biol. Chem., 283, 15558-15567.

Persson, T.; Hansen, T. H.; Rasmussen, T. B.; Skinderso, M. E.; Givskov, M.; Nielsen, J. (2005) Rational design and synthesis of new quorum-sensing inhibitors derived from acylated homoserine lactones and natural products from garlic. Org. Biomol. Chem. 3, 253-262.

Praneenararat, T., Palmer, A. G. & Blackwell, H. E. (2012). Chemical methods to interrogate bacterial quorum sensing pathways. Org. Biomol. Chem., 10, 8189-8199.

Rampioni, G., Pustelny, C., Fletcher, M. P., Wright, V. J., Bruce, M., Rumbaugh, K. P., Heeb, S., Cámara, M. & Williams, P. (2010). Transcriptomic analysis reveals a global alkyl-quinolone independent regulatory role for PqsE in facilitating the environmental adaptation of *Pseudomonas aeruginosa* to plant and animal hosts. Environ. Microbiol., 12, 1659-1673.

Recinos, D. A., Sekedat, M. D., Hernandez, A., Cohen, T. S., Sakhtah, H., Prince, A. S., Price-Whelan, A. & Dietrich, L. E. P. (2012). Redundant phenazine operons in *Pseudomonas aeruginosa* exhibit environment-dependent expression and differential roles in pathogenicity. Proc. Natl. Acad. Sci. U.S.A, 109, 19420-19425.

Reis, R. S., Pereira, A. G., Neves, B. C. & Freire, D. M. G. (2011). Gene regulation of rhamnolipid production in *Pseudomonas aeruginosa*—a review. Biores. Tech., 102, 6377-6384.

Reverchon, S.; Chantegrel, B.; Deshayes, C.; Doutheau, A.; Cotte-Pattat, N. (2002) New synthetic analogues of N-acyl homoserine lactones as agonists or antagonists of transcriptional regulators involved in bacterial quorum sensing. Bioorg. Med. Chem. Lett. 12, 1153-1157.

Rojo, F. (2010). Carbon catabolite repression in *Pseudomonas*: optimizing metabolic versatility and interactions with the environment. FEMS Microbiol. Rev., 34, 658-684.

Rutherford, S. T. & Bassler, B. L. (2012). Bacterial quorum sensing: its role in virulence and possibilities for its control. Cold Spring Harb. Perspect. Med., 2, a012427.

Schafhauser, J., Lepine, F., Mckay, G., Ahlgren, H. G., Khakimova, M. & Nguyen, D. (2014). The stringent response modulates 4-hydroxy-2-alkylquinoline (HAQ) biosynthesis and quorum sensing hierarchy in *Pseudomonas aeruginosa*. J. Bacteriol., 196, 1641-1650.

Schuster, M. & Greenberg, E. P. (2008). LuxR-type proteins in *Pseuodomonas aeruginosa* quorum sensing: Distinct mechanisms with global implications. In Chemical Communication Among Bacteria, Winans, S. C. & Bassler, B. L. eds. (Washington, D.C.: ASM Press), pp. 133-144.

Shrout, J. D., Chopp, D. L., Just, C. L., Hentzer, M., Givskov, M. & Parsek, M. R. (2006). The impact of quorum sensing and swarming motility on *Pseudomonas aeruginosa* biofilm formation is nutritionally conditional. Mol. Microbiol., 62, 1264-1277.

Simon, R., Priefer, U. & Puhler, A. (1983). A broad host range mobilization system for in vivo genetic engineering: Transposon mutagenesis in Gram negative bacteria. Nat. Biotechnol., 1, 784-791.

Smith, K. M.; Bu, Y.; Suga, H. (2003) Library screening for synthetic agonists and antagonists of a *Pseudomonas aeruginosa* autoinducer. Chem. Biol. 10, 563-571 (a).

Smith, K. M.; Bu, Y.; Suga, H. (2003) Induction and inhibition of *Pseudomonas aeruginosa* quorum sensing by synthetic autoinducer analogs. Chem. Biol. 10, 81-89 (b).

Starkey, M., et al. (2014). Identification of anti-virulence compounds that disrupt quorum sensing regulated acute and persistent pathogenicity. PLoS Pathog., 10, e1004321.

Swem, L. R.; Swem, D. L.; O'Loughlin, C. T.; Gatmaitan, R.; Zhao, B.; Ulrich, S. M.; Bassler, B. L. (2009) A Quorum-Sensing Antagonist Targets Both Membrane-Bound and Cytoplasmic Receptors And Controls Bacterial Pathogenicity. Mol. Cell 35, 143-153.

Turner, K. H., Wessel, A. K., Palmer, G. C., Murray, J. L. & Whiteley, 550 M. (2015). Essential genome of *Pseudomonas aeruginosa* in cystic fibrosis sputum. Proc. Natl. Acad. Sci. U.S.A, 112, 4110-4115.

Venturi, V. (2006). Regulation of quorum sensing in *Pseudomonas*. FEMS Microbiol. Rev., 30, 554 274-291.

Wagner, V. E., Bushnell, D., Passador, L., Brooks, A. I. & Iglewski, B. H. (2003). Microarray analysis of *Pseudomonas aeruginosa* quorum-sensing regulons: effects of growth phase and environment. J. Bacteriol., 185, 2080-2095.

Welsh, M. A., Eibergen, N. R., Moore, J. D. & Blackwell, H. E. (2015). Small molecule disruption of quorum sensing cross-regulation in *Pseudomonas aeruginosa* causes major and unexpected alterations to virulence phenotypes. J. Am. Chem. Soc., 137, 1510-1519.

White, C. E. & Winans, S. C. (2007). Cell-cell communication in the plant pathogen *Agrobacterium tumefaciens*. Phil. Trans. R. Soc. B, 362, 1135-1148.

Williams, P. & Cámara, M. (2009). Quorum sensing and environmental adaptation in *Pseudomonas aeruginosa*: a tale of regulatory networks and multifunctional signal molecules. Curr. Opin. Microbiol., 12, 182-191.

Wu, H.; Song, Z.; Hentzer, M.; Andersen, J. B.; Molin, S.; Givskov, M.; Høiby, N. J. (2004) Synthetic furanones inhibit quorum-sensing and enhance bacterial clearance in *Pseudomonas aeruginosa* lung infection in mice. Antimicrob. Chemother. 53, 1054-1061.

Yang, N., et al. (2015). The Crc protein participates in down-regulation of the Lon gene to promote rhamnolipid production and rhl quorum sensing in *Pseudomonas aeruginosa*. Mol. Microbiol., 96, 526-547.

Zakhari, J. S.; Kinoyama, I.; Struss, A. K.; Pullanikat, P.; Lowery, C. A.; Lardy, M.; Janda, K. D. (2011) Synthesis and Molecular Modeling Provide Insight into a *Pseudomonas aeruginosa* Quorum Sensing Conundrum. J. Am. Chem. Soc., 133, 3840-3842.

Zhu et al. (1998). Analogs of the Autoinducer 3-Oxooctanoyl-Homoserine Lactone Strongly Inhibit Activity of the TraR Protein of *Agrobacterium tumefaciens*. J. Bacteriol. 180, 5398-5405

---

We claim:

1. A method for inhibiting quorum sensing in a Gram-negative bacterium having multiple quorum sensing systems which comprises contacting the bacterium or an environment containing the bacterium with a combination of a first quorum sensing inhibitor selective for a first quorum sensing system and at least a second quorum sensing inhibitor selective for a second quorum sensing system, wherein the first quorum sensing inhibitor is:

(compound 2 (E22))

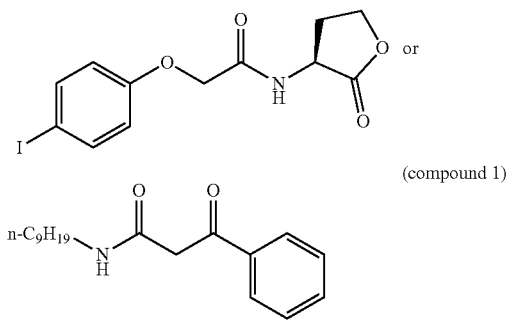

(compound 1)

and the second quorum sensing inhibitor is:

(compound 4 (M64))

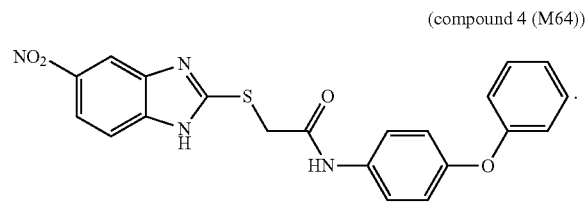 [SMILES: O=C(CSc1nc2cc([N+](=O)[O-])ccc2[nH]1)Nc1ccc(Oc2ccccc2)cc1]

2. The method of claim 1, wherein the Gram-negative bacterium is a species of the genus *Pseudomonas*.

3. The method of claim 1, wherein the first quorum-sensing inhibitor is:

(compound 2 (E22))

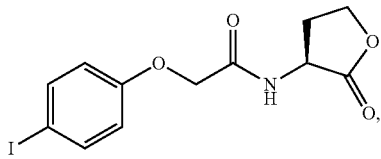

and the second quorum sensing inhibitor is:

(compound 4 (M64))

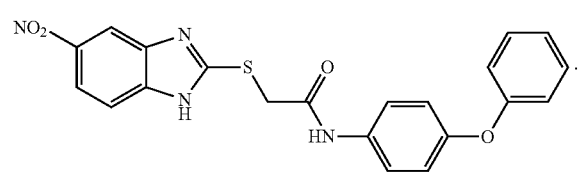

4. The method of claim 1, wherein, the environment of the Gram-negative bacterium is depleted in one or more nutrients needed for the bacterium.

5. The method of claim 4, wherein the environment is depleted in iron or phosphate.

6. The method of claim 4, wherein the Gram-negative bacterium is a strain of the genus *Pseudomonas*.

7. The method of claim 5, wherein the Gram-negative bacterium is a strain of the genus *Pseudomonas*.

8. The method of claim 1, wherein the Gram-negative bacterium is a strain of *Pseudomonas aeruginosa*.

9. The method of claim 4, wherein the Gram-negative bacterium is a strain of *Pseudomonas aeruginosa*.

10. The method of claim 5, wherein the Gram-negative bacterium is a strain of *Pseudomonas aeruginosa*.

* * * * *